United States Patent
Lo et al.

(10) Patent No.: US 12,416,049 B2
(45) Date of Patent: Sep. 16, 2025

(54) METHYLATION PATTERN ANALYSIS OF HAPLOTYPES IN TISSUES IN A DNA MIXTURE

(71) Applicant: The Chinese University of Hong Kong, Shatin (CN)

(72) Inventors: Yuk-Ming Dennis Lo, Kowloon (CN); Kwan Chee Chan, Jordan (CN); Rossa Wai Kwun Chiu, Shatin (CN); Peiyong Jiang, Shatin (CN); Kun Sun, Shatin (CN)

(73) Assignee: The Chinese University of Hong Kong, Shatin (HK)

( * ) Notice: Subject to any disclaimer, the term of this patent is extended or adjusted under 35 U.S.C. 154(b) by 1407 days.

(21) Appl. No.: 16/874,215

(22) Filed: May 14, 2020

(65) Prior Publication Data
US 2020/0270707 A1   Aug. 27, 2020

Related U.S. Application Data

(62) Division of application No. 15/214,998, filed on Jul. 20, 2016, now Pat. No. 10,689,706.

(60) Provisional application No. 62/194,702, filed on Jul. 20, 2015.

(51) Int. Cl.
*C12Q 1/6886* (2018.01)
*C12Q 1/6883* (2018.01)
*G16B 30/00* (2019.01)

(52) U.S. Cl.
CPC ......... *C12Q 1/6886* (2013.01); *C12Q 1/6883* (2013.01); *G16B 30/00* (2019.02); *C12Q 2600/154* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 8,467,976 B2 | 6/2013 | Lo et al. | |
| 10,689,706 B2 | 6/2020 | Lo et al. | |
| 2014/0080715 A1 | 3/2014 | Lo et al. | |
| 2014/0315200 A1 | 10/2014 | Lo et al. | |
| 2015/0004601 A1 | 1/2015 | Struble et al. | |
| 2016/0017419 A1 | 1/2016 | Chiu et al. | |
| 2016/0340740 A1 | 11/2016 | Zhang | |
| 2017/0121767 A1 | 5/2017 | Dor et al. | |

FOREIGN PATENT DOCUMENTS

| | | |
|---|---|---|
| CN | 102770558 A | 11/2012 |
| CN | 103459614 A | 12/2013 |
| CN | 103492589 A | 1/2014 |
| CN | 104781422 A | 7/2015 |
| TW | 201418474 A | 5/2014 |
| WO | 2011018600 A1 | 2/2011 |
| WO | 2011057094 A1 | 5/2011 |
| WO | 2014043763 A1 | 3/2014 |

OTHER PUBLICATIONS

Australian Application No. 2016295712, First Examination Report mailed on Sep. 10, 2021, 4 pages.
Australian Application No. 2016295712, Notice of Acceptance mailed on May 24, 2022, 3 pages.
Chim et al., Detection of the Placental Epigenetic Signature of the Maspin Gene in Maternal Plasma, PNAS, vol. 102, No. 41, Oct. 11, 2005, pp. 14753-14758.
European Application No. 16827235.9, Extended European Search Report mailed on Jun. 27, 2018, 12 pages.
European Application No. 16827235.9, Office Action mailed on Apr. 8, 2019, 7 pages.
European Application No. 20183986.7, Extended European Search Report mailed on Sep. 28, 2020, 8 pages.
European Application No. 22162789.6, Extended European Search Report mailed on Aug. 31, 2022, 12 pages.
Hill et al., Uses of Cell Free Fetal DNA in Maternal Circulation, Best Practice & Research: Clinical Obstetrics & Gynaecology, vol. 26, No. 5, Oct. 2012, pp. 639-654.
Nygren et al., Quantification of Fetal DNA by Use of Methylation-Based DNA Discrimination, Clinical Chemistry, vol. 56, No. 10, Available Online at: http://www.clinchem.org/content/suppl/2010/07/28/clinchem.2010.146290.DC1/clinchem.2010.146290-1.pdf, Aug. 20, 2010, pp. 1627-1635.
Ou et al., Epigenome-Wide DNA Methylation Assay Reveals Placental Epigenetic Markers for Noninvasive Fetal Single-Nucleotide Polymorphism Genotyping in Maternal Plasma, Transfusion, vol. 54, No. 10, Oct. 2014, pp. 2523-2533.
International Application No. PCT/CN2016/090642, International Search Report and Written Opinion mailed on Oct. 19, 2016, 5 pages.
Sun et al., Plasma DNA Tissue Mapping by Genome-Wide Methylation Sequencing for Noninvasive Prenatal, Cancer, and Transplantation Assessments, Proceedings of the National Academy of Sciences, vol. 112, No. 40, Sep. 21, 2015, pp. E5503-E5512.
Taiwan Application No. 105122965, Office Action mailed on May 29, 2020, 18 pages (8 pages of English Translation and 10 pages of Original Document).
Taiwan Application No. 110121521, Office Action mailed on Jul. 29, 2022, 8 pages (3 pages of English Translation and 5 pages of Original Document).

(Continued)

*Primary Examiner* — Joseph Woitach
(74) *Attorney, Agent, or Firm* — Kilpatrick Townsend & Stockton LLP

(57) ABSTRACT

Systems, apparatuses, and method are provided for determining the contributions of different tissues to a biological sample that includes a mixture of cell-free DNA molecules from various tissues types, e.g., as occurs in plasma or serum and other body fluids. Embodiments can analyze the methylation patterns of the DNA mixture (e.g., methylation levels at particular loci) for a particular haplotype and determine fractional contributions of various tissue types to the DNA mixture, e.g., of fetal tissue types or tissue types of specific organs that might have a tumor. Such fractional contributions determined for a haplotype can be used in a variety of ways.

23 Claims, 22 Drawing Sheets

(56) References Cited

OTHER PUBLICATIONS

Zheng et al., Methylpurify: Tumor Purity Deconvolution and Differential Methylation Detection from Single Tumor DNA Methylomes, Genome Biology, Biomed Central Ltd, vol. 15, No. 8, Aug. 7, 2014, 13 pages.

400

| Case no. | Percentage contributions of plasma DNA (%) | | | | | | | | | | | | | SNP-based fetal DNA fraction (%) | Gestational age (weeks) |
|---|---|---|---|---|---|---|---|---|---|---|---|---|---|---|---|
| | Liver | Lungs | Colon | Small intestines | Pancreas | Adrenal glands | Esophagus | Adipose tissues | Heart | Brain | Neutrophils | Lymphocytes | Placenta | | |
| 1 | 1.5 | 9.3 | 0.0 | 0.0 | 0.0 | 1.9 | 0.0 | 12.1 | 0.0 | 48.1 | 17.0 | 10.0 | 13.6 | 13.1/7 |
| 2 | 2.5 | 7.6 | 0.0 | 2.8 | 0.0 | 0.0 | 0.0 | 12.6 | 0.0 | 46.6 | 18.6 | 9.9 | 13.9 | 13 |
| 3 | 3.9 | 5.8 | 0.0 | 0.7 | 0.0 | 0.6 | 0.0 | 12.4 | 0.0 | 49.2 | 17.4 | 10.1 | 14.0 | 12 6/7 |
| 4 | 0.6 | 9.2 | 0.0 | 1.8 | 0.0 | 0.0 | 0.0 | 10.6 | 0.0 | 44.1 | 21.1 | 12.7 | 16.1 | 13 |
| 5 | 11.1 | 5.2 | 0.0 | 5.7 | 0.0 | 0.0 | 0.0 | 5.1 | 0.0 | 45.0 | 11.7 | 16.2 | 17.1 | 12 6/7 |
| 6 | 8.1 | 6.4 | 0.0 | 0.0 | 0.0 | 1.3 | 0.0 | 4.5 | 1.7 | 51.9 | 17.0 | 10.8 | 13.1 | 21 3/7 |
| 7 | 3.0 | 6.2 | 0.0 | 0.0 | 0.0 | 0.5 | 0.0 | 10.1 | 0.0 | 39.3 | 24.5 | 12.5 | 15.2 | 20 6/7 |
| 8 | 0.8 | 6.5 | 0.0 | 0.0 | 0.0 | 0.0 | 0.0 | 10.2 | 0.0 | 51.7 | 15.5 | 13.3 | 16.4 | 22 2/7 |
| 9 | 0.0 | 8.0 | 0.0 | 0.0 | 1.6 | 0.0 | 0.0 | 9.2 | 0.0 | 41.7 | 18.1 | 20.4 | 22.3 | 22 1/7 |
| 10 | 2.6 | 2.6 | 0.0 | 0.0 | 0.0 | 0.0 | 0.0 | 4.1 | 0.0 | 40.5 | 18.3 | 34.9 | 34.3 | 21 6/7 |
| 11 | 0.0 | 7.4 | 0.0 | 0.0 | 0.0 | 0.0 | 0.0 | 9.8 | 0.0 | 41.5 | 22.0 | 19.3 | 21.0 | 38 1/7 |
| 12 | 0.8 | 10.3 | 0.0 | 0.0 | 0.0 | 1.7 | 0.0 | 8.6 | 0.0 | 39.0 | 18.7 | 24.3 | 27.0 | 38 3/7 |
| 13 | 0.0 | 7.4 | 0.0 | 0.0 | 0.0 | 0.0 | 0.0 | 8.3 | 0.0 | 38.7 | 18.7 | 29.2 | 33.0 | 38 1/7 |
| 14 | 0.0 | 5.9 | 0.0 | 0.0 | 0.0 | 0.0 | 0.0 | 8.3 | 0.0 | 39.6 | 12.9 | 33.3 | 36.8 | 38 2/7 |
| 15 | 0.0 | 7.3 | 0.0 | 0.0 | 0.0 | 0.0 | 0.0 | 7.2 | 0.0 | 32.5 | 14.6 | 38.4 | 39.5 | 38 3/7 |

FIG. 4

| Case no. | Percentage contributions of plasma DNA (%) | | | | | | | | | | | | |
|---|---|---|---|---|---|---|---|---|---|---|---|---|---|
| | Liver | Lungs | Colon | Small intestines | Pancreas | Adrenal glands | Esophagus | Adipose tissues | Heart | Brain | Neutrophils | Lymphocytes | Placenta |
| 1 | 5.8 | 6.6 | 0.0 | 1.3 | 0.0 | 0.0 | 0.0 | 6.2 | 2.9 | 0.0 | 58.2 | 18.8 | 0.0 |
| 2 | 5.1 | 5.2 | 0.0 | 7.3 | 0.0 | 0.0 | 0.0 | 4.5 | 0.0 | 0.0 | 61.8 | 16.1 | 0.0 |
| 3 | 5.5 | 7.8 | 0.0 | 2.1 | 0.0 | 0.0 | 0.0 | 6.5 | 0.6 | 0.0 | 58.8 | 18.8 | 0.0 |
| 4 | 4.1 | 6.4 | 0.0 | 4.5 | 0.0 | 0.0 | 0.0 | 5.9 | 1.3 | 0.4 | 59.0 | 16.4 | 0.0 |
| 5 | 4.4 | 2.5 | 0.7 | 6.4 | 0.0 | 0.0 | 0.0 | 5.5 | 2.7 | 0.6 | 59.6 | 17.1 | 0.3 |
| 6 | 5.8 | 4.1 | 0.0 | 5.3 | 0.0 | 0.0 | 0.0 | 5.2 | 0.5 | 0.8 | 55.2 | 22.7 | 0.5 |
| 7 | 4.3 | 4.1 | 0.0 | 4.5 | 0.0 | 0.0 | 0.0 | 6.3 | 0.0 | 0.0 | 60.2 | 20.9 | 0.0 |
| 8 | 4.4 | 7.4 | 0.0 | 5.3 | 0.0 | 0.0 | 0.0 | 3.1 | 0.3 | 0.3 | 61.7 | 17.5 | 0.0 |
| 9 | 4.5 | 9.4 | 0.0 | 4.0 | 0.0 | 0.0 | 0.0 | 6.2 | 0.1 | 1.2 | 55.9 | 18.8 | 0.0 |
| 10 | 4.6 | 0.1 | 0.2 | 1.3 | 0.0 | 0.0 | 0.0 | 7.5 | 0.0 | 2.4 | 60.0 | 23.9 | 0.0 |
| 11 | 4.7 | 4.5 | 0.0 | 5.5 | 0.0 | 0.0 | 0.0 | 5.5 | 0.9 | 0.5 | 62.4 | 16.0 | 0.0 |
| 12 | 7.3 | 4.9 | 0.0 | 4.4 | 0.0 | 0.0 | 0.0 | 6.0 | 1.8 | 0.9 | 54.0 | 20.7 | 0.0 |
| 13 | 2.4 | 10.9 | 0.0 | 1.7 | 0.0 | 0.0 | 0.0 | 5.7 | 0.0 | 0.6 | 53.9 | 24.5 | 0.3 |
| 14 | 3.8 | 3.5 | 0.0 | 0.0 | 0.0 | 0.0 | 0.0 | 8.9 | 0.0 | 0.0 | 61.2 | 22.7 | 0.0 |
| 15 | 5.3 | 7.2 | 0.0 | 4.2 | 0.0 | 0.2 | 0.0 | 5.1 | 0.0 | 0.1 | 56.3 | 21.6 | 0.0 |
| 16 | 4.9 | 6.5 | 0.0 | 7.8 | 0.0 | 0.0 | 0.0 | 4.3 | 0.5 | 1.2 | 55.4 | 18.9 | 0.4 |
| 17 | 16.6 | 12.8 | 0.0 | 0.0 | 0.0 | 0.0 | 0.0 | 4.4 | 0.0 | 0.0 | 47.7 | 18.5 | 0.0 |
| 18 | 6.3 | 5.0 | 0.0 | 2.1 | 0.0 | 0.0 | 0.0 | 7.5 | 0.0 | 0.2 | 58.2 | 19.4 | 1.3 |
| 19 | 6.0 | 0.0 | 1.0 | 2.3 | 0.0 | 0.0 | 0.0 | 9.3 | 0.0 | 0.0 | 54.5 | 26.3 | 0.6 |
| 20 | 2.0 | 4.8 | 0.0 | 0.0 | 0.0 | 0.5 | 0.0 | 10.5 | 0.0 | 0.0 | 58.5 | 22.5 | 1.1 |
| 21 | 8.5 | 0.0 | 0.0 | 4.5 | 0.0 | 0.0 | 0.0 | 9.4 | 0.0 | 0.0 | 53.9 | 23.4 | 0.2 |
| 22 | 6.4 | 11.3 | 0.0 | 4.0 | 0.0 | 0.0 | 0.0 | 6.7 | 0.0 | 0.0 | 53.7 | 18.1 | 0.0 |
| 23 | 3.0 | 2.8 | 0.0 | 8.7 | 0.0 | 0.0 | 0.0 | 6.5 | 1.1 | 0.0 | 62.5 | 15.0 | 1.3 |
| 24 | 5.4 | 2.2 | 0.0 | 2.7 | 0.0 | 0.0 | 0.0 | 6.9 | 0.0 | 1.6 | 65.2 | 15.2 | 0.9 |
| 25 | 21.0 | 0.0 | 0.0 | 7.1 | 0.0 | 0.0 | 0.0 | 3.8 | 0.0 | 0.0 | 51.6 | 16.4 | 0.0 |
| 26 | 7.0 | 6.4 | 0.0 | 6.1 | 0.0 | 0.0 | 0.0 | 4.1 | 1.6 | 0.0 | 55.9 | 19.0 | 0.0 |
| 27 | 7.9 | 10.4 | 0.0 | 0.3 | 0.0 | 0.0 | 0.0 | 4.9 | 0.0 | 0.0 | 59.1 | 17.5 | 0.0 |
| 28 | 5.4 | 9.7 | 0.0 | 4.2 | 0.0 | 0.0 | 0.0 | 5.1 | 0.0 | 0.0 | 55.7 | 20.0 | 0.0 |
| 29 | 6.2 | 6.6 | 0.0 | 0.0 | 0.0 | 0.0 | 0.0 | 6.3 | 0.0 | 0.0 | 60.7 | 20.2 | 0.0 |
| 30 | 6.9 | 5.1 | 0.0 | 5.2 | 0.0 | 0.0 | 0.0 | 6.4 | 1.4 | 0.0 | 56.8 | 18.2 | 0.0 |
| 31 | 14.0 | 6.4 | 0.0 | 4.5 | 0.0 | 0.0 | 0.0 | 4.9 | 0.7 | 0.0 | 53.2 | 16.3 | 0.0 |
| 32 | 9.3 | 6.5 | 0.0 | 1.9 | 0.0 | 0.0 | 0.0 | 6.3 | 0.6 | 0.0 | 60.1 | 15.6 | 0.0 |
| Median | 5.5 | 5.3 | 0.0 | 4.2 | 0.0 | 0.0 | 0.0 | 6.3 | 0.0 | 0.0 | 58.3 | 18.7 | 0.0 |
| Lower quartile | 4.5 | 3.8 | 0.0 | 1.9 | 0.0 | 0.0 | 0.0 | 5.0 | 0.0 | 0.0 | 55.0 | 16.5 | 0.0 |
| Upper quartile | 7.1 | 7.3 | 0.0 | 5.3 | 0.0 | 0.0 | 0.0 | 6.6 | 0.0 | 0.5 | 60.1 | 21.0 | 0.3 |

FIG. 6

|  | Pregnant women | | | | | | | | | | | Non-pregnant subjects | | | |
|---|---|---|---|---|---|---|---|---|---|---|---|---|---|---|---|
|  | 1 | 2 | 3 | 4 | 5 | 6 | 7 | 8 | 9 | 10 | 11 | 1 | 2 | 3 | 4 |
| Buffy coat | 58% | 64% | 65% | 53% | 83% | 52% | 75% | 71% | 52% | 66% | 69% | 87% | 83% | 96% | 80% |
| Esophagus | 0% | 0% | 0% | 2% | 0% | 0% | 0% | 3% | 0% | 0% | 0% | 0% | 0% | 0% | 0% |
| Small intestines | 0% | 0% | 0% | 4% | 0% | 0% | 0% | 0% | 0% | 0% | 0% | 0% | 0% | 0% | 0% |
| Colon | 0% | 0% | 0% | 0% | 0% | 0% | 0% | 0% | 0% | 0% | 0% | 0% | 5% | 0% | 0% |
| Pancreas | 0% | 1% | 0% | 1% | 0% | 0% | 0% | 0% | 1% | 3% | 2% | 1% | 0% | 0% | 0% |
| Liver | 3% | 8% | 10% | 1% | 0% | 11% | 6% | 7% | 4% | 9% | 8% | 7% | 7% | 3% | 6% |
| Lung | 0% | 0% | 0% | 0% | 0% | 0% | 0% | 0% | 0% | 0% | 0% | 0% | 0% | 0% | 0% |
| Heart | 0% | 0% | 0% | 0% | 0% | 0% | 0% | 0% | 0% | 0% | 10% | 0% | 0% | 0% | 2% |
| Adrenal gland | 0% | 1% | 0% | 1% | 0% | 0% | 1% | 0% | 0% | 0% | 1% | 0% | 0% | 0% | 5% |
| Hippocampus | 1% | 3% | 0% | 1% | 2% | 4% | 0% | 4% | 3% | 3% | 4% | 2% | 5% | 0% | 5% |
| Placenta | 38% | 24% | 25% | 36% | 15% | 34% | 18% | 15% | 40% | 19% | 7% | 2% | 0% | 1% | 2% |
|  |  |  |  |  |  |  |  |  |  |  |  |  |  |  |  |
| Fetal DNA fraction determined by counting fetal specific alleles | 32% | 21% | 26% | 28% | 11% | 25% | 17% | 13% | 13% | 32% | 3% | 0% | 0% | 0% | 0% |

| | Pregnant women | | | | | | | | | | | Non-pregnant subjects | | | |
|---|---|---|---|---|---|---|---|---|---|---|---|---|---|---|---|
| | 1 | 2 | 3 | 4 | 5 | 6 | 7 | 8 | 9 | 10 | 11 | 1 | 2 | 3 | 4 |
| Buffy coat | 43% | 44% | 47% | 40% | 47% | 41% | 38% | 41% | 43% | 39% | 45% | 10% | 11% | 1% | 13% |
| Esophagus | 0% | 0% | 0% | 0% | 0% | 0% | 0% | 0% | 0% | 0% | 0% | 0% | 0% | 0% | 0% |
| Small intestines | 0% | 4% | 1% | 2% | 3% | 0% | 1% | 5% | 0% | 0% | 0% | 0% | 0% | 0% | 0% |
| Colon | 25% | 18% | 10% | 23% | 14% | 23% | 24% | 20% | 27% | 25% | 16% | 17% | 7% | 22% | 27% |
| Pancreas | 0% | 0% | 0% | 0% | 0% | 0% | 0% | 0% | 0% | 0% | 0% | 0% | 0% | 0% | 0% |
| Liver | 4% | 8% | 11% | 4% | 8% | 11% | 9% | 0% | 0% | 0% | 0% | 0% | 0% | 0% | 0% |
| Lung | 0% | 0% | 0% | 1% | 0% | 0% | 0% | 3% | 0% | 0% | 11% | 0% | 0% | 0% | 0% |
| Heart | 0% | 0% | 1% | 3% | 0% | 0% | 1% | 0% | 0% | 0% | 0% | 0% | 0% | 0% | 0% |
| Adrenal gland | 0% | 3% | 6% | 0% | 0% | 0% | 7% | 4% | 3% | 7% | 7% | 24% | 23% | 20% | 4% |
| Hippocampus | 7% | 10% | 7% | 11% | 12% | 10% | 8% | 15% | 9% | 11% | 16% | 44% | 42% | 41% | 50% |
| Placenta | 21% | 13% | 18% | 16% | 15% | 16% | 11% | 12% | 18% | 18% | 6% | 4% | 16% | 15% | 7% |
| | | | | | | | | | | | | | | | |
| Fetal DNA fraction determined by counting fetal specific alleles | 32% | 21% | 26% | 28% | 11% | 25% | 17% | 13% | 13% | 32% | 3% | 0% | 0% | 0% | 0% |

METHYLATION PATTERN ANALYSIS OF HAPLOTYPES IN TISSUES IN A DNA MIXTURE

CROSS-REFERENCES TO RELATED APPLICATIONS

The present application is a divisional of U.S. application Ser. No. 15/214,998 entitled "Methylation Pattern Analysis Of Haplotypes In Tissues In A DNA Mixture," filed Jul. 20, 2016, which claims priority from and is a nonprovisional application of U.S. Provisional Application No. 62/194,702, entitled "Methylation Pattern Analysis Of Haplotypes In Tissues In A DNA Mixture" filed Jul. 20, 2015, the entire contents of which are herein incorporated by reference for all purposes.

BACKGROUND

It has previously been demonstrated that through the analysis of plasma DNA of a pregnant woman carrying a fetus, the maternal haplotypes inherited by the fetus can be deduced using the process of relative haplotype dosage analysis (RHDO) (Lo et al. Sci Transl Med 2010; 2: 61ra91 and U.S. Pat. No. 8,467,976). The haplotype information for the pregnant woman can be used. The haplotype information can be obtained using family analysis or a method for the direct analysis of the haplotype (e.g. Fan et al. Nat Biotechnol 2011; 29: 51-57; Snyder et al. Nat Rev Genet 2015; 16: 344-358). SNPs that are heterozygous in the mother but homozygous in the father can be used for the RHDO analysis.

Such a use of specific SNPs can limit the loci that can be used, and therefore limit the amount of data and accuracy. Such use of specific SNPs may also limit the clinical utility of the method as DNA samples from additional family members may not be available, and methods for the direct analysis of haplotypes would add costs to the analysis.

BRIEF SUMMARY

Embodiments are described for determining the contributions of different tissues to a biological sample that includes a mixture of cell-free DNA molecules from various tissues types, e.g., as occurs in plasma or serum and other body fluids. Embodiments can analyze the methylation patterns of the DNA mixture (e.g., methylation levels at particular loci) for a particular haplotype and determine fractional contributions of various tissue types to the DNA mixture, e.g., of fetal tissue types or tissue types of specific organs that might have a tumor. Such fractional contributions determined for a haplotype can be used in a variety of ways.

In some embodiments, two fractional contributions of a tissue type can be determined using methylation levels of two sets of cell-free DNA molecules from a maternal sample, each set being for a different one of two parental haplotypes of a parent of a fetus, for a chromosomal region being analyzed. In various implementations, the maternal sample can be the plasma or serum sample from a woman pregnant with one or more fetuses. The two fractional contributions can be used to identify a portion of the fetal genome. For example, a separation value between the two fractional contributions of fetal tissue can indicate the fetal genotype at a locus and can indicate which of the two parental haplotypes is inherited by the fetus. For instance, the higher fractional contribution can indicate the inherited haplotype, and both can be inherited if the separation value is less than a threshold; both haplotypes could be inherited when both parents share the haplotype (or allele for a genotype) for the region being analyzed.

In some embodiments, only one fractional contribution of fetal tissue is determined for one haplotype. When the one fractional contribution exceeds a reference value (e.g., as determined from other samples), the fetus can be determined to have inherited the one haplotype for the region being analyzed.

In some embodiments, two methylation levels can be determined for two sets of cell-free DNA molecules from a maternal sample, each set being for a different one of two parental haplotypes of a parent of a fetus, as part of identifying a portion of the fetal genome. The two methylation levels can be compared to each other to identify which haplotype is inherited by the fetus, e.g., by which methylation level is lower. For example, a fetus contributes cell-free DNA molecules that are hypomethylated, and a measurement of a lower methylation level of one haplotype indicates that the one haplotype is inherited by the fetus.

In some embodiments, a sequence imbalance can be detected for a target chromosomal region of a fetus using a mixture of cell-free DNA molecules from a plurality of tissues types. Target heterozygous loci can be identified for the target chromosomal region having a first target haplotype and a second target haplotype having different alleles. A first target fractional contribution of the fetal tissue type in the mixture can be determined using methylation levels at the target heterozygous loci, where the methylation levels are determined using a target set of cell-free DNA molecules located at (i.e., covering) the loci of the first haplotype. Similarly, a first reference fractional contribution of the fetal tissue type can be determined. A separation value of the first target fractional contribution and the first reference fractional contribution can be compared to a threshold value to determine whether the fetus has a sequence imbalance. If the two fractional contributions are significantly different, then a sequence imbalance can be determined. The specific threshold being used can depend on the specific sequence imbalance (e.g., an amplification or a deletion) being tested.

In some embodiments, a fractional contribution of a first haplotype in a first tissue type can be used to determine whether the first tissue type has a disease state. The first haplotype can have a signature specific to healthy cells or to abnormal cells. Thus, the first haplotype can be not present in healthy cells of the organism, or present in healthy cells of the organism and not present in abnormal cells that may be in the mixture. A separation value between the first fractional contribution and a reference fractional contribution can be compared to a threshold value to determine a classification of whether the first tissue type has a disease state.

In some embodiments, the tissue origin of a copy number aberration can be determined using methylation deconvolution. A first chromosomal region can be identified as exhibiting a copy number aberration. The haplotypes in the first chromosomal region can be determined. For each of M tissue types, a corresponding separation value between the corresponding first fractional contribution and the corresponding second fractional contribution can be determined. The tissue type with the highest separation value can be identified as the tissue of origin.

Other embodiments are directed to systems and computer readable media associated with methods described herein.

A better understanding of the nature and advantages of embodiments of the present invention may be gained with reference to the following detailed description and the accompanying drawings.

BRIEF DESCRIPTION OF THE DRAWINGS

FIG. 4 shows a table of percentage contributions determined from a plasma DNA tissue mapping analysis among pregnant women according to embodiments of the present invention.

FIG. 6 shows a table of percentage contributions from plasma DNA tissue mapping analysis among the non-pregnant healthy control subjects according to embodiments of the present invention.

FIG. 7 shows a table of the estimated contributions of different organs to the plasma DNA for 11 pregnant women and 4 non-pregnant healthy subjects using the first set of markers (with high organ specificity) according to embodiments of the present invention.

FIG. 8 shows a table of the estimated contributions of different organs to the plasma DNA for 11 pregnant women and 4 non-pregnant healthy subjects using the second set of markers (with low organ specificity) according to embodiments of the present invention.

FIG. 16 shows chromosomal aneuploidy detection based on haplotype deconvolution for paternal haplotypes according to embodiments of the present invention.

TERMS

Figure 1:
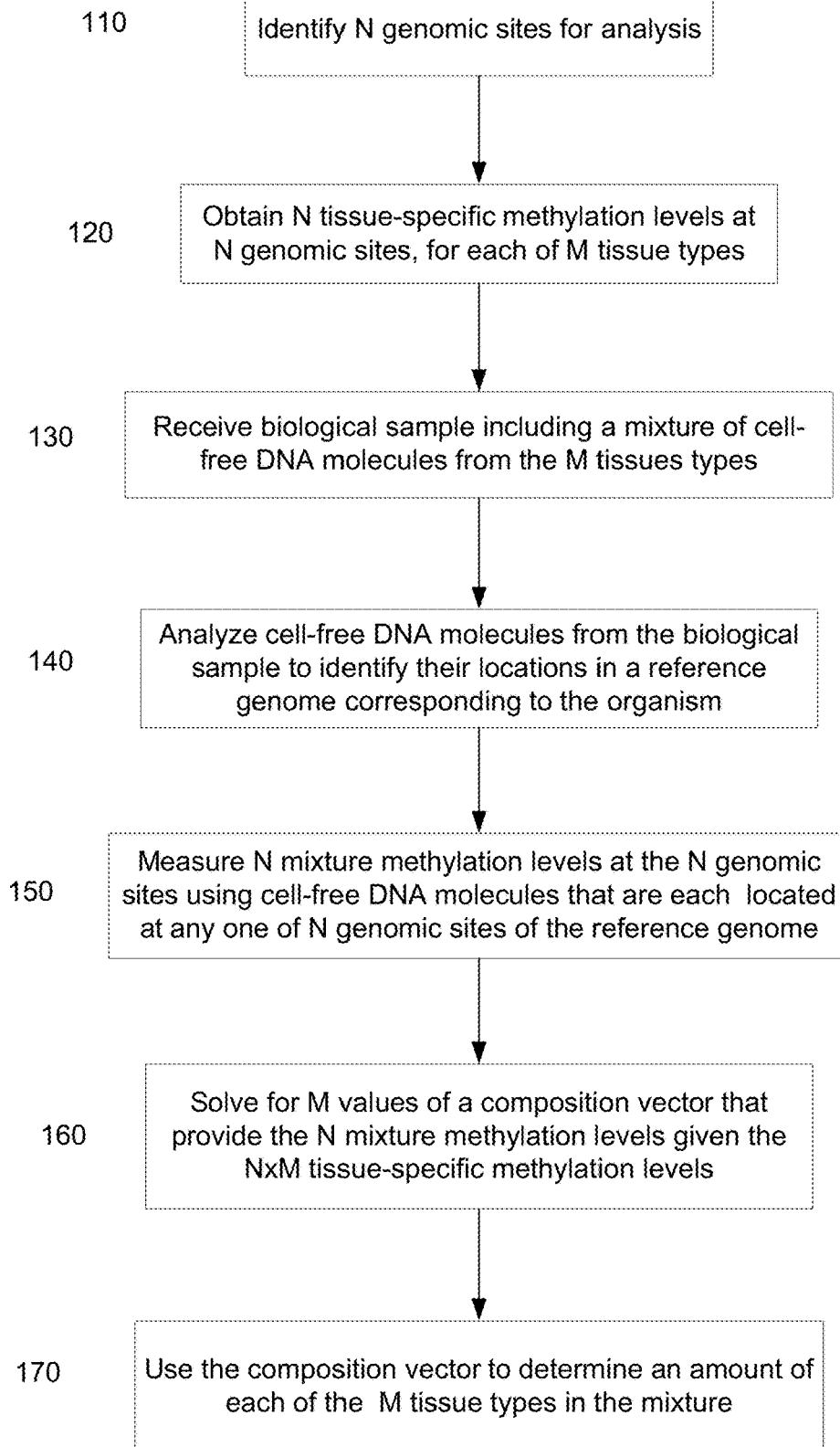
FIG. 1 is a flowchart illustrating a method of analyzing a DNA mixture of cell-free DNA molecules to determine fractional contributions from various tissue types from methylation levels according to embodiments of the present invention.

A "methylome" provides a measure of an amount of DNA methylation at a plurality of sites or loci in a genome. The methylome may correspond to all of the genome, a substantial part of the genome, or relatively small portion(s) of the genome. Examples of methylomes of interest are the methylomes of organs (e.g. methylomes of brain cells, bones, the lungs, the heart, the muscles and the kidneys, etc.) that can contribute DNA into a bodily fluid (e.g. plasma, serum, sweat, saliva, urine, genital secretions, semen, stools fluid, diarrheal fluid, cerebrospinal fluid, secretions of the gastrointestinal tract, ascitic fluid, pleural fluid, intraocular fluid, fluid from a hydrocele (e.g. of the testis), fluid from a cyst, pancreatic secretions, intestinal secretions, sputum, tears, aspiration fluids from breast and thyroid, etc.). The organs may be transplanted organs. The methylome of a fetus is another example.

A "plasma methylome" is a methylome determined from the plasma or serum of an animal (e.g., a human). The plasma methylome is an example of a cell-free methylome since plasma and serum include cell-free DNA. The plasma methylome is also an example of a mixed methylome since it is a mixture of fetal/maternal methylome or tumor/patient methylome or DNA derived from different tissues or organs or donor/recipient methylome in the context or organ transplantation.

A "site" (also called a "genomic site") corresponds to a single site, which may be a single base position or a group of correlated base positions, e.g., a CpG site or larger group of correlated base positions. A "locus" may correspond to a region that includes multiple sites. A locus can include just one site, which would make the locus equivalent to a site in that context.

The "methylation index" for each genomic site (e.g., a CpG site) can refer to the proportion of DNA fragments (e.g., as determined from sequence reads or probes) showing methylation at the site over the total number of reads covering that site. A "read" can correspond to information (e.g., methylation status at a site) obtained from a DNA fragment. A read can be obtained using reagents (e.g. primers or probes) that preferentially hybridize to DNA fragments of a particular methylation status. Typically, such reagents are applied after treatment with a process that differentially modifies or differentially recognizes DNA molecules depending of their methylation status, e.g. bisulfite conversion, or methylation-sensitive restriction enzyme, or methylation binding proteins, or anti-methylcytosine antibodies, or single molecule sequencing techniques that recognize methylcytosines and hydroxymethylcytosines.

The "methylation density" of a region can refer to the number of reads at sites within the region showing methylation divided by the total number of reads covering the sites in the region. The sites may have specific characteristics, e.g., being CpG sites. Thus, the "CpG methylation density" of a region can refer to the number of reads showing CpG methylation divided by the total number of reads covering CpG sites in the region (e.g., a particular CpG site, CpG sites within a CpG island, or a larger region). For example, the methylation density for each 100-kb bin in the human genome can be determined from the total number of cytosines not converted after bisulfite treatment (which corresponds to methylated cytosine) at CpG sites as a proportion of all CpG sites covered by sequence reads mapped to the 100-kb region. This analysis can also be performed for other bin sizes, e.g. 500 bp, 5 kb, 10 kb, 50-kb or 1-Mb, etc. A region could be the entire genome or a chromosome or part of a chromosome (e.g. a chromosomal arm). The methylation index of a CpG site is the same as the methylation density for a region when the region only includes that CpG site. The "proportion of methylated cytosines" can refer the number of cytosine sites, "C's", that are shown to be methylated (for example unconverted after bisulfite conversion) over the total number of analyzed cytosine residues, i.e. including cytosines outside of the CpG context, in the region. The methylation index, methylation density and proportion of methylated cytosines are examples of "methylation levels." Apart from bisulfite conversion, other processes known to those skilled in the art can be used to interrogate the methylation status of DNA molecules, including, but not limited to enzymes sensitive to the methylation status (e.g. methylation-sensitive restriction enzymes), methylation binding proteins, single molecule sequencing using a platform sensitive to the methylation status (e.g. nanopore sequencing (Schreiber et al. Proc Natl Acad Sci 2013; 110: 18910-18915) and by the Pacific Biosciences single molecule real time analysis (Flusberg et al. Nat Methods 2010; 7: 461-465)).

A "methylation profile" (also called methylation status) includes information related to DNA methylation for a region. Information related to DNA methylation can include, but not limited to, a methylation index of a CpG site, a methylation density of CpG sites in a region, a distribution of CpG sites over a contiguous region, a pattern or level of methylation for each individual CpG site within a region that contains more than one CpG site, and non-CpG methylation. A methylation profile of a substantial part of the genome can be considered equivalent to the methylome. "DNA methylation" in mammalian genomes typically refers to the addition of a methyl group to the 5' carbon of cytosine residues (i.e. 5-methylcytosines) among CpG dinucleotides. DNA methylation may occur in cytosines in other contexts, for example CHG and CHH, where H is adenine, cytosine or thymine. Cytosine methylation may also be in the form of 5-hydroxymethylcytosine. Non-cytosine methylation, such as $N^6$-methyladenine, has also been reported.

"Methylation-aware sequencing" refers to any sequencing method that allows one to ascertain the methylation status of a DNA molecule during a sequencing process, including, but not limited to bisulfite sequencing, or sequencing preceded by methylation-sensitive restriction enzyme digestion, immunoprecipitation using anti-methylcytosine antibody or methylation binding protein, or single molecule sequencing that allows elucidation of the methylation status.

A "tissue" corresponds to a group of cells that group together as a functional unit. More than one type of cells can be found in a single tissue. Different types of tissue may consist of different types of cells (e.g., hepatocytes, alveolar cells or blood cells), but also may correspond to tissue from different organisms (mother vs. fetus) or to healthy cells vs. tumor cells. "Reference tissues" correspond to tissues used to determine tissue-specific methylation levels. Multiple samples of a same tissue type from different individuals may be used to determine a tissue-specific methylation level for that tissue type.

A "biological sample" refers to any sample that is taken from a subject (e.g., a human, such as a pregnant woman, a person with cancer, or a person suspected of having cancer, an organ transplant recipient or a subject suspected of having a disease process involving an organ (e.g., the heart in myocardial infarction, or the brain in stroke, or the hematopoietic system in anemia) and contains one or more nucleic acid molecule(s) of interest. The biological sample can be a bodily fluid, such as blood, plasma, serum, urine, vaginal fluid, fluid from a hydrocele (e.g. of the testis), or vaginal flushing fluids, pleural fluid, ascitic fluid, cerebrospinal fluid, saliva, sweat, tears, sputum, bronchoalveolar lavage fluid, etc. Stool samples can also be used. In various embodiments, the majority of DNA in a biological sample that has been enriched for cell-free DNA (e.g., a plasma sample obtained via a centrifugation protocol) can be cell-free (as opposed to cells), e.g., greater than 50%, 60%, 70%, 80%, 90%, 95%, or 99%. The centrifugation protocol can include 3,000 g×10 minutes, obtaining the fluid part, and recentrifuging at 30,000 g for another 10 minutes to remove residual cells.

The term "level of cancer" can refer to whether cancer exists (i.e., presence or absence), a stage of a cancer, a size of tumor, whether there is metastasis, the total tumor burden of the body, and/or other measure of a severity of a cancer (e.g. recurrence of cancer). The level of cancer could be a number or other indicia, such as symbols, alphabet letters, and colors. The level could be zero. The level of cancer also includes premalignant or precancerous conditions (states) associated with mutations or a number of mutations. The level of cancer can be used in various ways. For example, screening can check if cancer is present in someone who is not known previously to have cancer. Assessment can investigate someone who has been diagnosed with cancer to monitor the progress of cancer over time, study the effectiveness of therapies or to determine the prognosis. In one embodiment, the prognosis can be expressed as the chance of a patient dying of cancer, or the chance of the cancer progressing after a specific duration or time, or the chance of cancer metastasizing. Detection can mean 'screening' or can mean checking if someone, with suggestive features of cancer (e.g. symptoms or other positive tests), has cancer.

The term "sequence imbalance" of a chromosomal region can refer to any significant deviation in an amount of cell-free DNA molecules from the chromosomal region relative to an expected value, if the organism was healthy. For example, a chromosomal region may exhibit an amplification or a deletion in a certain tissue, thereby resulting in a sequence imbalance for the chromosomal region in a DNA mixture containing DNA from the tissue, mixed with DNA from other tissues. As examples, the expected value can be obtained from another sample or from another chromosomal region that is assumed to be normal (e.g., an amount representative of two copies for a diploid organism). A chromosomal region can be composed of multiple disjoint subregions.

A "type" for a genomic locus (marker) corresponds to specific attributes for a locus across tissue types. The description primarily refers to type I loci and type II loci, whose properties are provided in detail below. A locus of a given type can have specific statistical variation in methylation levels across tissue types. A "category" for a genomic locus (marker) corresponds to specific variation in methylation levels for a locus across different individuals for a same tissue type. A set of genomic loci (markers) can be composed of any number of loci of various types and/or categories. Thus, a set of loci corresponds to loci selected for a particular measurement and does not connote any particular properties of the loci in the set.

A "separation value" corresponds to a difference or a ratio involving two values, e.g., two fractional contributions or two methylation levels. The separation value could be a simple difference or ratio. The separation value can include other factors, e.g., multiplicative factors. As other examples, a difference or ratio of functions of the values can be used, e.g., a difference or ratio of the natural logarithms (ln) of the two values. A separation value can include a difference and a ratio.

The term "classification" as used herein refers to any number(s) or other characters(s) that are associated with a particular property of a sample. For example, a "+" symbol (or the word "positive") could signify that a sample is classified as having deletions or amplifications. The classification can be binary (e.g., positive or negative) or have more levels of classification (e.g., a scale from 1 to 10 or 0 to 1). The term "cutoff" and "threshold" refer to a predetermined number used in an operation. A threshold value may be a value above or below which a particular classification applies. Either of these terms can be used in either of these contexts.

DETAILED DESCRIPTION

Methylation differences among tissue types (e.g., fetal tissues, liver etc.) in a DNA mixture (e.g., plasma) may be used to differentiate properties of haplotypes in a specific tissue type. For example, the methylation levels of two maternal haplotypes in the plasma of a pregnant woman can be used to determine which haplotype is inherited from the mother to the fetus. As another example, the methylation levels of two haplotypes in fetal tissue can be used to detect a sequence imbalance (e.g., an aneuploidy) in the fetus. Other tissue types may also be analyzed, e.g., to detect a disease state in a specific tissue type. The tissue type from which a copy number aberration originates may also be determined.

Some embodiments can determine percentages of cell-free DNA in plasma (or other DNA mixture) from various tissue types using known methylation levels at certain genomic sites for the specific tissue types. For example, methylation levels at the genomic sites can be measured for a liver sample, and these tissue-specific methylation levels can be used to determine how much cell-free DNA in the mixture is from the liver. Methylation levels can be measured for tissue types that provide substantial contributions to the DNA mixture, so that a predominance (e.g., more than 90%, 95%, or 99%) of the cell-free DNA mixture can be accounted for. Such other samples can include, but not limited to, some or all of the following: lung, colon, small intestines, pancreas, adrenal glands, esophagus, adipose tissues, heart, and brain.

A deconvolution process can be used to determine fractional contributions (e.g., percentage) for each of the tissue types for which tissue-specific methylation levels are known. In some embodiments, a linear system of equations can be created from the known tissue-specific methylation levels and the mixture methylation levels at the specified genomic sites, and the fractional contributions that best approximate the measured mixture methylation levels can be determined (e.g., using least squares).

Once the fractional contributions are determined, the fractional contributions can be used for various purposes. For example, differences in fractional contributions of fetal tissue can be used to determine which haplotype is inherited from a parent. The alleles at one or more heterozygous loci can be determined for each of two parental haplotypes. Cell-free DNA at the one or more heterozygous loci can be used to determine two fractional contributions: one for each haplotype. For example, cell-free DNA molecules having alleles of a first haplotype can be used to determine a first fractional contribution, and cell-free DNA molecules having alleles of a second haplotype can be used to determine a second fractional contribution. The inherited haplotype will correspond to the higher fractional contribution for fetal tissue.

Further, an inherited haplotype will have lower methylation levels due to the general hypomethylation of fetal cell-free DNA. The methylation levels for the two haplotypes can be compared, and the haplotype with lower methylation level can be identified as being the inherited haplotype.

As another example, a sequence imbalance can be detected in a target chromosomal region of a fetus. A target fractional contribution of the fetal tissue type in the mixture can be determined for a first haplotype in the target chromosomal region. Similarly, a reference fractional contribution of the fetal tissue type can be determined for a reference chromosomal region. A separation value between the two contributions can be compared to a threshold value to determine whether the fetus has a sequence imbalance (e.g., an aneuploidy).

As another example, a first haplotype can have a signature specific to healthy cells or to abnormal cells. A separation value between the fractional contribution determined for the first haplotype and a reference fractional contribution can be compared to a threshold value to determine a classification of whether the first tissue type has a disease state. As examples, the first haplotype can be of a transplanted organ or a tumor, or only be in healthy cells and not in a transplanted organ or a tumor. The disease state may be whether the transplanted organ is being rejected, or whether a tumor is increasing in size or metastasized (e.g., after a surgery did not remove all of the tumor).

As another example, the tissue origin of a copy number aberration can be determined using methylation deconvolution. A first chromosomal region can be identified as exhibiting a copy number aberration. For each of M tissue types, a corresponding separation value between the fractional contributions of the two haplotypes in the first chromosomal region can be determined. The tissue type with the highest separation value can be identified as the tissue of origin.

Methylation deconvolution is first described, and then the selection of methylation markers and the accuracy of the methylation deconvolution are described. The use of the fractional contributions to determine part of a fetal genome is then described.

I. Composition of DNA Mixture by Methylation Deconvolution

Different tissue types can have different levels of methylation for a genomic site. These differences can be used to determine the fractional contributions of DNA from the various tissue types in a mixture. Thus, the composition of a DNA mixture can be determined by a tissue-specific methylation pattern analysis. The examples below discuss methylation densities, but other methylation levels can be used.

A. Single Genomic Site

The principle of methylation deconvolution can be illustrated using a single methylation genomic site (methylation marker) to determine a composition of a DNA mixture from an organism. Assume that tissue A is completely methylated for the genomic site, i.e. methylation density (MD) of 100% and tissue B is completely unmethylated, i.e. MD of 0%. In this example, methylation density refers to the percentage of cytosine residues with the context of CpG dinucleotides being methylated in the region of interest.

If the DNA mixture C is composed of tissue A and tissue B and the overall methylation density of the DNA mixture C is 60%, we can deduce the proportional contribution of tissues A and B to the DNA mixture C according to the following formula:

$$MD_C = MD_A \times a + MD_B \times b,$$

where $MD_A$, $MD_B$, $MD_C$ represent the MD of tissues A, tissue B and the DNA mixture C, respectively; and a and b are the proportional contributions of tissues A and B to the DNA mixture C. In this particular example, it is assumed that tissues A and B are the only two constituents of the DNA mixture. Therefore, a+b=100%. Thus, it is calculated that tissues A and B contribute 60% and 40%, respectively, to the DNA mixture.

The methylation densities in tissue A and tissue B can be obtained from samples of the organism or from samples from other organisms of the same type (e.g., other humans, potentially of a same subpopulation). If samples from other organisms are used, a statistical analysis (e.g., average, median, geometric mean) of the methylation densities of the samples of tissue A can be used to obtain the methylation density $MD_A$, and similarly for $MD_B$.

Genomic site can be chosen to have minimal inter-individual variation, for example, less than a specific absolute amount of variation or being within a lowest portion of genomic sites tested. For instance, for the lowest portion, embodiments can select only genomic sites having the lowest 10% of variation among a group of genomic sites tested. The other organisms can be taken from healthy persons, as well as those with particular physiologic conditions (e.g. pregnant women, or people with different ages or people of a particular sex), which may correspond to a particular subpopulation that includes the current organism being tested.

The other organisms of a subpopulation may also have other pathologic conditions (e.g. patients with hepatitis or diabetes, etc.). Such a subpopulation may have altered tissue-specific methylation patterns for various tissues. The methylation pattern of the tissue under such disease condition can be used for the deconvolution analysis in addition to using the methylation pattern of the normal tissue. This deconvolution analysis may be more accurate when testing an organism from such a subpopulation with those conditions. For example, a cirrhotic liver or a fibrotic kidney may have a different methylation pattern compared with a normal liver and normal kidney, respectively. Thus, if a patient with liver cirrhosis was screened for other diseases, it can be more accurate to include a cirrhotic liver as one of the candidates contributing DNA to the plasma DNA, together with the healthy tissues of other tissue types.

B. Multiple Genomic Sites

More genomic sites (e.g., 10 or more) may be used to determine the constitution of the DNA mixture when there are more potential candidate tissues. The accuracy of the estimation of the proportional composition of the DNA mixture is dependent on a number of factors including the number of genomic sites, the specificity of the genomic sites (also called "sites") to the specific tissues, and the variability of the sites across different candidate tissues and across different individuals used to determine the reference tissue-specific levels. The specificity of a site to a tissue refers to the difference in the methylation density of the genomic sites between the particular tissue and other tissue types.

The larger the difference between their methylation densities, the more specific the site to the particular tissue would be. For example, if a site is completely methylated in the liver (methylation density=100%) and is completely unmethylated in all other tissues (methylation density=0%), this site would be highly specific for the liver. Whereas, the variability of a site across different tissues can be reflected by, for example, but not limited to, the range or standard deviation of methylation densities of the site in different types of tissue. A larger range or higher standard deviation would allow a more precise and accurate determination of the relative contributions of the different organs to the DNA mixture mathematically. The effects of these factors on the accuracy of estimating the proportional contribution of the candidate tissues to the DNA mixture are illustrated in the later sections of this application.

Here, we use mathematical equations to illustrate the deduction of the proportional contribution of different organs to the DNA mixture. The mathematical relationship between the methylation densities of the different sites in the DNA mixture and the methylation densities of the corresponding sites in different tissues can be expressed as:

$$\overline{MD}_i = \Sigma_k (p_k \times MD_{ik}),$$

where $\overline{MD}_i$ represents the methylation density of the site i in the DNA mixture; $p_k$ represents the proportional contribution of tissue k to the DNA mixture; $MD_{ik}$ represents the methylation density of the site i in the tissue k. When the number of sites is the same or larger than the number of organs, the values of individual $p_k$ can be determined. The tissue-specific methylation densities can be obtained from other individuals, and the sites can be chosen to have minimal inter-individual variation, as mentioned above.

Additional criteria can be included in the algorithm to improve the accuracy. For example, the aggregated contribution of all tissues can be constrained to be 100%, i.e.

$$\Sigma_k p_k = 100\%.$$

Furthermore, all the organs' contributions can be required to be non-negative:

$$p_k \geq 0, \forall k$$

Due to biological variations, the observed overall methylation pattern may not be completely identical to the methylation pattern deduced from the methylation of the tissues. In such a circumstance, mathematical analysis would be required to determine the most likely proportional contribution of the individual tissues. In this regard, the difference between the observed methylation pattern in the DNA and the deduced methylation pattern from the tissues is denoted by W.

$$W = O - \sum_k (p_k \times M_k)$$

where O is the observed methylation pattern for the DNA mixture and $M_k$ is the methylation pattern of the individual tissue k. $p_k$ is the proportional contribution of tissue k to the DNA mixture. The most likely value of each $p_k$ can be determined by minimizing W, which is the difference between the observed and deduced methylation patterns. This equation can be resolved using mathematical algorithms, for example by, but not limited to, using quadratic programming, linear/non-linear regression, expectation-maximization (EM) algorithm, maximum likelihood algorithm, maximum a posteriori estimation, and the least squares method.

C. Method of Methylation Deconvolution

As described above, a biological sample including a mixture of cell-free DNA molecules from an organism can be analyzed to determine the composition of the mixture, specifically the contributions from different tissue types. For example, the percentage contribution of the cell-free DNA molecules from the liver can be determined. These measurements of the percentage contributions in the biological sample can be used to make other measurements of the biological sample, e.g., identifications of where a tumor is located, as is described in later sections.

FIG. 1 is a flowchart illustrating a method 100 of analyzing a DNA mixture of cell-free DNA molecules to determine fractional contributions from various tissue types from methylation levels according to embodiments of the present invention. A biological sample includes a mixture of cell-free DNA molecules from M tissues types. The biological sample can be any one of various examples, e.g., as mentioned herein. The number M of tissue types is greater than two. In various embodiments, M can be 3, 7, 10, 20, or more, or any number in between. Method 100 can be performed at least partially using a computer system, as can other methods described herein.

At block 110, N genomic sites are identified for analysis. The N genomic sites can have various attributes, e.g., as described in more detail in section II, which describes type I and type II genomic sites. As examples, the N genomic sites can include type I or type II sites only, or a combination of both. The genomic sites can be identified based on analyses of one or more other samples, e.g., based on data obtained from databases about methylation levels measured in various individuals.

Specific genomic sites can be selected to provide a desired level of accuracy. For example, loci that have at least a threshold variability can be used, as opposed to just using loci that are specific to one tissue type. A first set (e.g., 10) of the genomic sites can be selected such that each have a coefficient of variation of methylation levels of at least 0.15 across M tissue types and such that each has a difference between a maximum and a minimum methylation level for the M tissue types that exceeds 0.1 for one or more other samples. This first set of genomic sites may not have a specific methylation signature for a specific tissue type, e.g., only or predominantly methylated in the specific tissue type. Such a first set is referred to as type II sites. These genomic sites can be used in combination with genomic sites that do have a specific signature, which are referred to as type I sites.

Using the type II sites can ensure that the full space of methylation levels across the tissue types is spanned by the genomic sites, thereby providing increased accuracy over the type I sites. Just using more type I sites provides redundant basis vectors for the methylation space (i.e., more genomic sites that have the same pattern as other sites), while adding other genomic sites whose methylation levels have various values across different tissues adds new basis vectors for discriminating fractional contributions via the linear system of equations.

In some embodiments, at least 10 of the N genomic sites each have a coefficient of variation of methylation levels of at least 0.15 across the M tissue types. The at least 10 genomic sites can also each have a difference between a maximum and a minimum methylation level for the M tissue types that exceeds 0.1. These methylation properties of the genomic loci can be measured for one sample or a set of samples. The set of samples may be for a subpopulation of organisms that includes the instant organism being tested, e.g., a subpopulation having a particular trait that is shared with the instant organism. These other samples can be referred to as reference tissues, and different reference tissues may be used from different samples.

At block 120, N tissue-specific methylation levels are obtained at the N genomic sites for each of M tissue types. N is greater than or equal to M, so that the tissue-specific methylation levels can be used in the deconvolution to determine the fractional percentages. The tissue-specific methylation levels can form a matrix A of dimensions N by M. Each column of the matrix A can correspond to a methylation pattern for a particular tissue type, where the pattern is of methylation levels at the N genomic sites.

In various embodiments, the tissue-specific methylation patterns can be retrieved from public database(s) or previous studies. In examples herein, the methylation data for neutrophils and B cells were downloaded from the Gene Expression Omnibus (Hodges et al. Mol Cell 2011; 44:17-28). Methylation patterns for other tissues (hippocampus, liver, lung, pancreas, atrium, colon (including its various parts, e.g. sigmoid colon, transverse colon, ascending colon, descending colon), adrenal gland, esophagus, small intestines and CD4 T cell) were downloaded from the RoadMap Epigenomics project (Ziller et al. Nature 2013; 500:477-81). The methylation patterns for the buffy coat, placenta, tumor and plasma data were from published reports (Lun et al. Clin Chem. 2013; 59:1583-94; Chan et al. Proc Natl Acad Sci USA. 2013; 110:18761-8). These tissue-specific methylation patterns can be used to identify the N genomic sites to be used in the deconvolution analysis.

At block 130, the biological sample including a mixture of cell-free DNA molecules from the M tissues types is received. The biological sample may be obtained from the patient organism in a variety of ways. The manner of obtaining such samples may be non-invasive or invasive. Examples of non-invasively obtained samples include certain types of fluids (e.g. plasma or serum or urine) or stools. For instance, plasma includes cell-free DNA molecules from many organ tissues, and is thus useful for analyzing many organs via one sample.

At block 140, cell-free DNA molecules from the biological sample are analyzed to identify their locations in a reference genome corresponding to the organism. For example, the cell-free DNA molecules can be sequenced to obtain sequence reads, and the sequence reads can be mapped (aligned) to the reference genome. If the organism was a human, then the reference genome would be a reference human genome, potentially from a particular subpopulation. As another example, the cell-free DNA molecules can be analyzed with different probes (e.g., following PCR or other amplification), where each probe corresponds to a genomic location, which may cover a heterozygous and one or more CpG sites, as is described below.

A statistically significant number of cell-free DNA molecules can be analyzed so as to provide an accurate deconvolution for determining the fractional contributions from the M tissue types. In some embodiments, at least 1,000 cell-free DNA molecules are analyzed. In other embodiments, at least 10,000 or 50,000 or 100,000 or 500,000 or 1,000,000 or 5,000,000 cell-free DNA molecules or more can be analyzed. The total number of molecules to analyze can depend on M and N, and the desired precision (accuracy). In various examples, the total number of cell-free DNA analyzes can be less than 500,000, one million, two million, five million, ten million, 20 million, or 50 million.

At block 150, N mixture methylation levels are measured at the N genomic sites using cell-free DNA molecules that are each located at any one of N genomic sites of the reference genome. A DNA molecule can be identified as located at a genomic site or a locus by one or more bases of the DNA molecule corresponding to one or more base positions of the genomic site or locus. Thus, the sequence of the DNA molecule would cover one or more base positions of the genomic site or locus. This information can be determined based on the locations determined in block 140. Such an identification of a DNA molecule located at a site of a locus can be used for any similar block of methods described herein.

The N mixture methylation levels refer to methylation levels in the mixture of the biological sample. As an example, if a cell-free DNA molecule from the mixture is located at one of the N genomic sites, then a methylation index for that molecule at the site can be included in an overall methylation density for that site. The N mixture methylation levels can form a methylation vector b of length N, where b corresponds to observed values from which the fractional contribution of each corresponding tissue type can be determined.

In one embodiment, the methylation levels for the genomic sites in the DNA mixture can be determined using whole genome bisulfite sequencing. In other embodiments, the methylation levels for the CpG sites can be determined using methylation microarray analysis, such as the Illumina HumanMethylation450 system, or by using methylation immunoprecipitation (e.g. using an anti-methylcytosine antibody) or treatment with a methylation-binding protein followed by microarray analysis or DNA sequencing, or by using methylation-sensitive restriction enzyme treatment followed by microarray or DNA sequencing, or by using methylation aware sequencing e.g. using a single molecule sequencing method (e.g. by a nanopore sequencing (Schreiber et al. Proc Natl Acad Sci 2013; 110: 18910-18915) or by the Pacific Biosciences single molecule real time analysis (Flusberg et al. Nat Methods 2010; 7: 461-465)). Tissue-specific methylation levels can be measured in a same way. In yet other embodiments, other methods, for example, but not limited to targeted bisulfite sequencing, methylation-specific PCR, non-bisulfite based methylation-aware sequencing (e.g. by single molecule sequencing platforms (Powers et al. Efficient and accurate whole genome assembly and methylome profiling of *E. coli*. BMC Genomics. 2013; 14:675)) can be used for the analysis of the methylation level of the plasma DNA for plasma DNA methylation deconvolution analysis.

At block 160, M values of a composition vector are determined. Each M value corresponds to a fractional contribution of a particular tissue type of the M tissue types to the DNA mixture. The M values of the composition vector can be solved to provide the N mixture methylation levels (e.g., methylation vector b) given the matrix A composed of N×M tissue-specific methylation levels (i.e. N tissue-specific methylation levels for each of the M tissue types). The M fractional contributions can correspond to a vector x that is determined by solving Ax=b. When N is greater than M, the solution can involve a minimization of errors, e.g., using least-squares.

At block 170, the composition vector is used determine an amount of each of the M tissue types in the mixture. The M values of the composition vector may be taken directly as the fractional contributions of the M tissue types. In some implementations, the M values can be converted to percentages. Error terms can be used to shift the M values to higher or lower values.

D. Applications

As mentioned above, the fractional contributions can be used in further measurements of the biological sample and other determinations, e.g., whether a particular chromosomal region has a sequence imbalance, whether a particular tissue type is diseased, and to determine which haplotype of two parental haplotypes is inherited by the fetus of a pregnant female from which the sample was obtained.

Figure 2:
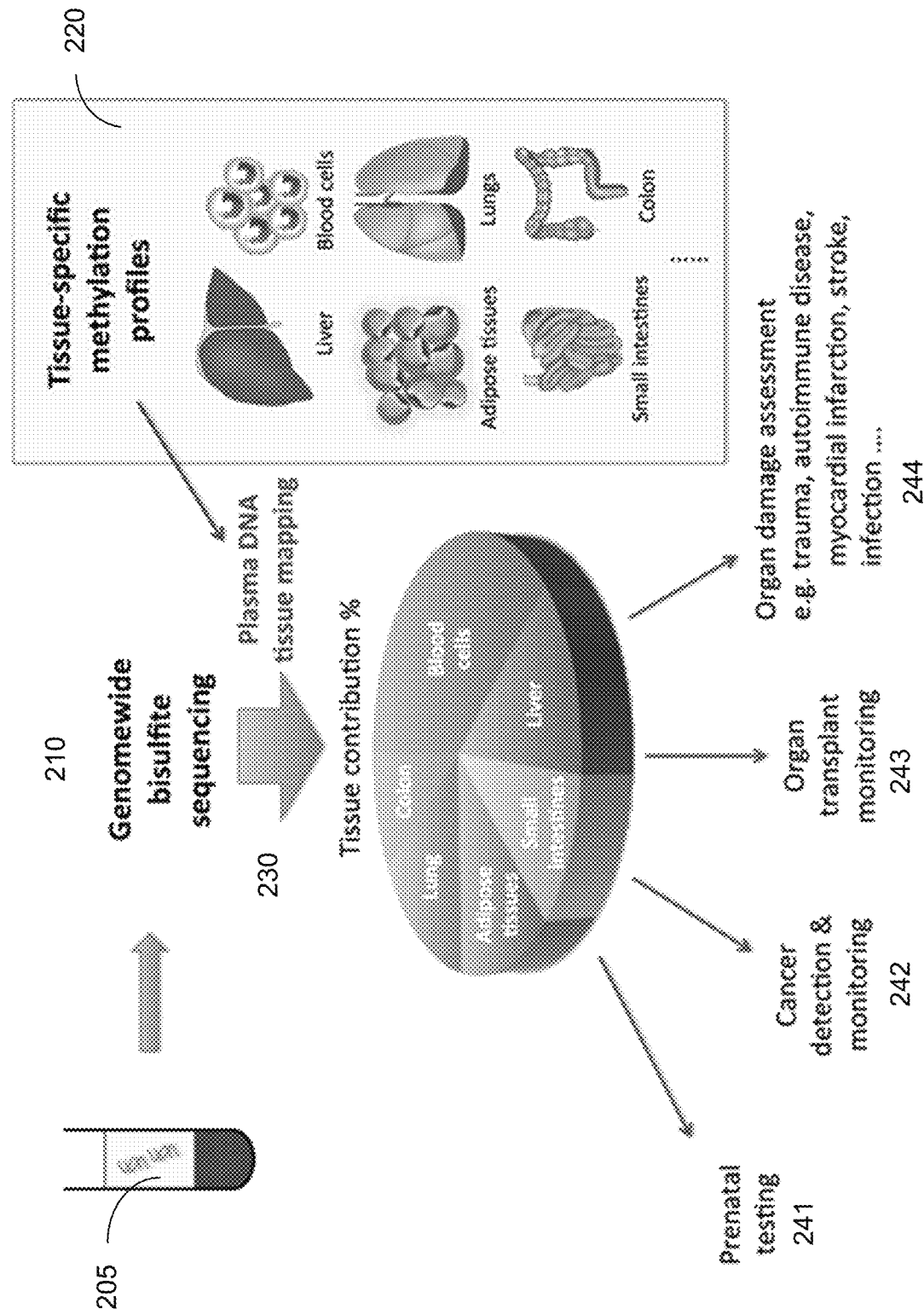
FIG. 2 shows a schematic diagram showing several potential applications of DNA methylation deconvolution (e.g., using plasma) and its applications according to embodiments of the present invention.

FIG. 2 shows a schematic diagram showing several potential applications of DNA methylation deconvolution (e.g., using plasma) according to embodiments of the present invention. In FIG. 2, a biological sample 205 is subjected to genome-wide bisulfite sequencing at 210. At 230, plasma DNA tissue mapping uses tissue-specific methylation profiles 220 to determine tissue contribution percentages. Example tissue-specific methylation profiles are shown as liver, blood cells, adipose tissues, lungs, small intestines, and colon. The contribution percentages can be determined as described above and elsewhere, e.g., solving Ax=b. Examples of applications include prenatal testing 241, cancer detection and monitoring 242, organ transplant monitoring, and organ damage assessment 244.

A list of methylation markers (genomic sites) that are useful for determining the contributions of different organs to the plasma DNA can be identified by comparing the methylation profiles (FIG. 2) of different tissues, including the liver, lungs, esophagus, heart, pancreas, sigmoid colon, small intestines, adipose tissues, adrenal glands, colon, T cells, B cells, neutrophils, brain and placenta. In various examples, whole genome bisulfite sequencing data for the liver, lungs, esophagus, heart, pancreas, colon, small intestines, adipose tissues, adrenal glands, brain and T cells were retrieved from the Human Epigenome Atlas from the Baylor College of Medicine (www.genboree.org/epigenomeatlas/index.rhtml). The bisulfite sequencing data for B cells and neutrophils were from the publication by Hodges et al. (Hodges et al; Directional DNA methylation changes and complex intermediate states accompany lineage specificity in the adult hematopoietic compartment. Mol Cell 2011; 44: 17-28). The bisulfite sequencing data for the placenta were from Lun et al (Lun et al. Clin Chem 2013; 59:1583-94). In other embodiments, markers can be identified from datasets generated using microarray analyses, e.g. using the Illumina Infinium HumanMethylation450 BeadChip Array.

II. Selection of Methylation Markers

Above, we have described the principle of using methylation analysis to determine the composition of a DNA mixture. In particular, the percentage contribution of different organs (or tissues) to the plasma DNA can be determined using methylation analysis. In this section, we further describe the method for the selection of methylation markers and clinical applications of this technology.

The results of determining the composition of the DNA mixture by methylation analysis are affected by the methylation markers used for the deconvolution of the composition of the DNA mixture. Thus, the selection of appropriate genomic methylation markers can be important for the accurate determination of the constitution of the DNA mixture.

A. Criteria for a Methylation Marker for Deconvolution

For marker selection, the following three attributes may be considered. (i) It is desirable for a methylation marker to have a low variability in the methylation level measured in the same tissue type across different individuals. As the determination of the composition of the DNA mixture is dependent on the recognition of the tissue-specific methylation patterns, the low variability in methylation level in the same tissue type across different individuals would be useful for accurate identification of the tissue-specific patterns in the DNA mixture. In embodiments where the tissue-specific methylation levels are obtained from samples of other organisms (e.g., from a database), the low variability means that the methylation levels from the other samples are similar to the tissue-specific methylation levels for the current organism being tested.

(ii) It is desirable for a methylation marker to have a high variability in methylation levels across different tissues. For a particular marker, a higher difference in the methylation levels across different tissues can provide a more precise determination of the contribution of different tissues to the DNA mixture. In particular, an improvement in precision can be obtained by using one set of markers having attribute (ii) and another set of markers having attribute (iii).

(iii) It is desirable for a methylation marker to have a particularly different methylation level in a particular tissue when compared with those from most or all of the other tissues. In contrast to point (ii) above, a marker can have low variability in the methylation level of most tissues but its methylation level in one particular tissue is different from most of the other tissues. This marker would be particularly useful for the determination of the contribution of the tissue that has a different methylation level from other tissues.

B. Example

A principle of marker selection is illustrated in the following hypothetical examples in table 1.

TABLE 1

Methylation densities in different tissues for 6 hypothetical methylation markers.

| | Marker 1 | Marker 2 | Marker 3 | Marker 4 | Marker 5 | Marker 6 |
|---|---|---|---|---|---|---|
| Liver 1 | 20% | 69% | 9% | 9% | 10% | 90% |
| Liver 2 | 50% | 70% | 10% | 10% | 10% | 90% |
| Liver 3 | 90% | 71% | 11% | 11% | 10% | 90% |
| Heart | 20% | 20% | 30% | 13% | 12% | 12% |
| Lung | 30% | 30% | 60% | 17% | 14% | 84% |
| Colon | 40% | 40% | 90% | 20% | 80% | 80% |

In this hypothetical example, marker 2 has lower variability in methylation density in the liver from three individuals when compared with marker 1. Therefore, marker 2 is superior to marker 1 as a signature for determining the contribution of the liver in a DNA mixture.

Compared with marker 4, marker 3 has a higher variability in methylation density across different tissue types. The same level of change in the estimated contribution from the different tissues would provide a bigger change in the deduced methylation density of the DNA mixture for marker 3 than for marker 4 according to the mathematical relationship discussed above. Therefore, the estimation of the contribution of each tissue can be more precise with marker 3.

Marker 5 has a low variability in methylation density across the liver, heart and lung. Their methylation densities vary from 10% to 14%. However, the methylation density of colon is 80%. This marker would be particularly useful for determining the contribution of the colon in the DNA mixture. Similarly, the heart is hypomethylated compared with the other tissues for marker 6. Therefore, the contribution of the heart can be accurately determined by marker 6. Thus, the combination of markers 5 and 6 would be able to accurately determine the contributions of the colon and the heart. The addition of markers 2 and 3 would then be sufficient to deduce the contribution of each of the four organs, including the liver, heart, lung and colon.

C. Different Types of Markers

A methylation marker may not necessarily need to have all of the above three attributes. A type I methylation marker would typically have attribute (iii) above. A number of such markers may also have attribute (i). On the other hand, a type II methylation marker would typically have attribute (ii) above. A number of such markers may also have attribute (i). It is also possible that a particular marker may have all three attributes.

In some embodiments, markers are broadly divided into two types (type I and type II). Type I markers have tissue specificity. The methylation level of these markers for a particular group of one or more tissues is different from most of the other tissues. For example, a particular tissue can have a significant methylation level compared with the methylation level of all the other tissues. In another example, two tissues (e.g., tissue A and tissue B) have similar methylation levels, but the methylation levels of tissues A and B are significantly different from those of the remaining tissues.

Type II markers have a high inter-tissue methylation variability. The methylation levels of these markers are highly variable across different tissues. A single marker in this category may not be sufficient to determine the contribution of a particular tissue to the DNA mixture. However, a combination of type II markers, or in combination with one or more type I markers can be used collectively to deduce the contribution of individual tissues. Under the above definition, a particular marker can be a type I marker only, a type II marker only, or be simultaneously both a type I and type II marker.

1. Type I Markers

In one embodiment, a type I marker can be identified by comparing the methylation density of the marker with the mean and standard deviation (SD) of methylation densities of this particular marker for all candidate tissues. In one implementation, a marker is identified if its methylation density in one tissue is different from the mean of all the tissues by 3 standard deviations (SD).

The methylation profiles of 14 tissues obtained from sources mentioned above were studied to select markers. In one analysis, a total of 1,013 type I markers were identified (markers labeled type I in Table S1 of Appendix A of U.S. Provisional Application No. 62/158,466) using the above criteria. In other embodiments, other cutoffs between the particular tissues and the mean methylation densities can be used, for example, but not limited to 1.5 SD, 2 SD, 2.5 SD, 3.5 SD and 4 SD. In yet another embodiment, a type I marker can identified through the comparison of the methylation density of the particular tissue to the median methylation density of all tissues.

In other embodiments, the type I markers can be obtained when more than one tissue (for example, but not limited to two, three, four or five tissues) show significantly different methylation densities than the mean methylation density of all the candidate tissues. In one implementation, a cutoff methylation density can be calculated from the mean and SD of the methylation densities of all the candidate tissues. For illustration purpose, the cutoff can be defined as 3 SD higher or lower than the mean methylation densities. A marker is selected when the methylation densities of more than one (for example, but not limited to two, three, four, five, or more than five) tissues are more than 3 SD higher than the mean methylation density or more than 3 SD lower than the mean methylation density of the tissues.

2. Type II Markers

For identification of type II markers, the mean and SD of methylation densities across all 14 candidate tissues were calculated and the ratio of SD to the mean was denoted as the coefficient of variation (CV). In this illustrative example, we used a cutoff of >0.25 for the CV to identify the qualified type II markers, as well as the difference between the maximum and minimum methylation densities for the group of tissues exceeding 0.2. Using these criteria, 5820 type II markers were identified (markers labeled type II in Table S1 of Appendix A). In other embodiments, other cutoffs for the CV, for example but not limited to 0.15, 0.2, 0.3 and 0.4, can be used. In yet other embodiments, other cutoffs for the difference between the maximum and minimum methylation densities, for example, but not limited to 0.1, 0.15, 0.25, 0.3, 0.35, 0.4, 0.45 and 0.5, can be used.

In other embodiments, the average values across multiple samples of the same tissue type can be used to measure a variation of the methylation levels across different tissues. For example, 10 methylation levels of a same genomic site from 10 samples can be averaged to obtain a single methylation level for the genomic site. A similar process can be performed to determine average methylation levels for other tissue types for the genomic site. The average values across tissue types can then be used for determining whether the genomic site has significant variation across tissue types. Other statistical values can be used besides an average, e.g., a median or a geometric mean. Such statistical values can be used to identify type I and/or type II markers.

The different samples of a same tissue type (e.g., from different individuals) can be used to determine a variation of methylation levels across the different samples. Thus, if there are multiple samples of the same tissue type, embodiments can further measure the variation of a particular marker amongst such samples of the same tissue type. A marker with a low variation across samples would be a more reliable marker than one with a high variation. Further details of markers and deconvolution can be found in commonly-owned U.S. Patent Publication 2016/0017419, entitled "Methylation Pattern Analysis Of Tissues In A DNA Mixture," by Chiu et al., and PCT Publication WO2014/043763 entitled "Non-Invasive Determination Of Methylome Of Fetus Or Tumor From Plasma."

D. Different Categories of Markers

A "category" for a genomic locus (methylation marker) corresponds to specific variation in methylation levels for a locus across different individuals for a same tissue type. Different categories can have different ranges of variation among a particular tissue type across individuals. A first category of methylation markers might have a difference of 10% in the methylation levels or lower among the individuals tested. A second category of methylation markers might have a difference of more than 10% in the methylation levels among the individuals tested. The use of methylation markers with low inter-individual variations (first category markers) would potentially improve the accuracy of determining the contribution of the particular organ in the DNA mixture.

E. Identification of Potential Methylation Markers

In some embodiments, potential methylation markers were identified in the following manner. Such potential methylation markers can then be subjected to the above criteria to identify type I and type II markers. In other embodiments, an identification of type I or type II is not needed. And, other embodiments may use other techniques to identify potential methylation markers.

In some embodiments, all CpG islands (CGIs) and CpG shores on autosomes were considered for potential methylation markers. CGIs and CpG shores on sex chromosomes were not used so as to minimize variation in methylation levels related to the sex-associated chromosome dosage difference in the source data. CGIs were downloaded from the University of California, Santa Cruz (UCSC) database (genome.ucsc.edu/, 27,048 CpG islands for the human genome) (Kent et al., The human genome browser at UCSC, Genome Res. 2002; 12(6):996-1006) and CpG shores were defined as 2 kb flanking windows of the CpG islands (Irizarry et al. The human colon cancer methylome shows similar hypo- and hypermethylation at conserved tissue-specific CpG island shores. Nat Genet 2009; 41(2):178-186). Then, the CpG islands and shores were subdivided into non-overlapping 500 bp units and each unit was considered as a potential methylation marker.

The methylation densities (i.e., the percentage of CpGs being methylated within a 500 bp unit) of all the potential loci were compared between the 14 tissue types. As previously reported (Lun et al. Clin Chem. 2013; 59: 1583-94), the placenta was found to be globally hypomethylated when compared with the remaining tissues. Thus, the methylation profile of the placenta was not included at the marker identification phase. Using the methylation profiles of the remaining 13 tissue types, the two types of methylation markers were identified. For example, type I markers can refer to any genomic sites with methylation densities that are 3 SD below or above in one tissue when compared with the mean level of the 13 tissue types. Type II markers can considered highly variable when (A) the methylation density of the most hypermethylated tissue is at least 20% higher than that of the most hypomethylated one; and (B) the SD of the methylation densities across the 13 tissue types when divided by the mean methylation density (i.e. the coefficient of variation) of the group is at least 0.25. Lastly, in order to reduce the number of potentially redundant markers, only one marker may be selected in one contiguous block of two CpG shores flanking one CpG island.

F. Selection Based on Application

The set of methylation markers chosen for particular applications can be varied depending on the parameters of the desired applications. For example, for applications focusing on haplotype or allele analysis, useful markers would be those located on the same cell-free DNA molecules as one of the heterozygous alleles. As cell-free DNA molecules (e.g., plasma DNA) are usually less than 200 bp, useful markers can be CpG sites within 200 bp of a heterozygous locus (e.g., a SNP). As another example, for applications in which the release of DNA from a particular tissue into plasma is of special significance, one can select a preferentially larger number of methylation markers that are differentially methylated in this tissue type (e.g. type I marker) when compared with the others in the marker set.

The number and choice of methylation markers in the deconvolution analysis can be varied according to the intended use. If the fractional contribution of the liver is of particular interest, e.g. in a patient who has received a liver transplant, more type I liver specific markers can be used in the deconvolution analysis to increase the precision of the quantification of the contribution of the transplanted liver to the plasma DNA.

III. Composition Accuracy

As described above, embodiments can identify the tissue contributors of plasma DNA. In various examples, genome-wide bisulfite sequencing of plasma DNA was performed and analyzed with reference to methylation profiles of different tissues. Using quadratic programming as an example, the plasma DNA sequencing data were deconvoluted into proportional contributions from different tissues. Embodiments were tested for pregnant women, patients with hepatocellular, lung and colorectal carcinoma, and subjects following bone marrow and liver transplantation.

In most subjects, white blood cells were the predominant contributors to the circulating DNA pool. The placental contributions in pregnant women correlated with the proportional contributions as revealed by fetal-specific genetic markers. The graft-derived contributions to the plasma in the transplant recipients correlated with those determined using donor-specific genetic markers. Patients with hepatocellular, lung or colorectal cancer showed elevated plasma DNA contributions from the organ with the tumor. The liver contributions in hepatocellular carcinoma patients also correlated with measurements made using tumor-associated copy number aberrations.

In cancer patients and in pregnant women exhibiting copy number aberrations in plasma, methylation deconvolution pinpointed the tissue type responsible for the aberrations. In a pregnant woman diagnosed as having follicular lymphoma during pregnancy, methylation deconvolution indicated a grossly elevated contribution from B-cells into the plasma DNA pool and localized B-cells (instead of the placenta) as the origin of the copy number aberrations observed in plasma. Accordingly, embodiments may serve as a powerful tool for assessing a wide range of physiological and pathological conditions based on the identification of perturbed proportional contributions of different tissues into plasma.

A. Contribution of Different Types of Blood Cells

As an example of the methylation deconvolution, we determined the contribution of different tissues and cell types to the circulating DNA. Two blood samples were collected from two patients suffering from systemic lupus erythematosus (SLE). After collection, the venous blood samples were centrifuged at 1,500 g for 10 minutes. After centrifugation, the blood cells and the plasma were separated. DNA was then extracted from the blood cells. The DNA was bisulfite converted and sequenced using one lane of a flow cell in a HiSeq2000 sequencer. Two blood cell samples were analyzed using the cell-type-specific methylation pattern analysis. The methylation patterns of neutrophils, lymphocytes, the esophagus, colon, pancreas, liver, lung, heart, adrenal glands and hippocampus were included as potential candidates of the blood cell DNA. 609 methylation markers were selected for the analysis. The whole blood samples of the two subjects were also sent for cell counting to determine the fractional composition of the neutrophils and lymphocytes of the blood cells.

TABLE 2

Blood tissue contributions by deconvolution pattern analysis and cell counting

| | Blood sample 1 | | Blood sample 2 | |
| --- | --- | --- | --- | --- |
| | Cell type-specific methylation pattern analysis | Blood cell counting | Cell type-specific methylation pattern analysis | Blood cell counting |
| Neutrophils | 90.5% | 93.6% | 89.4% | 89.9% |
| Lymphocytes | 9.5% | 6.4% | 10.6% | 10.1% |
| Esophagus | 0% | — | 0% | — |
| Colon | 0% | — | 2% | — |
| Pancreas | 0% | — | 0% | — |
| Liver | 0% | — | 1% | — |
| Lung | 1% | — | 1% | — |
| Heart | 0% | — | 3% | — |
| Adrenal gland | 0% | — | 0% | — |
| Hippocampus | 0% | — | 0% | — |

For methylation pattern analysis, neutrophils and lymphocytes were determined as the major components constituting the blood cell DNA. The relative proportion of the contribution of neutrophils and lymphocytes resemble their relative abundance in the blood samples according to the cell counting analysis.

B. Pregnant Women

The contributions of different tissues, including the liver, lung, pancreas, colon, hippocampus, small intestines, blood cells, heart, adrenal gland, esophagus and placenta, were analyzed using methylation analysis of the plasma DNA of pregnant women. As the placental genotype is in general identical to the fetus's genotype but different from the pregnant woman's genotype, the precise contribution of the placenta to the maternal plasma can be accurately determined by counting the number of fetal specific-alleles in the sample.

1. Composition and Correlation to Fetal DNA Percentage

Genome-wide bisulfite sequencing of plasma DNA was performed for 15 pregnant women, five from each of first, second and third trimesters. Methylation deconvolution was performed and the percentage contributions from different tissues were deduced. The contributions of different organs were determined based on the methylation levels (such as methylation densities) of all the type I and type II markers in table S1 using quadratic programming analysis.

Figure 3A:
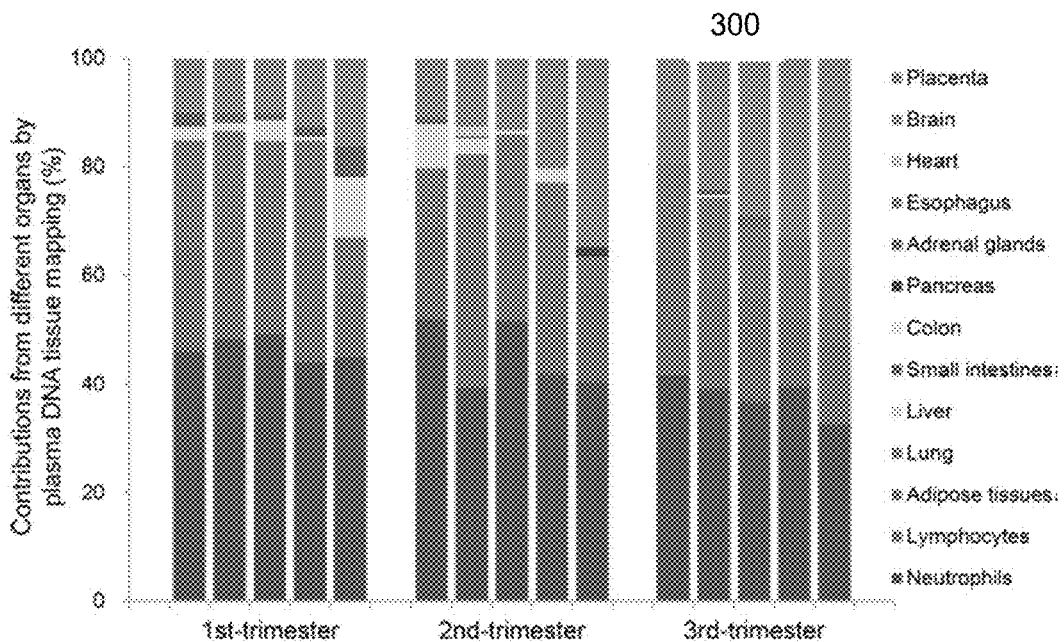
FIG. 3A shows a graph of percentage contributions of different organs to plasma DNA for 15 pregnant women according to embodiments of the present invention.

FIG. 3A shows a graph 300 of percentage contributions of different organs to plasma DNA for 15 pregnant women according to embodiments of the present invention. Each bar corresponds to the results of one sample. The different colors represent the contributions of different organs into plasma. These results show that the white blood cells (i.e. neutrophils and lymphocytes) are the most important contributors to the plasma DNA pool. This observation is consistent with those previously obtained following bone marrow transplantation (Lui Y Y et al. Clin Chem 2002; 48: 421-7).

FIG. 4 shows a table 400 of percentage contributions determined from a plasma DNA tissue mapping analysis among pregnant women according to embodiments of the present invention. These results also show that the placenta is another key contributor of the plasma DNA in pregnant women, with fractional concentrations from 9.9% to 38.4%.

We also measured the placental contributions using paternally-inherited fetal single nucleotide polymorphism (SNP) alleles that were not possessed by the pregnant women as previously described (31). To analyze the fetal-specific SNP alleles, the genotypes of the fetuses were determined by analyzing the chorionic villus samples or the placenta. The genotypes of the pregnant women were determined by analyzing the blood cells. The SNP-based results show the independent validation of the methylation deconvolution results.

Figure 3B:
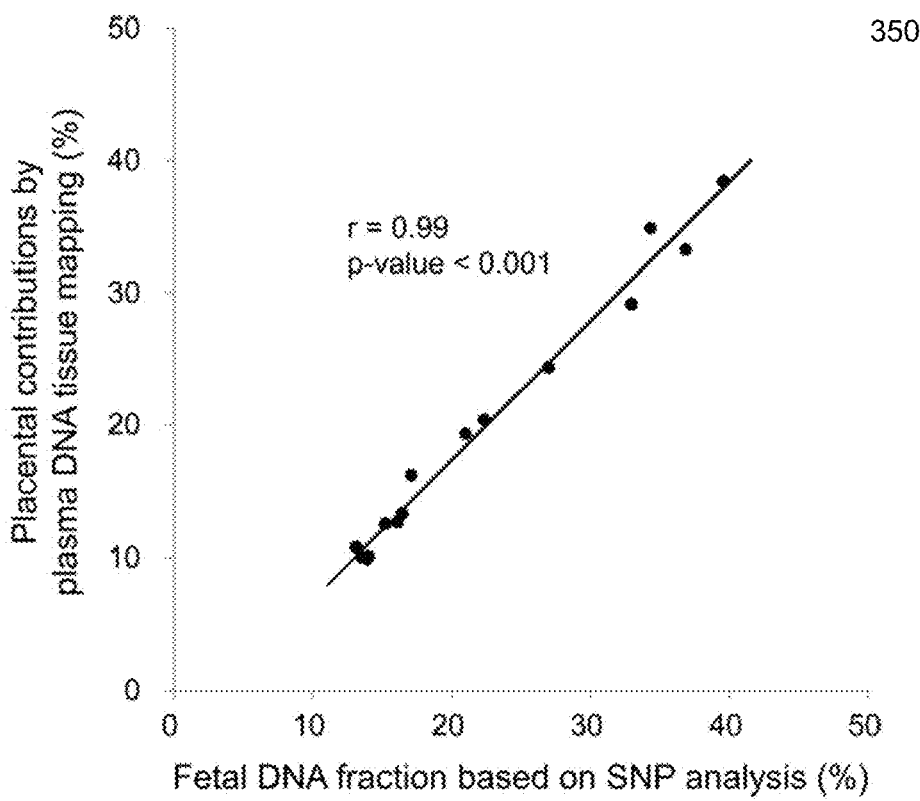
FIG. 3B shows a plot 350 of a correlation between the plasma DNA fractions contributed by the placenta deduced from plasma DNA methylation deconvolution and the fetal DNA fractions deduced using fetal-specific SNP alleles according to embodiments of the present invention.

FIG. 3B shows a plot 350 of a correlation between the plasma DNA fractions contributed by the placenta deduced from plasma DNA methylation deconvolution and the fetal DNA fractions deduced using fetal-specific SNP alleles according to embodiments of the present invention. Plot 350 shows that the placental contributions determined by methylation deconvolution have a strong correlation with the fetal DNA fractions measured using SNPs ($r=0.99$, $p<0.001$, Pearson correlation). Accordingly, a good positive correlation is observed between the values of the two parameters, suggesting that the plasma DNA methylation deconvolution accurately determines the contribution of the placenta to the maternal plasma samples.

Figure 5:
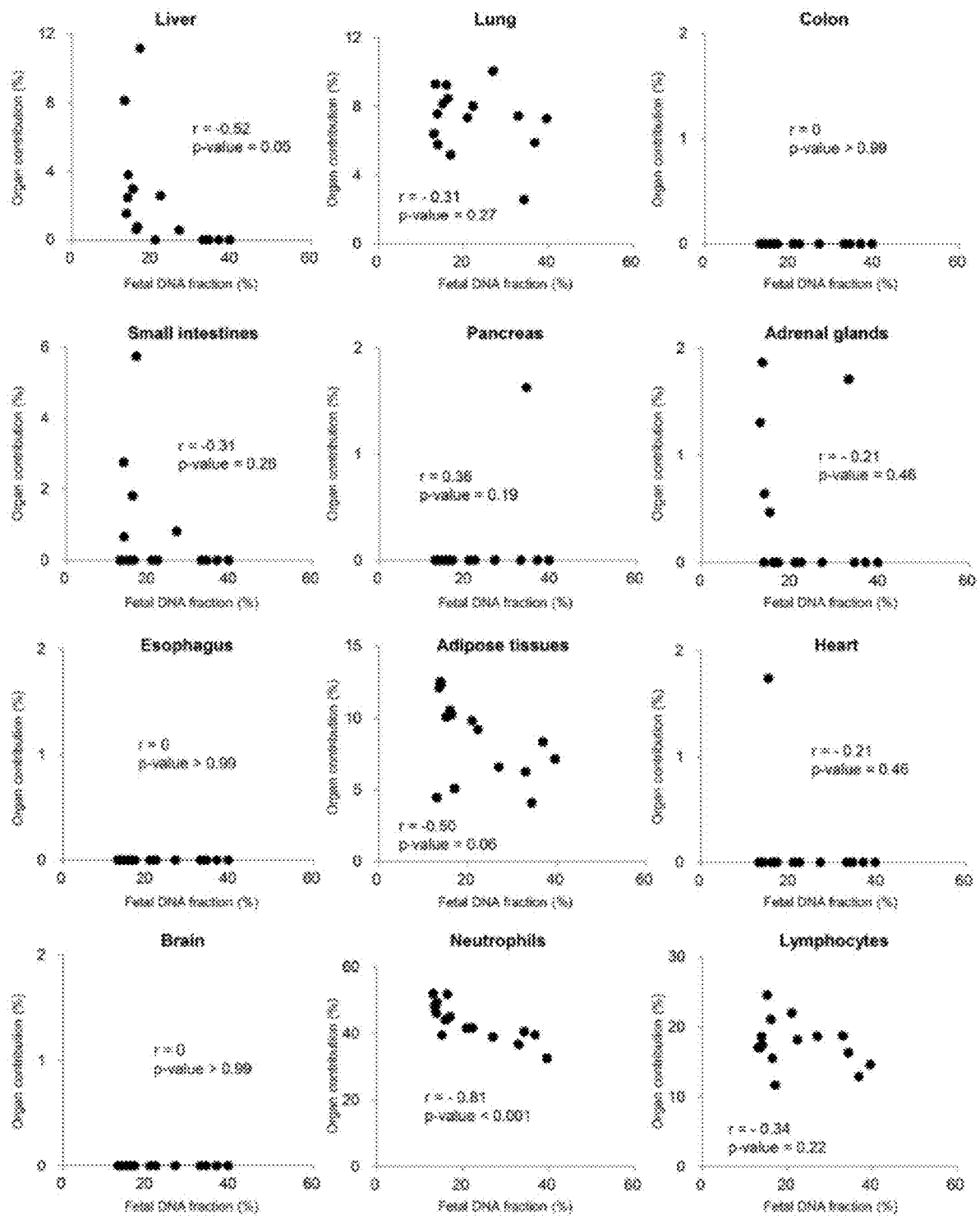
FIG. 5 shows plots of percentage contributions of organs other than the placenta by plasma DNA tissue mapping and fetal DNA fractions based on fetal-specific SNP alleles according to embodiments of the present invention.

FIG. 5 shows plots of percentage contributions of organs other than the placenta by plasma DNA tissue mapping and fetal DNA fractions based on fetal-specific SNP alleles according to embodiments of the present invention. The X-axis represents the fetal DNA fractions estimated by SNP-based analysis and the Y-axis represents the percentage contribution deduced by plasma tissue DNA mapping analysis. Plasma DNA contributions of the neutrophils show a reverse correlation. This is likely due to the fact that neutrophils are a major contributor to the plasma DNA pool and hence, as the placental contribution increases, the relative contribution from the neutrophils would by necessity decrease. The methylation deconvolution results of the remaining tissues show no correlation with the fetal DNA fraction.

FIG. 6 shows a table 600 of percentage contributions from plasma DNA tissue mapping analysis among the non-pregnant healthy control subjects according to embodiments of the present invention. When the process was applied to plasma of non-pregnant healthy controls, placental contribution was absent in most samples (median: 0%; interquartile range: 0% to 0.3%).

2. Comparison of Selected Markers Vs. Random Markers

The accuracy of the percentage contributions was tested with select markers relative to random markers. Different composition calculations were done for different sets of markers. One set was chosen based on criteria mention above, and the other was a random set. The results show that it is important to judicially choose the methylation markers (genomic loci) use, in order to obtain accurate results.

Eleven pregnant women and four healthy non-pregnant subjects were recruited for this analysis. Their plasma DNA was bisulfite converted and sequenced using the Illumina HiSeq2000 sequencer. Each plasma sample was sequenced with one lane of a sequencing flow cell. The sequence reads were then analyzed using a bioinformatic program, Methy-Pipe (Jiang P. PLoS One 2014; 9: e100360). This program can align the bisulfite-converted sequence reads to the reference genome and determine the methylation status of each CpG site on each sequenced fragment.

The first set of markers have high specificity for identifying the different tissues in the plasma DNA. For each tissue type, markers that have the biggest difference in methylation density compared with the other tissues were selected. The markers were determined from genomic regions containing at least one CpG dinucleotide. In this example, CpG islands (CGIs) were used as potential markers, having a high frequency of CpG sites in a particular stretch of DNA. CGIs in this particular example are downloaded from the University of California, Santa Cruz (UCSC) database: (genome.ucsc.edu). In total, we obtained 27,048 CpG islands from the human genome. The median size of a CpG island is 565 bp (range: 200 bp to 45 kb). 90% of the islands are less than 1.5 kb.

For each methylation marker, the difference in methylation density between the tissue-of-interest and the other tissues was determined. The difference is then expressed as the number of standard deviations (SDs) across the other tissues. For the tissue-of-interest, all the markers were ranked according to this difference in methylation density. The 20 markers with the biggest difference above (10 markers) and below (10 markers) the mean methylation densities of the other tissues were selected. The number of markers can vary, for example, but not limited to 5, 15, 20, 30, 40, 50, 100 and 200.

In addition, markers with a high variability across all the different tissues were also selected. In this example, markers with >50% difference between the tissues with the highest and lowest methylation densities were selected. In other applications, other values, for example, but not limited to 20%, 30%, 40%, 60%, 70% and 80%, can be used. Furthermore, the variability of methylation densities across different tissues was also calculated based on the mean and SD. In this example, a marker was also selected if the value of SD is more than two times the mean. In other applications, other cutoff values, for example, but not limited to 1, 1.5, 2.5 and 3, can also be used. Based on these selection criteria, 344 methylation markers were selected for the first set.

For the second set, 341 markers were randomly selected from the 27,048 CGIs discussed above. All the CGIs were first numbered from 1 to 27,048. Then a random number (between 1 and 27,048) was generated by a computer for marker selection. This process was then repeated until a total of 341 markers were selected. If a random number generated had been used, another one would be generated. This set of markers is expected to have a much lower specificity in identifying the tissue-specific methylation patterns. Thus, the accuracy of determining the composition of the plasma DNA is expected to be reduced.

FIG. 7 shows a table 700 of the estimated contributions of different organs to the plasma DNA for 11 pregnant women and 4 non-pregnant healthy subjects using the first set of markers (with high organ specificity) according to embodiments of the present invention. The fetal DNA fractions were determined by counting fetal-specific alleles and are shown in the bottom row. In each of the four non-pregnant control subjects, the contribution of the placenta to the plasma was determined to be close to 0%. This indicates the specificity of this approach.

FIG. 8 shows a table 800 of the estimated contributions of different organs to the plasma DNA for 11 pregnant women and 4 non-pregnant healthy subjects using the second set of markers (with low organ specificity) according to embodiments of the present invention. The fetal DNA fractions determined by counting fetal-specific alleles are shown in the bottom row. Using these less specific markers, a relatively non-concordant percentage of contribution from the placenta was observed, and considerable contributions from the placenta were observed in the four non-pregnant control subjects. This indicates that the tissue specificity of the markers is important in this approach.

Figure 9A:
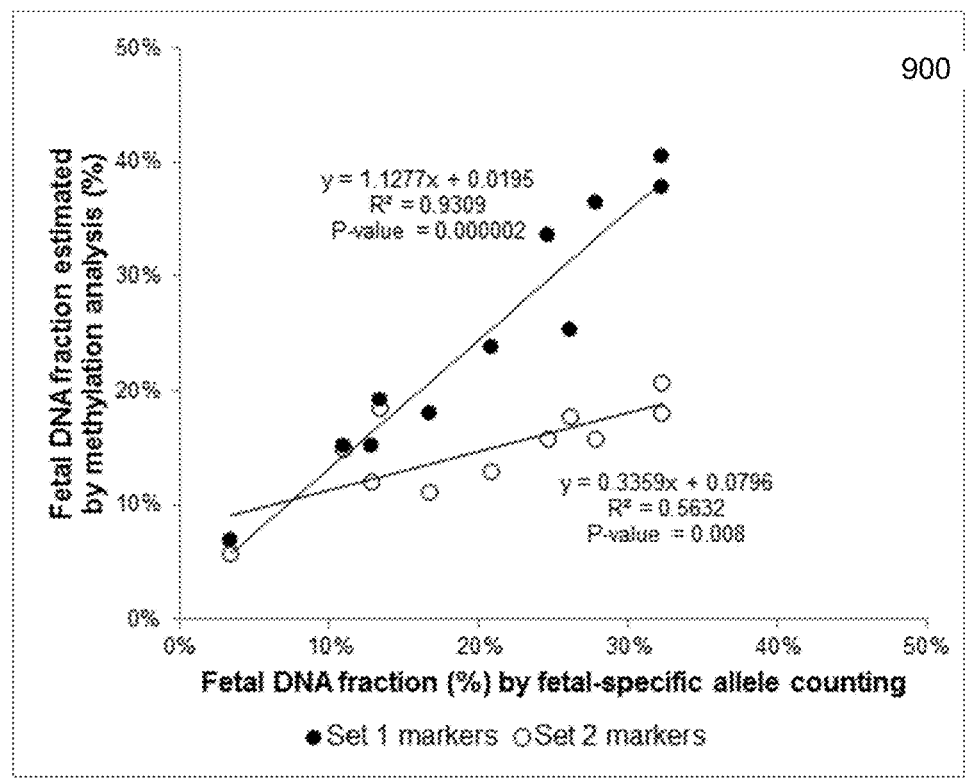
FIG. 9A is a plot showing the correlation between the estimated fetal DNA fraction (contribution from the placenta) and the fetal DNA fraction determined by counting the fetal-specific alleles in the maternal plasma samples.

FIG. 9A is a plot 900 showing the correlation between the estimated fetal DNA fraction (contribution from the placenta) and the fetal DNA fraction determined by counting the fetal-specific alleles in the maternal plasma samples. The results from the two techniques have good correlation using the first set of methylation markers. However, using the second set of methylation markers, the estimation by using the methylation analysis showed significant deviation from the true values determined using fetal-specific alleles counting.

Figure 9B:
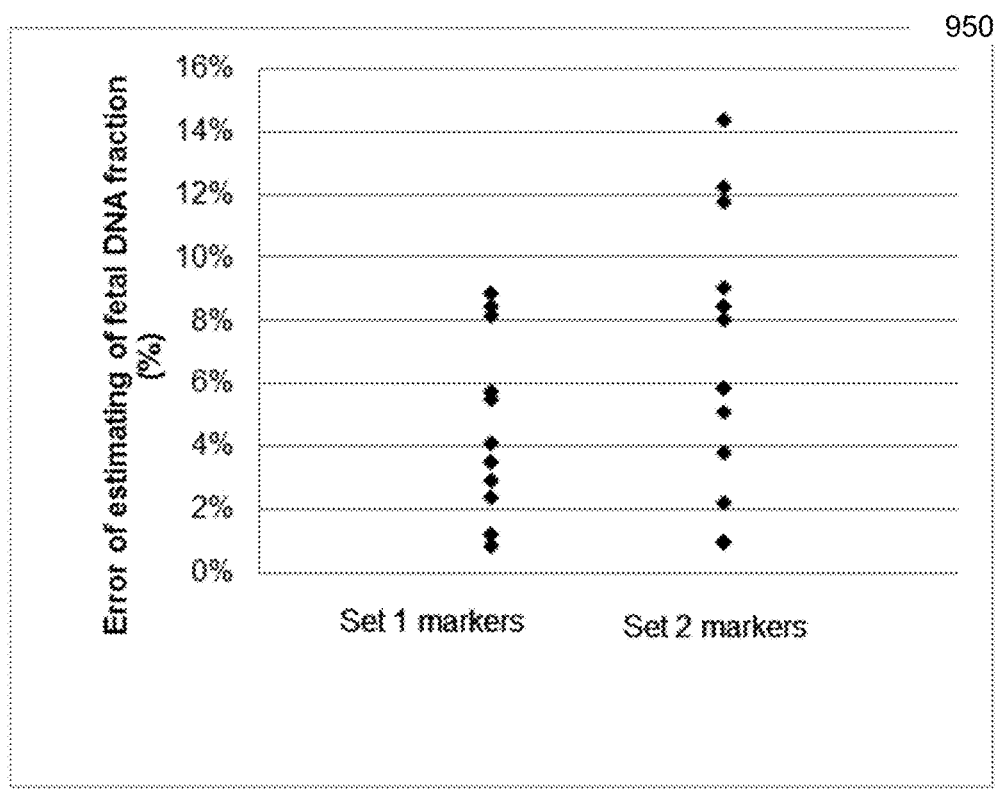
FIG. 9B is a plot showing absolute difference between the estimation from methylation markers and fetal DNA fraction determined by fetal-specific alleles counting.

FIG. 9B is a plot 950 showing absolute difference between the estimation from methylation markers and fetal DNA fraction determined by fetal-specific alleles counting. The median error of the estimation using methylation analysis were 4% and 8% using the first set of markers and the second set of markers, respectively.

C. Effect of Different Criteria

As described above, various criteria can be used to identify markers of different types. For example, a type I marker can be identified by a methylation level in a particular tissue that is different from the mean methylation level for all tissues, e.g., at least by a specific threshold, such as 3 SD. And, for type II markers, criteria of a certain variation and maximum difference are used. Sections below show accuracy of different criteria for identifying markers.

1. Performance of Markers with Less Stringent Criteria

We compared the performance of methylation deconvolution analysis using markers with different variability across different tissues. The placental contributions to plasma DNA were determined for 15 pregnant women based on two sets of markers with different selection criteria. Both sets of markers include all the type I markers as described in previous sections. However, the selection criteria of type II markers are different for the two sets of markers.

Set I markers include all the 5,820 type II markers fulfilling the criteria of having methylation density CV>0.25 and the difference between the maximum and minimum methylation densities for the groups of tissues exceeding 0.2. For Set II markers, the CV requirement was >0.15 and the difference between the maximum and minimum methylation densities for the groups of tissues exceeded 0.1. There were 8,511 type II markers in this set of markers.

Figure 10A:
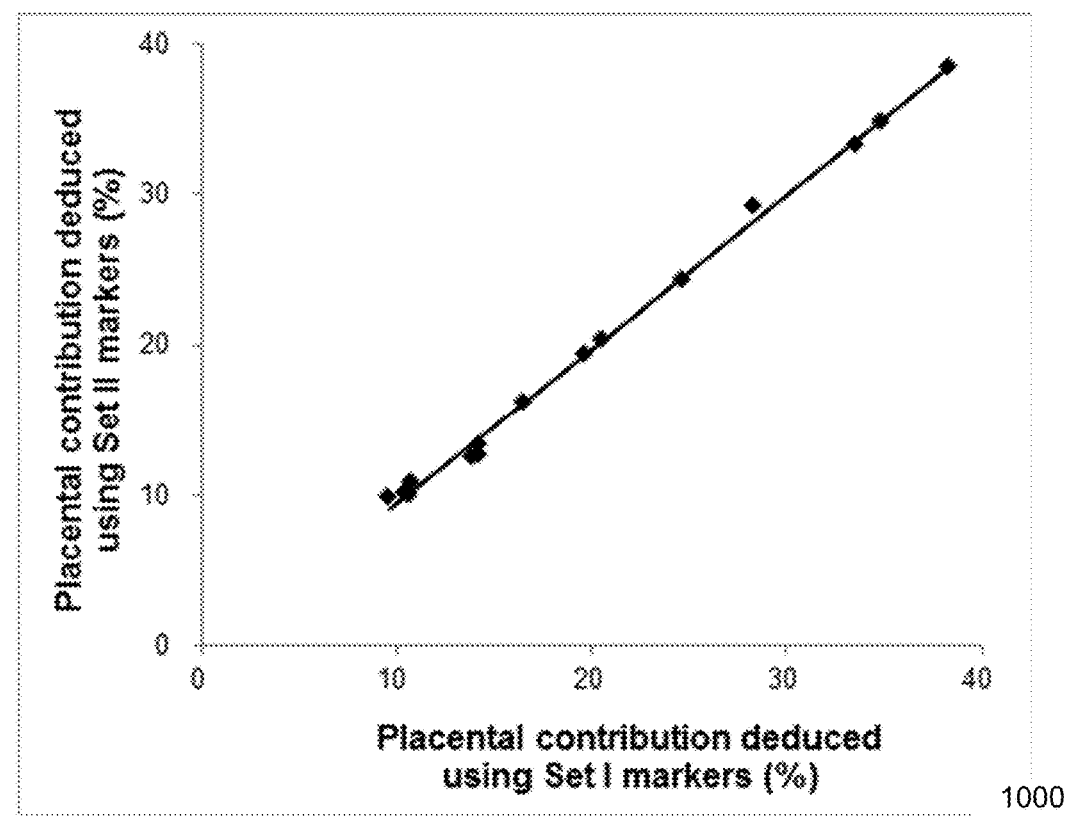
FIG. 10A is a graph showing placental contribution to plasma DNA deduced using markers with different selection criteria according to embodiments of the present invention.

FIG. 10A is a graph 1000 showing placental contribution to plasma DNA deduced using markers with different selection criteria according to embodiments of the present invention. The vertical axis corresponds to placental contribution deduced using the set II markers. The horizontal axis corresponds to placental contribution deduced using the set I markers. There was a good correlation between the placental contribution results based on the two sets of markers with different selection criteria (r=0.99, Pearson correlation). Accordingly, good accuracy can be obtained using the requirements of CV>0.15 and of the difference between the maximum and minimum methylation densities for the groups of tissues exceeding 0.1.

2. Effect of Methylation Level Variation within Same Type of Tissue

To investigate if the variation in methylation level of markers between the same type of tissues (e.g. from different individuals) would affect the performance of deconvolution analysis, we analyzed placental tissues from two pregnant cases. Two categories of methylation markers were identified. Specifically, the two categories were identified based on their similarity in methylation levels in two placental tissues. Markers of category i have a methylation density of 10% or lower. Markers of category ii have high variability between the two placental tissues (difference in methylation density of more than 10%).

Figure 10B:
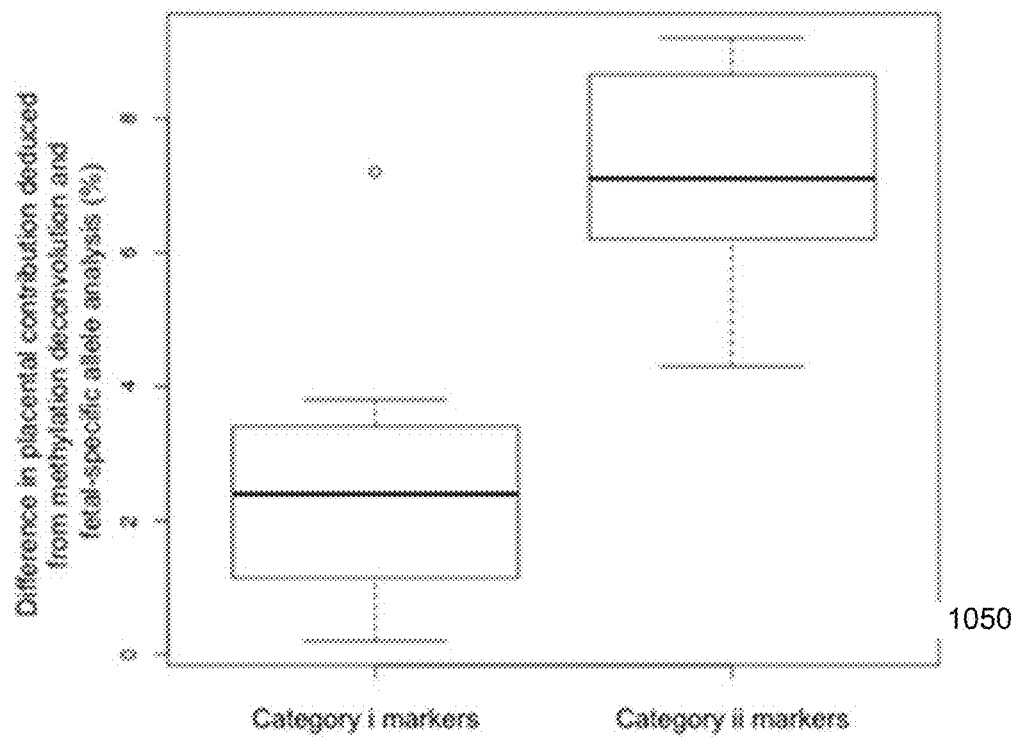
FIG. 10B is a graph showing the accuracy of plasma DNA deconvolution using markers with low variability (category i) and high variability (category ii) in the same type of tissue.

FIG. 10B is a graph 1050 showing the accuracy of plasma DNA deconvolution using markers with low variability (category i) and high variability (category ii) in the same type of tissue. Plasma DNA deconvolution was performed to determine the placental contribution to the plasma DNA for 15 pregnant women. For each marker, the mean of the methylation densities of the two placental tissues were used to represent the methylation level of the placenta in the analysis. For each of the deconvolution analysis using the category i and category ii markers, a total of 1,024 markers were used.

The amount of placentally-derived DNA in plasma was further determined based on the proportion of the fetal-specific SNP alleles. The percentage contribution deduced by the methylation deconvolution analysis based on category i and category ii markers were then compared with the results based on fetal-specific SNP alleles. The median deviation of the derived placental contribution from the value estimated based on fetal-specific alleles was 2.7% and 7.1% using category i and category ii markers, respectively. Thus, the use of category i markers which had lower inter-individual variation in the tissue methylation level gave better accuracy in the methylation deconvolution analysis.

Significantly higher difference between the results from methylation deconvolution and fetal-specific allele analysis was observed when markers with high variability within the same type of tissue (category ii) were used (P<0.0001, Wilcoxon sign-rank test). In other words, the use of markers with low variability within the same type of tissue would increase the accuracy of methylation deconvolution analysis. Accordingly, markers can be selected based on the variability within the same type of tissues, for example, but not limited to the value of CV and the difference between the maximum and minimum methylation density for the same type of tissues.

IV. Deconvolution of Fetal Signatures

If a genomic signature (e.g., a particular SNP allele) is known, embodiments can determine which tissue is the origin of such signatures. Thus, if a particular signature is representative of a fetus (e.g., a paternal allele at a particular locus), then the fractional contribution for the signature would be substantial for the placental tissue.

To illustrate that single nucleotide alteration can also be used to determine the tissue of origin that the alteration is derived from, we analyzed the plasma DNA of a pregnant woman. The placenta and the maternal buffy coat were genotyped to identify the SNPs that the mother was homozygous and the fetus was heterozygous. We denote the allele shared by the fetus and the mother as A and the fetal-specific allele as B. Therefore, the mother had a genotype of AA and the fetus had a genotype of AB at each of these SNPs.

After bisulfite sequencing of the maternal plasma DNA, all DNA fragments carrying the fetal-specific allele (B allele) and at least one CpG site were selected and used for downstream analysis. A total of 1.31 billion fragments were sequenced and 677,140 fragments carrying the fetal-specific allele (B allele) were used for the deconvolution analysis. All CpG sites that were covered by at least 10 DNA fragments were used for deconvolution analysis. Other numbers of DNA fragments covering a site can be used, such as 5, 15, 20, 25, or 30. As the B allele was fetal specific, these DNA fragments were expected to be derived from the placenta.

TABLE 3

Methylation deconvolution analysis using fetal-specific allele.

| Tissue | Contribution (%) |
| --- | --- |
| Liver | 0.9 |
| Lung | 0.0 |
| Colon | 0.0 |
| Small intestines | 0.0 |
| Pancreas | 0.5 |
| Adrenal glands | 0.0 |
| Esophagus | 3.1 |
| Adipose tissues | 0.0 |
| Heart | 0.0 |
| Brain | 0.3 |
| T cells | 0.0 |
| B cells | 0.0 |
| Neutrophil | 0.0 |
| Placenta | 95.2 |

In Table 3, from the methylation deconvolution analysis, it was shown that the placenta was deduced to be the major contributor for these DNA fragments carrying fetal-specific SNP alleles. These results suggest that the methylation deconvolution analysis accurately identified the tissue origin of these DNA fragments carrying fetal-specific alleles.

This shows that a particular allele can be attributed to a fetus. Such a technique is described in more detail below for determining genotypes and haplotypes of a fetus using methylation deconvolution analysis.

V. Determination of Fetal Genome (Mutational Analysis)

For noninvasive prenatal testing, the analysis of the inheritance of a maternal mutation using maternal plasma DNA is a challenging task. For example, if a pregnant woman is heterozygous for a mutation, the analysis on the mutational status of the fetus using maternal plasma DNA analysis would be technically difficult because both the mutant and the normal alleles would be present in her plasma, regardless of the mutational status of her fetus. Previously, a number of different approaches have been developed to address this problem (Lun et al. Proc Natl Acad Sci USA. 2008; 105:19920-5; Lo et al. Sci Transl Med. 2010; 2:61ra91; Lam et al. Clin Chem. 2012; 58:1467-75). The principle of these previous approaches involves the comparison between the relative amounts of the mutation and the normal allele in maternal plasma. To enhance the statistical power of the comparisons, some of these approaches further involve the comparisons of the relative amounts of SNP alleles linked to the mutation and those linked to the normal allele. As an alternative or in addition, some embodiments of the present invention can deduce the mutational status of the fetus by methylation deconvolution analysis.

A. Contribution for Alleles Using Methylation Deconvolution

In this example, a genotype of the fetus is determined. Assume the genotypes of the father and mother are NN and MN at a particular locus, respectively. M and N denote the mutant and normal alleles, respectively. In this scenario, the fetus can inherit either the M allele or the N allele from the mother. Therefore, there are two possible genotypes for the fetus, namely MN and NN. In maternal plasma, DNA carrying the fetal genotype is actually derived from the placenta. Thus, these DNA fragments would exhibit the placental methylation profile.

Figure 11A:
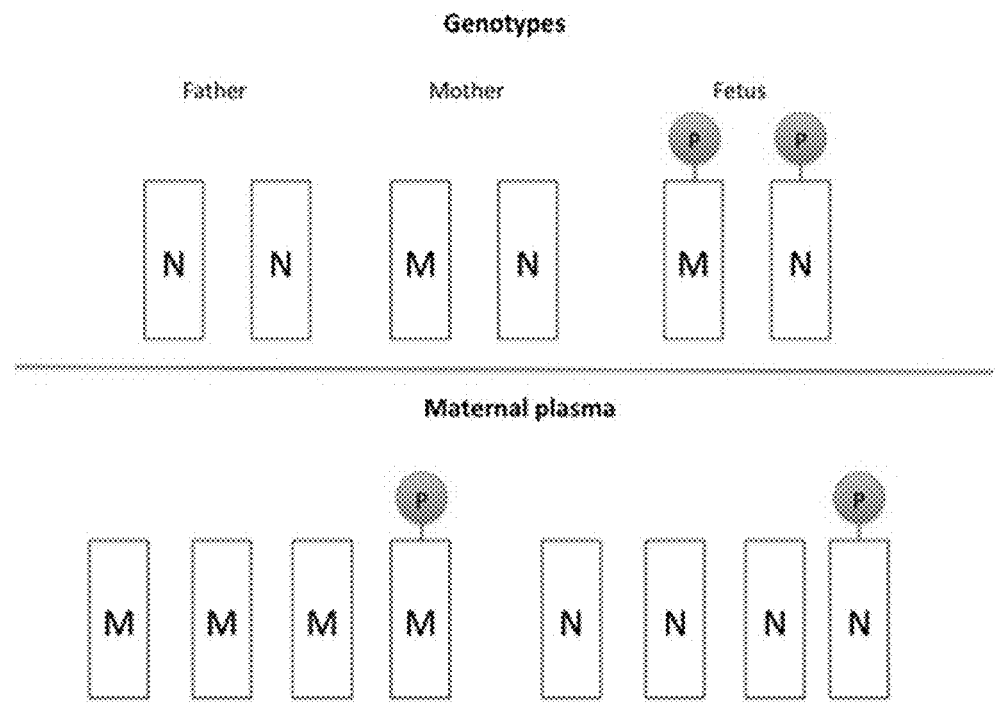
FIG. 11A shows a first scenario where the fetus has inherited the M allele from the mother and has a genotype of MN at a particular locus according to embodiments of the present invention.

FIG. 11A shows a first scenario where the fetus has inherited the M allele from the mother and has a genotype of MN at a particular locus according to embodiments of the present invention. In the top part of FIG. 11A (labeled Genotypes), the father is shown as having genotype NN, the mother is shown as having genotype MN, and the fetus is shown as having genotype MN. The DNA fragments that exhibit the placental methylation profile are marked with a P, where are shown on the fetal genotype. For example, the placental methylation profile can correspond to certain methylation levels at genomic sites near the particular locus. DNA fragments that align to the particular locus can also include genomic sites near the locus (e.g., within 200 bp of the locus), and thus can be used to measure methylation levels for the methylation deconvolution analysis. Considering the genotypes of the parents, the M allele is specific for the mother and the N allele is shared between the father and the mother.

In the bottom part of FIG. 11A (labeled Maternal plasma), instances of the two alleles M and N are shown, with each instance representing a different DNA molecule in the plasma at the locus of interest. Only a small number of DNA molecules are shown for illustration purposes. In this example, the fetal DNA percentage is assumed to be 25%, as shown by 25% of the DNA molecules being marked with a P.

In the maternal plasma sample, we selectively analyzed the DNA fragments carrying the M allele and performed the methylation deconvolution analysis. Because the fetus has a genotype of MN, the placenta would contribute both M and N alleles to the maternal plasma DNA. Therefore, some of the DNA fragments carrying the M allele would also carry the placenta-specific methylation profile at genomic sites near the locus. The methylation deconvolution analysis would indicate that some of the DNA fragments carrying the M allele would be derived from the placenta, and thus the fetal genotype does include the M allele.

Figure 11B:
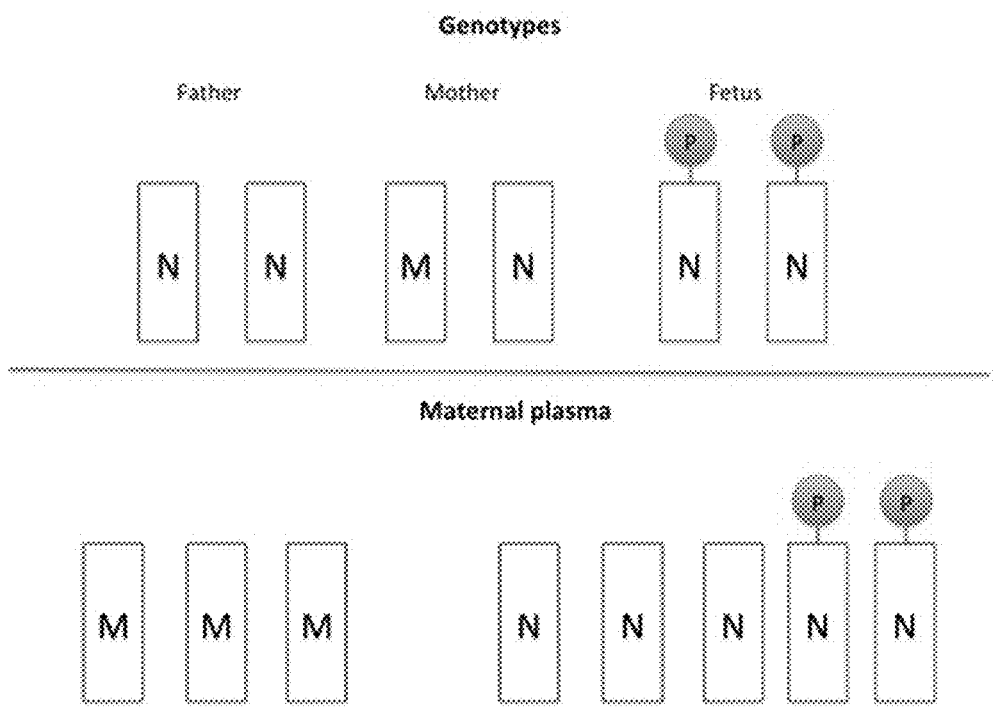
FIG. 11B shows a second scenario where the fetus has inherited the N allele from the mother and has the genotype of NN at a particular locus according to embodiments of the present invention.

FIG. 11B shows a second scenario where the fetus has inherited the N allele from the mother and has the genotype of NN at a particular locus according to embodiments of the present invention. In this situation, only the DNA fragments carrying the N allele would exhibit the placental methylation profile in maternal plasma. Thus, the selective analysis of the DNA fragments carrying the M allele with methylation deconvolution would indicate that these DNA fragments do not have significant contribution from the placenta. Accordingly, it can be determined that the fetus does not have M, and thus has a genotype of NN.

In some embodiments, the placental contribution for the M and N alleles can be compared. Here, we assume that the fetal DNA accounts for approximately 10% of the total maternal plasma DNA. The selective deconvolution of the M and N alleles would be useful to indicate which allele the fetus has inherited from the mother. The expected results are shown in Table 4 below:

TABLE 4

Placental contributions for M and
N alleles for NN paternal genotype.

|  | Fetal genotype | |
| --- | --- | --- |
|  | MN | NN |
| Placental contribution for plasma DNA carrying the M allele | Approximately 10% | Insignificant (close to zero) |
| Placental contribution for plasma DNA carrying the N allele | Approximately 10% | Approximately 20% |
| Ratio of placental contribution for M and N alleles (M:N) | 1:1 | 0:2 |

In Table 4, the percentage placental contribution of the M and N alleles can be compared. An approximately equal placental contribution for the two alleles (e.g., within a threshold of each other) suggests that the fetal genotype is MN. On the other hand, a significantly higher placental contributions for the N allele compared with the M allele would indicate a fetal genotype of NN.

In another embodiment, the paternal genotype does not need to be taken into account. In this situation, the possible genotypes of the fetus include MM, MN, and NN.

TABLE 5

Placental contributions for M and N alleles
for unknown paternal genotype.

|  | Fetal genotype | | |
| --- | --- | --- | --- |
|  | MN | NN | MM |
| Placental contribution for plasma DNA carrying the M allele | Approximately 10% | Insignificant (close to zero) | Approximately 20% |
| Placental contribution for plasma DNA carrying the N allele | Approximately 10% | Approximately 20% | Insignificant (close to zero) |
| Ratio of placental contribution for M and N alleles (M:N) | 1:1 | 0:2 | 2:0 |

In table 5, the placental contribution for the DNA fragments carrying the M and N alleles for different fetal genotypes are shown. When the fetus has a genotype of MM, the placental contribution for the M allele would be significantly higher than that for the N allele. When the fetus has a genotype of NN, the placental contribution for the N allele would be significantly higher than that for the N allele. When the fetus has a genotype of NM, the placental contribution for the M allele would be approximately equal to the placental contribution for the N allele.

Accordingly, where the paternal genotype is not known, fractional contributions can be determined for both alleles. That is, a first fractional contribution can be determined using a first set of cell-free DNA molecules that align to the locus and include N. Methylation levels of the first set of cell-free DNA molecules can be measured at K genomic sites near the locus. And, a second fractional contribution can be determined using a second set of cell-free DNA molecules that align to the locus and include M. Methylation levels of the second set of cell-free DNA molecules can be measured at the K genomic sites near the locus. For the first scenario of the fetal genotype being MN, the fractional contributions determined for either allele would be about the same, as can be tested to by determining whether the fractional contributions are within a threshold value of each other.

To illustrate the feasibility of this approach, we analyzed the plasma DNA of a pregnant woman. The plasma DNA was bisulfite converted and analyzed using massively parallel sequencing. In addition, the placenta and blood cells were analyzed to determine the genotype of the fetus and the mother. For illustration purposes, a SNP located within the KLF2 gene was analyzed. For this SNP, the genotypes of the mother and the fetus were CG and CC, respectively. With this genotype combination, the placenta would contribute the C allele to the maternal plasma, but all the G alleles in the maternal plasma would be derived from the maternal tissues.

In the sequencing data, there were 24 fragments carrying the G allele and 55 fragments carrying the C allele. The CpG sites within these DNA fragments were used for methylation deconvolution. In this analysis, an objective is to determine the placental contribution of the two alleles. To illustrate the principle, only the placenta and the blood cells were considered as candidate tissues for the methylation deconvolution analysis. In another embodiment, three or more types of tissues can be used as candidates. In yet another embodiment, tissues expected to have significant contribution, for example blood cells, liver, lung, intestines and placenta, can be used as candidates.

TABLE 6

Placental contributions for C and G alleles
for unknown paternal genotype.

|  | C allele | G allele | C/G ratio |
| --- | --- | --- | --- |
| Placenta | 62.6% | 1.8% | 34 |
| Blood cells | 37.4% | 98.2% |  |

In Table 6, the contribution from the placenta was deduced to be 62.6% and 1.8% for the C allele and the G allele, respectively. The ratio of placental contribution for C/G is 34. These results suggest that the genotype of the fetus would be CC. This is consistent with the genotyping result of the placental tissue.

This embodiment is different from and potentially has more utility than a previous method for noninvasive prenatal testing based on the analysis of allelic ratio for DNA with a specific methylation pattern (Tong et al. Clin Chem 2006; 52: 2194-202). In this previous method, tissue-specific DNA is first identified from a DNA mixture (e.g. plasma DNA) based on methylation pattern. For example, a particular gene is completely unmethylated in the blood cells and methylated in the placenta. The identification is performed using an enzyme that leaves the methylated placental DNA intact. Thus, all the methylated DNA molecules remaining in the plasma would be derived from the placenta rather than from the blood cells. Then, the allelic ratio for a SNP located on the placenta-derived DNA molecules can be determined by measuring amounts of the different alleles at the locus using the intact placental DNA. When the fetus is heterozygous for the SNP, the ratio of the two alleles in the placenta-specific DNA would be approximately 1. However, if the fetus is affected by an aneuploid chromosome and has three copies of the chromosome carrying this particular SNP, the ratio of the two alleles would be either 1:2 or 2:1.

In this previous method, the tissue-specific DNA molecules need to be first identified based on a methylation status that is unique to the tissue of interest. The methylated DNA molecules are unique for the placenta because the blood cells are completely unmethylated for the targeted region. However, in this present embodiment, the uniqueness of a certain methylation state is not required. The candidate tissues only need to be different in their methylation profiles, accordingly more loci can be used, thereby enabling haplotype deconvolution. Thus, the tissue contributions can be determined for the different alleles based on their methylation profiles. Further, the previous method may be more susceptible to statistical variations as the numbers of fetal reads with each allele are compared directly to each other. Whereas, when the placental contributions are compared to each other, the numbers of fetal reads are not compared directly to each other. Instead, the placental contribution is determined from all of the reads (methylated or not), and thus the placental contributions can be the same, even when the number of fetal reads differs. Thus, a coverage bias to one haplotype can be accounted for.

B. Determination of Inherited Haplotype Using Deconvolution

It has previously been demonstrated that through the analysis of plasma DNA (or other cell-free DNA) of a pregnant woman carrying a fetus, the maternal haplotypes inherited by the fetus can be deduced using the process of relative haplotype dosage analysis (RHDO) (Lo et al. Sci Transl Med 2010; 2: 61ra91 and U.S. Pat. No. 8,467,976). In this method, one uses the haplotype information for the pregnant woman. This latter information can be obtained using family analysis or a method for the direct analysis of the haplotype (e.g. Fan et al. Nat Biotechnol 2011; 29: 51-57; Snyder et al. Nat Rev Genet 2015; 16: 344-358). SNPs that are heterozygous in the mother but homozygous in the father can be used for the RHDO analysis. Such a use of specific SNPs can limit the loci that can be used, and therefore limit the amount of data and accuracy. Embodiments may not be so restricted to such specific SNPs. Further, embodiments can be used in combination with the above references to provide increased accuracy.

Embodiments can use methylation deconvolution to determine placental contributions using the cell-free DNA molecules for two haplotypes. The placental contributions can be compared to determine which haplotype is inherited by the fetus. Embodiments can start with deduced maternal or paternal haplotypes, and then measure the methylation levels of plasma DNA molecules containing SNP alleles in each of those deduced haplotypes. One can then perform methylation deconvolution. The fetal haplotype can be identified as the one with the highest placental contribution from the methylation deconvolution analysis. In all of the above embodiments, the paternal or maternal haplotypes can, instead of being a deduced one, also be determined by family analysis (i.e. by analyzing the DNA of other family members) or by a direct method (e.g. the method described by Fan et al Nat Biotechnol 2012).

1. Maternal Haplotypes

In this example, we demonstrate plasma DNA methylation deconvolution analysis can be used for deducing the maternal haplotypes inherited by an unborn fetus. A source of genomic DNA from the pregnant woman, e.g. the buffy coat DNA, can be subjected to genotyping, e.g. using a microarray. Then, the maternal genotyping results are entered into a haplotype deduction program (e.g., IMPUTE2, Howie et al. PLoS Genet. 2009; 7:e1000529) to deduce the likely first maternal haplotype and the second maternal haplotype. Population-specific genotype and haplotype information can be taken into consideration for improving the accuracy of deduction. In other embodiments, the parental haplotypes can be worked out by single molecule analysis, for example but not limited to the methods described by Fan et al (Nat Biotechnol. 2011; 29:51-7), Kaper et al (Proc Natl Acad Sci USA. 2013; 110:5552-7), Lan et al. (Nat Commun. 2016; 7:11784) and Selvaraj et al (Nat Biotech 2013; 31:1111-1118). Then, maternal plasma DNA can be subjected to genome-wide bisulfite sequencing and alignment to reference genomic sequences. Methylation deconvolution can then be performed for each of the predicted haplotypes. As fetal DNA in maternal plasma is predominantly of placental origin, the maternal haplotype inherited by the fetus is the one that shows the highest placental contribution.

The maternal haplotype information can be used to link the SNP alleles and the CpG sites on the same homologous chromosome together. Then, DNA fragments from the same chromosome copy (haplotype) can be identified using the SNP alleles. The CpG sites (or other sites) on this particular chromosome copy (haplotype) can be used for the methylation deconvolution. As the number of CpG sites that can be used for deconvolution would be proportional to the number of SNPs on the homologous chromosome and much bigger than the number of CpG sites linked to a single SNP in the haplotype-based deconvolution analysis, this method would be more precise than the deconvolution analysis using CpG site(s) that are linked to a single SNP. The principle is illustrated in FIG. 12A.

Figure 12A:
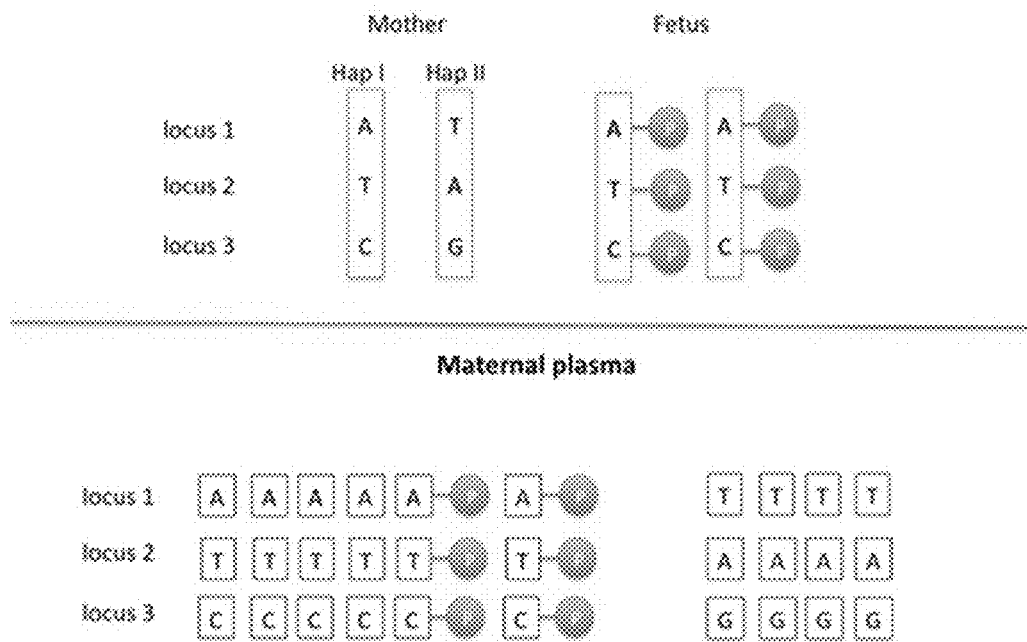
FIG. 12A shows a determination of a maternal haplotype inherited by a fetus using methylation deconvolution according to embodiments of the present invention.

FIG. 12A shows a determination of a maternal haplotype inherited by a fetus using methylation deconvolution according to embodiments of the present invention. In the top part of FIG. 12A, the two haplotypes of the mother and the fetus are shown at three loci that the mother is heterozygous. The two maternal haplotypes are labeled as Hap I and Hap II. In this example, the fetus has inherited Hap I from the mother. For illustration purpose, only the SNP loci that the mother is heterozygous are shown. For illustration purposes, the father is homozygous for each of these loci in this example. However, the same principle extends to scenarios that the father is heterozygous without any change.

In the bottom part of FIG. 12A (labeled Maternal plasma), instances of the two alleles at each locus are shown, with each instance representing a different DNA molecule in the plasma at the locus of interest. Only a small number of DNA molecules are shown for illustration purposes. In this example, the fetal DNA percentage is assumed to be 20%, as shown by 20% of the DNA molecules being marked with a P.

In maternal plasma, the DNA molecules carrying the fetal genotype are derived from the placenta and therefore carrying the placental specific methylation patterns. The circles labeled with "P" represent the CpG sites exhibiting the placental methylation pattern near the heterozygous locus. A read including a heterozygous locus and a neighboring site can be used for measuring a methylation level for detecting the placental methylation pattern. In this example, an objective is to determine if the fetus has inherited Hap I or Hap II from the mother. To achieve this, plasma DNA fragments that carry alleles on Hap I and cover at least one CpG site are selected for methylation deconvolution. As the fetus has inherited Hap I from the mother, the placenta would contribute a significant proportion to this pool of plasma DNA molecules. On the other hand, when the fragments carrying alleles on Hap II are analyzed with methylation deconvolution, a very low contribution from the placenta would be observed.

To illustrate this, we analyzed the maternal plasma sample stated above for Table 6. We focused on a 5-Mb region on chromosome 1. SNPs where the mother was heterozygous and the fetus was homozygous were selected for the analysis. For each of these SNP loci, the alleles that were shared between the mother and the fetus formed one haplotype (denoted as Hap I) and the alleles that were present only on the maternal genome formed another haplotype (denoted as Hap II). Thus, in this example, there are two maternal haplotypes (Hap I and Hap II) and the fetus has inherited Hap I from the mother. In the maternal plasma, the DNA fragments carrying the alleles on Hap I and those carrying the alleles on Hap II were analyzed separately using methylation deconvolution. All the CpG sites on the same plasma DNA molecule of a heterozygous SNP were used for the deconvolution analysis. In this example, none of these CpG sites overlapped with type I or type II markers.

TABLE 7

Methylation deconvolution for Hap I and Hap II.

|  | Hap I | Hap II |
| --- | --- | --- |
| Liver | 0% | 0% |
| Lung | 0% | 6.7% |
| Colon | 3.4% | 6.2% |
| Small intestines | 0% | 10.6% |
| Pancreas | 4.1% | 0% |
| Adrenal glands | 0% | 4.6% |
| Esophagus | 0% | 0% |
| Adipose tissues | 3.7% | 3.6% |
| Heart | 0% | 0% |
| Brain | 6.8% | 10.6% |
| T cells | 6.8% | 21% |
| B cells | 8.9% | 11.7% |
| Neutrophil | 12.7% | 25% |
| Placenta | 53.5% | 0% |

Table 7 shows deconvolution of plasma DNA fragments carrying the alleles on the two maternal haplotypes, namely Hap I and Hap II. The fetus had inherited the maternal Hap I. From this deconvolution analysis, the placenta was deduced to contribute 53.5% of the plasma DNA fragments carrying the alleles on Hap I. On the other hand, there was no contribution from the placenta to the plasma DNA fragments carrying the alleles on Hap II. Therefore, the methylation deconvolution analysis had accurately predicted that the fetus had inherited Hap I from the mother. Greater accuracy may be achieved using CpG sites that overlap with type I and/or type II markers.

As a further example, to demonstrate the practical utility of this approach, another pregnant woman was recruited. Maternal peripheral blood was taken. The blood sample was fractionated into plasma and the cellular components. The maternal buffy coat was analyzed using an Illumina HumanOmni2.5-8 BeadChip array. We used IMPUTE2 (Howie et al. PLoS Genet. 2009; 7:e1000529) to deduce the phase of 851 heterozygous SNPs on a 5 Mb region on the telomeric end of chromosome 1p. The haplotype phasing was based on reference haplotypes of 1000 genomes (mathgen.stats.ox-.ac.uk/impute/1000GP_Phase3.tgz).

After the phased haplotypes were obtained, the CpG sites linked to the two haplotypes were used to perform methylation deconvolution. All the CpG sites on the same plasma DNA molecule of a heterozygous SNP were used for the deconvolution analysis. In this example, none of these CpG sites overlapped with type I or type II markers. Among the 851 SNPs used for the deconvolution, 820 (96.2%) were on intron and intergenic regions. None of them overlapped with CpG islands or shores.

TABLE 8

Methylation deconvolution for Hap I and Hap II.

|  | Hap I | Hap II |
| --- | --- | --- |
| Liver | 0 | 0 |
| Lung | 0 | 5.4 |
| Colon | 0 | 6.2 |
| Small intestine | 0 | 0 |
| Pancreas | 0 | 25 |
| Adrenal glands | 0 | 0 |
| Esophagus | 0 | 0 |
| Adipose tissues | 0 | 17.8 |
| Heart | 0 | 0 |
| Brain | 0 | 0 |
| T cells | 11 | 7.9 |
| B cells | 0 | 0 |
| Neutrophils | 20.2 | 28.4 |
| Placenta | 68.9 | 9.3 |

Table 8 shows a deconvolution of plasma DNA fragments carrying the alleles on the two maternal haplotypes deduced from a panel of reference haplotypes. The two haplotypes are named Hap I and Hap II. The deduced Hap I has significantly higher amount of placental contribution than Hap II, namely, 68.9% versus 9.3%. Thus, the maternal Hap I was deduced to have been inherited by the fetus. The maternal inheritance relied on haplotype deduction was consistent with results from maternal and fetal genotypes.

An advantage of this method is that one is not restricted to SNPs for which the father of the fetus is homozygous and the mother of the fetus is heterozygous. Indeed, in the above example, we had performed the analysis without knowing or deducing the paternal genotype or haplotype. This is an advantage over previously described methods ((Lo et al. Sci Transl Med 2010; 2: 61ra91, U.S. Pat. No. 8,467,976, Fan et al. Nature 2012; 487: 320-324, Kitzman et al. Sci Transl Med 2012; 4: 137ra76).

In some embodiments, a first fractional contribution for a first haplotype can be compared to a reference value derived based on the fetal DNA fraction to determine whether the haplotype has been inherited by the fetus. The cutoffs can be calculated as for example but not limited to 1 time, 1.2 times, 1.4 times, 1.6 times, 1.8 times, 2 times, 2.2 times, 2.4 times, 2.6 times or 2.8 times of the fetal DNA fraction. In this manner, the second fractional contribution for a second haplotype does not need to be determined, if the first fractional contribution is sufficiently large.

In some embodiments, the inherited haplotype may have a deconvoluted fractional concentration double that of the fetal fraction and the non-inherited one has an insignificant contribution. The contribution of the non-inherited haplotype may not have a zero contribution as the paternal haplotypes may give noise to this analysis because some paternal alleles may be the same as the maternal alleles. If the level of noise is high, the fractional contribution of the second haplotype can be determined, and the one with a higher deconvoluted fraction can be deduced to be inherited by the fetus.

Some implementations could test both haplotypes using the reference value, to confirm that only one is inherited. If both appear to be inherited, then the two fractional contributions can be compared to each other. Additionally, if both appear to be inherited, the paternal genome can be checked, as the fetus could have inherited a paternal haplotype that matches the non-inherited maternal haplotype.

In other embodiments, the second fractional contribution can be used to determine the reference value, e.g., the second fractional contribution plus a threshold value. Thus, the reference value can be a sum of the second fractional contribution and a threshold value.

2. Paternal Haplotype

In another embodiment, methylation deconvolution analysis can be applied for the analysis of the paternal haplotype inheritance.

Figure 12B:
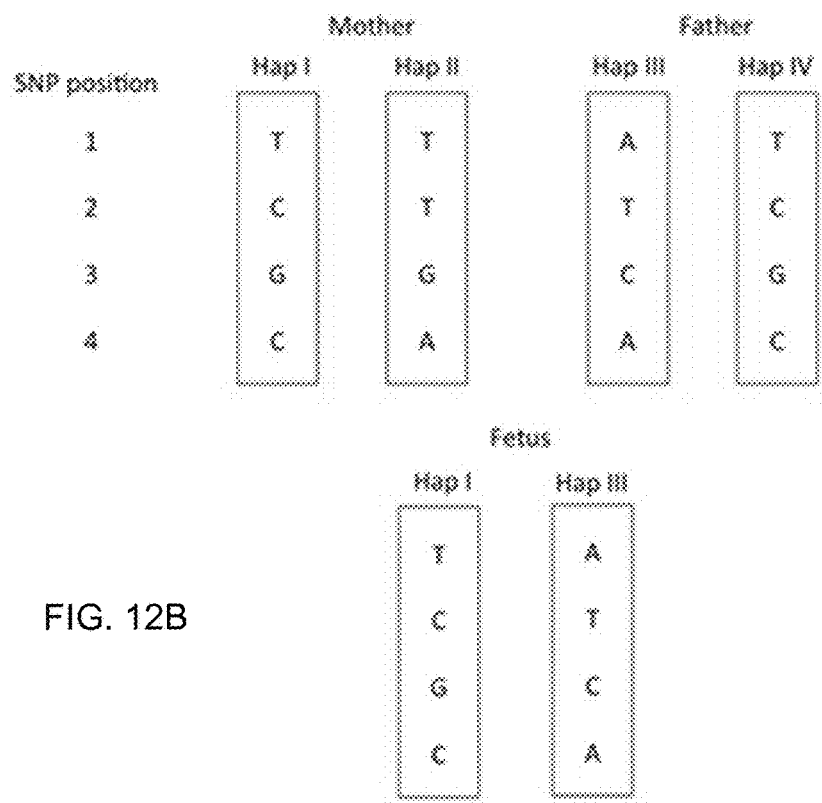
FIG. 12B shows an illustration of the paternal haplotype methylation analysis according to embodiments of the present invention.

FIG. 12B shows an illustration of the paternal haplotype methylation analysis according to embodiments of the present invention. Methylation deconvolution can be performed on the maternal plasma DNA fragments carrying the alleles on paternal Hap III and Hap IV. As Hap III has been inherited by the fetus, the placental contribution would be higher for Hap III compared with Hap IV. Thus, the paternal inheritance of the fetus can be deduced.

This embodiment has advantages over previous methods based on the analysis of paternal-specific alleles. For example, for SNP at position 1, the A allele is present in the father, but not in the mother. Therefore, the detection of the paternal-specific A allele in maternal plasma indicates the inheritance of the Hap III by the fetus. However, for SNP at position 2, both the C and T alleles are not fetal-specific. In this situation, paternal-specific allele analysis cannot be used. However, the methylation deconvolution analysis does not require the presence of paternal-specific allele. Thus, SNPs that are heterozygous in both the father and the mother can be used for the methylation deconvolution analysis of the two paternal haplotypes.

Accordingly, a similar process, as used for maternal haplotypes, can be used to determine which paternal haplotype is inherited. In FIG. 12B, the placental contribution for Hap III would be higher than the placental contribution from Hap IV. The paternal haplotypes can be determined in a same or similar manner as the maternal haplotypes can be determined.

3. Method Using Deconvolution

Figure 13:
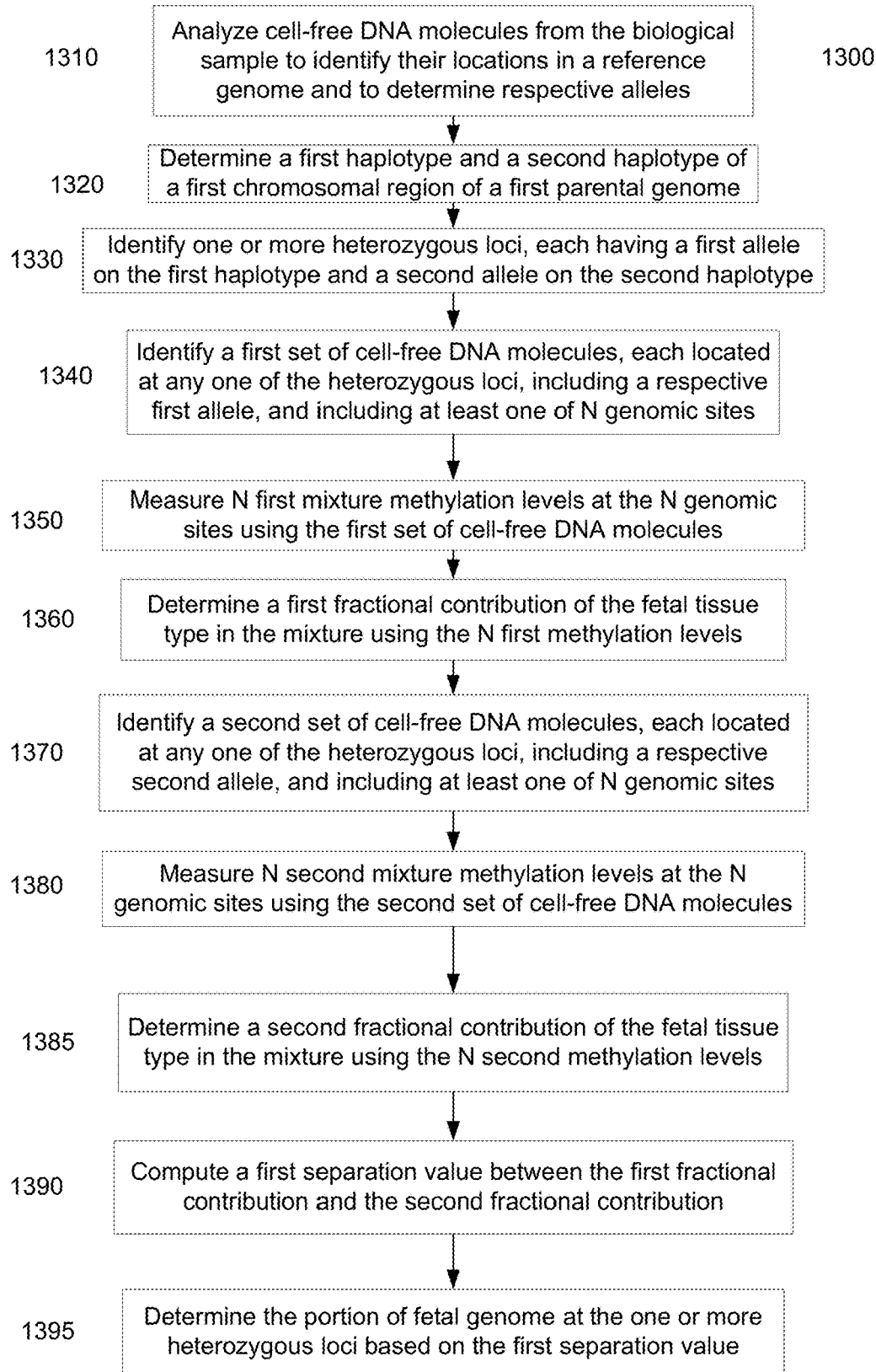
FIG. 13 is a flowchart illustrating a method 1300 of determining a portion of a fetal genome from a maternal sample using methylation deconvolution according to embodiments of the present invention.

FIG. 13 is a flowchart illustrating a method 1300 of determining a portion of a fetal genome from a maternal sample using methylation deconvolution according to embodiments of the present invention. The biological sample includes a mixture of cell-free DNA molecules from a plurality of tissues types, including maternal tissue types and a fetal tissue type. The fetus has a father and a mother being the pregnant female. The portion of the fetal genome can be an entire chromosome copy or just part of the chromosome copy. The determined portions of the fetal genome can be combined to provide information on different portions of the fetal genome, up to the entire fetal genome.

At block 1310, a plurality of cell-free DNA molecules from the biological sample are analyzed. Block 1310 can be performed using techniques described in block 140 of method 100 of FIG. 1. For example, at least 1,000 cell-free DNA molecules can be analyzed to determine where the cell-free DNA molecules are located, and methylation levels can be measured as described below. Further, the cell-free DNA molecules are analyzed to determine a respective allele of the cell-free DNA molecule. For example, an allele of a DNA molecule can be determined from a sequence read obtained from sequencing or from a particular probe that hybridizes to the DNA molecule, where both techniques can provide a sequence read (e.g., the probe can be treated as the sequence read when there is hybridization).

At block 1320, a first haplotype and a second haplotype of a first chromosomal region of a first parental genome of a first parent of the fetus are determined. One skilled in the art will be aware of various techniques to determine haplotypes of a parent. The haplotypes may be determined from the same sample as used to determine methylation levels below or from a different sample. In some implementations, the haplotypes can be determined from cellular samples, e.g., the buffy coat of a blood sample or the tissue of another organ. Examples of determining haplotypes are provided in U.S. Pat. No. 8,467,976, which is incorporated by reference in its entirety. The first parent can be the mother or the father. Other examples of methods for detecting the parental haplotypes include, but not limited to the methods described by Fan et al (Nat Biotechnol 2011; 29: 51-57), Snyder et al (Nat Rev Genet 2015; 16: 344-358), the GemCode technology from 10X Genomics (www.10xgenomics.com/), and Targeted Locus Amplification (TLA) technology from Cergentis (www.cergentis.com/).

At block 1330, one or more heterozygous loci are identified from the first and second haplotypes. Each heterozygous locus has a corresponding first allele in the first haplotype and a corresponding second allele in the second haplotype. The one or more heterozygous loci may be a first plurality of heterozygous loci, where a second plurality of heterozygous loci can correspond to a different chromosomal region.

At block 1340, a first set of the plurality of cell-free DNA molecules is identified. Each of the plurality of cell-free DNA molecules is located at any one of the heterozygous loci from block 1330 and includes a corresponding first allele, so that the cell-free DNA molecule can be identified as corresponding to the first haplotype. It is possible for a cell-free DNA molecule to be located at more than one of the heterozygous loci, but typically a read would only include one heterozygous locus. Each of the first set of cell-free DNA molecules also includes at least one of N genomic sites, where the genomic sites are used to measure the methylation levels. N is an integer, e.g., greater than or equal to 2, 3, 4, 5, 10, 20, 50, 100, 200, 500, 1,000, 2,000, or 5,000. Thus, a read of a cell-free DNA molecule can indicate coverage of 1 site, 2 sites, etc.

At block 1350, N first mixture methylation levels are measured at the N genomic sites (e.g., CpG sites) using the first set of the plurality of cell-free DNA molecules. One first mixture methylation level can be measured for each of the N genomic sites. Block 1350 can be performed in a similar manner as block 150 of method 100 of FIG. 1. In some embodiments, the measurement of the methylation level of a DNA molecule can use methylation-aware sequencing results, which may also be used to determine the location and respective allele of the DNA molecule. One skilled in the art will be aware of the various techniques that can be used to determine a methylation status of a site on a DNA molecule.

At block 1360, a first fractional contribution of the fetal tissue type in the mixture is determined using the N first methylation levels. In some embodiments, block 1360 can be performed via blocks 160 and 170 of method 100 of FIG. 1. Thus, a fractional contribution can be determined simultaneously for a panel of M tissue types. Block 1360 may use N issue-specific methylation levels at N genomic sites, determined for each of M tissue types, e.g., as in block 120 of method 100 of FIG. 1.

At block 1370, a second set of the plurality of cell-free DNA molecules is identified. Each of the plurality of cell-free DNA molecules is located at any one of the heterozygous loci from block 1330 and includes a corresponding second allele, so that the cell-free DNA molecule can be identified as corresponding to the second haplotype. Each of the second set of cell-free DNA molecules also includes at least one of the N genomic sites, where the genomic sites are used to measure the methylation levels.

At block 1380, N second mixture methylation levels at the N genomic sites are measured using the second set of the plurality of cell-free DNA molecules. Block 1380 may be performed in a similar manner as block 1350.

At block 1385, a second fractional contribution of the fetal tissue type in the mixture is determined using the N second methylation levels. Block 1385 may be performed in a similar manner as block 1360.

At block 1390, a first separation value is computed between the first fractional contribution and the second fractional contribution. Examples of separation values are described herein, e.g., including a difference or a ratio.

At block 1395, the portion of fetal genome is determined at the one or more heterozygous loci based on the first separation value. Thus, an inherited haplotype of the first parent can be determined. For example, the first separation value can be a ratio of the first fractional contribution and the second fractional contribution. The portion of the fetal genome can be determined to have one or more copies of the first haplotype and no copies of the second haplotype when the ratio is greater than a threshold value. Examples of threshold values include but not limited to 1.3, 1.4, 1.5, 1.6, 1.8, 2.0, 2.2, 2.4, 2.6, 2.8 and 3.0. The portion of the fetal genome can be determined to have one or more copies of the second haplotype and no copies of the first haplotype when the ratio is less than a threshold value. Examples of threshold values include but not limited to 0.1, 0.2, 0.3, 0.4, 0.5, 0.6, 0.7 and 0.8. The portion of the fetal genome can be determined to have the first haplotype and the second haplotype when the ratio is equal to one within a cutoff value. Examples of cutoff values include but not limited to 0.85, 0.9, 0.95, 1.0, 1.05, 1.1 and 1.15. Both haplotypes might be inherited when both parents have a same haplotype in the region being analyzed.

As another example, the first separation value is a difference of the first fractional contribution and the second fractional contribution. The portion of the fetal genome can be determined to have one or more copies of the first haplotype and no copies of the second haplotype when the difference is greater than a threshold value. Examples of threshold values include but not limited to 1%, 1.5%, 2%, 2.5%, 3%, 4%, 5%, 6%, 7%, 8%, 10%, 12%, 14%, 16%, 18% and 20%. The portion of the fetal genome can be determined to have one or more copies of the second haplotype and no copies of the first haplotype when the difference is less than a threshold value, e.g., where the threshold value is a negative number.

The inherited haplotype of the other parent can also be determined. For example, a second plurality of heterozygous loci of the first chromosomal region can be identified in the genome of the other parent. Fractional contributions can be determined for each of the other parent's haplotypes, and a separation value can be used to determine the inherited haplotype of the other parent.

For example, the first plurality of heterozygous loci and the second plurality of heterozygous loci can be the same loci or be different. Each of the second plurality of heterozygous loci can include a corresponding third allele in a first haplotype of the other parent (e.g., a first paternal haplotype) and a corresponding fourth allele in a second haplotype of the other parent (e.g., a second paternal haplotype). The third and fourth alleles can be the same as the first and second alleles. In addition to the first and second set of cell-free DNA molecules for the first parent, a third plurality of cell-free DNA molecules can each be located at any one of the second plurality of heterozygous loci, include the corresponding third allele of the heterozygous locus, and include at least one of K genomic sites. The K genomic sites may be the same or different than the N genomic sites used for the first parent. In a similar manner as with the first parent, K third mixture methylation levels can be measured at the K genomic sites using the third set of the second plurality of cell-free DNA molecules, and a third fractional contribution of the fetal tissue type in the mixture can be determined using the K third methylation levels. The third fractional contribution corresponds to the first haplotype of the other parent (e.g., the first paternal haplotype).

A fourth set of the plurality of cell-free DNA molecules can each be located at any one of the second plurality of heterozygous loci, include the corresponding fourth allele of the heterozygous locus, and include at least one of the K genomic sites. Thus, the fourth set of DNA can be used to test the second haplotype of the other parent. K fourth mixture methylation levels at the K genomic sites can be measured using the fourth set of the second plurality of cell-free DNA molecules, and a fourth fractional contribution of the fetal tissue type in the mixture can be determined using the K fourth methylation levels. A second separation value can be computed between the third fractional contribution and the fourth fractional contribution, and the portion of fetal genome at the second plurality of heterozygous loci can be determined based on the second separation value. The inherited haplotype from the other parent can be determined in a similar manner as for the first parent. The fourth fractional contribution corresponds to the second haplotype of the other parent (e.g., the second paternal haplotype).

In some embodiments, the second fractional contribution does not need to be determined. Instead, a haplotype can be determined to be inherited if the corresponding fractional contribution is sufficiently high. For example, the first fractional contribution can be compared to a reference value to determine whether the fetus inherited the first haplotype at the first chromosomal region. The fetus can be determined to have inherited the first haplotype at the first chromosomal region when the first fractional contribution exceeds the reference value.

In other embodiments, the reference value may be determined from the second fractional contribution. For example, the reference value can be a sum of the second fractional contribution and a threshold value. The sum with the threshold value can ensure that the first fractional contribution is sufficiently greater than the second fractional contribution.

A separate determination of inheritance can be made for the second haplotype by comparing the second fractional contribution to the reference value to determine whether the fetus inherited the second haplotype at the first chromosomal region. The fetus can be determined to have inherited the second haplotype at the first chromosomal region when the second fractional contribution exceeds the reference value. If both the fractional contributions are determined to exceed the reference value, the two fractional contributions can be compared to each other to determine if one is significantly greater than the other (e.g., using a threshold). The haplotypes of the other parent can be determined to identify whether one of these haplotypes is the same as the haplotypes of the first parent, thereby explaining that both haplotypes of the first parent could have been inherited.

C. Determination of Inherited Haplotype Using Methylation Levels

Other embodiments can use the general hypomethylation of cell-free fetal DNA to identify the inherited haplotype as the one with the lower overall methylation level. Embodiments can start with deduced maternal or paternal haplotypes, and then measure the methylation levels of plasma DNA molecules containing SNP alleles in each of those deduced haplotypes. In one implementation of analyzing the maternal haplotypes, the methylation levels of the two deduced maternal haplotypes can be compared, and the one with the lower methylation level would be predicted to be the haplotype inherited by the fetus. In another implementation of analyzing the paternal haplotypes, the methylation levels of the two deduced paternal haplotypes can be compared, and the one with the lower methylation level would be predicted to be the haplotype inherited by the fetus.

1. Example

As an example, a methylation level of each of the two maternal haplotypes can be determined. As the placental tissue is relatively hypomethylated compared with other tissues, it is expected that the maternal haplotype inherited by the fetus would be more hypomethylated than the one that is not inherited by the fetus. The methylation densities were tested in the maternal plasma using the actual haplotypes of the mother, which were deduced using the maternal, paternal, and fetal genotypes.

TABLE 9

Methylation densities for actual Hap I and Hap II.

|  | Hap I | Hap II |
|---|---|---|
| Overall methylation densities | 65% | 87% |

Table 9 shows methylated densities of the two maternal haplotypes in the maternal plasma. As Hap I was the actual haplotype inherited by the fetus by genotyping, the results of the methylation analysis of the haplotype correctly identified the inheritance.

In other embodiments, the maternal haplotypes can be deduced based on the genotypes of the mother alone, or reference haplotypes of the population from haplotype database can also be used for this analysis. The maternal haplotypes used in this example were phased using the IMPUTE2 program. Thus, deduced maternal haplotypes can also be used in this analysis.

TABLE 10

Methylation densities for deduced Hap I and Hap II.

|  | Hap I | Hap II |
|---|---|---|
| Overall methylation densities | 68% | 76% |

Table 10 shows methylated densities of the two deduced maternal haplotypes in the maternal plasma. The deduced maternal haplotype that was inherited by the fetus had lower methylation densities. An example of a statistical procedure that one can use to determine whether one haplotype has a sufficiently lower methylation density includes the chi-square test. A separation between the two methylation levels can be required to be sufficiently large (e.g., greater than a threshold) to make the determination. If the separation is not sufficient, then an indeterminate classification can be made. In some embodiments, a determination of an inheritance of both haplotypes can be determined if the separation is not sufficiently large and if both methylation levels are below a threshold level, which may be characterized by inclusion of fetal DNA. For example, tables 9 and 10 indicate that a methylation density below 70% may indicate that the fetus has inherited that haplotype. Both haplotypes may be inherited when the parents share a haplotype for the region being analyzed.

In another embodiment, the overall methylation densities of the maternal plasma DNA carrying the paternal Hap III and Hap IV can be compared. Similar to the maternal haplotype analysis, the fetus would be deduced as having inherited the paternal haplotype that has lower overall methylation densities.

2. Method Using Methylation Levels

Figure 14:
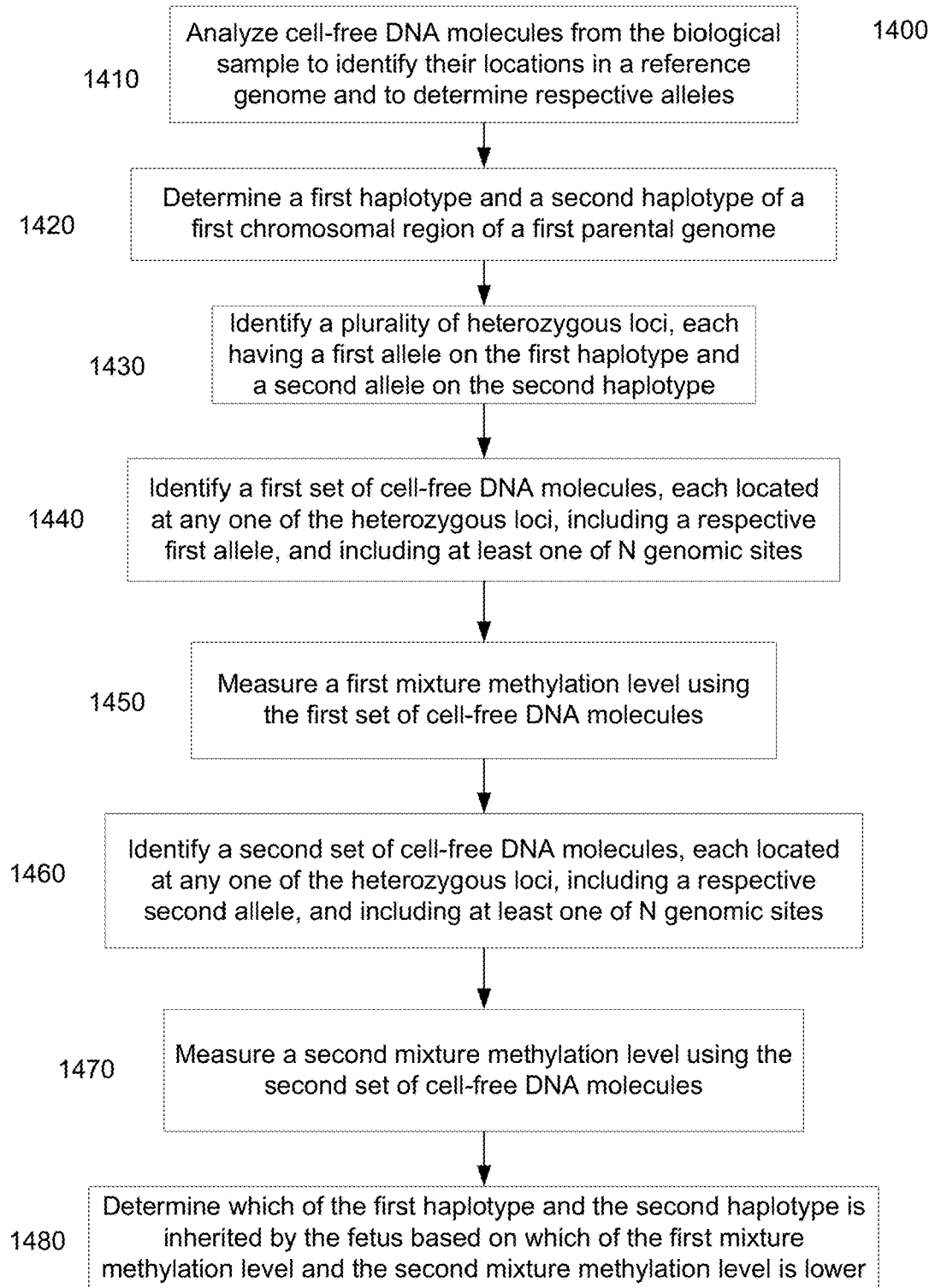
FIG. 14 is a flowchart illustrating a method 1400 of determining a portion of a fetal genome from a maternal sample using methylation levels according to embodiments of the present invention.

FIG. 14 is a flowchart illustrating a method 1400 of determining a portion of a fetal genome from a maternal sample using methylation levels according to embodiments of the present invention. The biological sample includes a mixture of cell-free DNA molecules from a plurality of tissues types, including maternal tissue types and a fetal tissue type. The fetus has a father and a mother being the pregnant female. The portion of the fetal genome can be an entire chromosome copy or just part of the chromosome copy. The determined portions of the fetal genome can be combined to provide the entire fetal genome, as with other methods described herein.

At block 1410, a plurality of cell-free DNA molecules from the biological sample are analyzed. Block 1410 can be performed in a similar manner as block 1310 of method 1300 of FIG. 13.

At block 1420, a first haplotype and a second haplotype of a first chromosomal region are determined of a first parental genome of a first parent of the fetus. Block 1420 can be performed in a similar manner as block 1320 of FIG. 13. In some embodiments, genotypes of the first parent's genome can be determined at the plurality of heterozygous loci using a sample from the first parent, e.g., a blood sample or other tissue that may or may not include fetal DNA. A plurality of reference haplotypes can be obtained, e.g., from databases of reference genomes. The first haplotype and the second haplotype can be deduced using the genotypes and the plurality of reference haplotypes. For example, the alleles of each genotype can be compared against the reference haplotypes, and any haplotypes that do not include the alleles at the corresponding locus can be discarded. Once two reference haplotypes remain, those haplotypes can be identified as being the first haplotype and the second haplotype.

At block 1430, a plurality of heterozygous loci is identified from the first and second haplotypes. Each heterozygous locus has a first allele in the first haplotype and a second allele in the second haplotype.

At block 1440, a first set of the plurality of cell-free DNA molecules is identified. Block 1440 can be performed in a similar manner as block 1340 of FIG. 13.

At block 1450, a first mixture methylation level is measured using the first set of the plurality of cell-free DNA molecules. For example, the first mixture methylation level may be a methylation density for the cell-free DNA molecules of the first set. The methylation density can be computed as a total methylation density for all of the cell-free DNA molecules of the first set. In another example, separate methylation densities can be computed for each locus, and the separate methylation densities can be combined to obtain the first mixture methylation level, e.g., an average of the separate methylation densities.

At block 1460, a second set of the plurality of cell-free DNA molecules is identified. 1460 can be performed in a similar manner as block 1370 of FIG. 13.

At block 1470, a second mixture methylation level is measured using the second set of the plurality of cell-free DNA molecules. For example, the second mixture methylation level may be a methylation density for the cell-free DNA molecules of the second set.

At block 1480, it is determined which of the first haplotype and the second haplotype is inherited by the fetus based on which of the first mixture methylation level and the second mixture methylation level is lower. As part of block 1480, a separation value can be determined between the first mixture methylation level and the second mixture methylation level, and compared to a threshold value. The threshold value can ensure that the lower level is sufficiently lower. The threshold value can be determined using the chi-square test. For example, measurements can be taken of samples where the inherited haplotype is known, and a distribution of the separation values can be determined, and a threshold value can be selected that accurately determines the inherited haplotype in the training data obtained from the samples. Methods 1300 and 1400 can also be combined, with each being performed as a check, and the inherited haplotype determined if both methods are consistent with each other.

D. Selection of Loci

Various embodiments can be used for the comparison of the methylation levels or the fraction contributions of the two deduced maternal haplotypes in the maternal plasma. In one embodiment, the number of SNP loci to be analyzed can be determined before the analysis. For example, the number of SNP loci used in the haplotype deconvolution analysis can be determined according to a number of factors, for example, but not limited to the desired statistical power, the mean difference in methylation levels in the placenta and blood cells in the region of interest, and the number of molecules being analyzed for each SNP.

The size of the region of interest can be fixed, and all SNPs within the region of interest can be used in the analysis. The size of the region of interest can be determined taking into account a number of factors, for example, but not limited to the desired statistical power, the mean difference in methylation level in the placenta and blood cells in the region of interest, the number of molecules being analyzed for each SNP, and the chance of meiotic recombination with the region of interest.

In other embodiments, the number of SNPs and the size of the region to be analyzed are not determined before the analysis. For example, the number of SNPs can be sequentially increased until the data are sufficient to arrive at a statistically significant conclusion concerning which maternal haplotype is statistically significantly less methylated than the other one. For instance, the SNPs on the region of interest can be arranged in an ascending order of their genomic coordinates. Then statistical testing can be carried out with the data of the SNP with the lowest number of genomic coordinate. If this is sufficient to make a conclusion regarding which haplotype is less methylated statistically, then a conclusion is made. Similarly, the SNPs can be arranged in a descending order, with a highest number of genomic coordinate that is sufficient being used.

If the statistical accuracy is not sufficient, another statistical comparison can be performed starting from the next SNP with a higher number of genomic coordinates. On the other hand, if the data of the first SNP are not sufficient for one to conclude that one haplotype is less methylated than the other one (or that the separation value between fractional contributions is not sufficiently large), the data of another SNP can be added and another round of statistical testing is carried out. This procedure can be continued until the accumulated data are sufficient to make a statistically significant conclusion. A number of statistical tests can be performed to compare the methylation levels of the two haplotypes, for example, but not limited to Student's t-test, Mann-Whitney rank-sum test and Chi-square test. The level of statistical significance can be determined based on the desired confidence of the conclusion, for example, but not limited to adopting a P-value of 0.05, 0.01, 0.001, 0.0001, or 0.00001.

E. Combinations with RHDO

In some embodiments, results generated by the RHDO analysis of U.S. Pat. No. 8,467,976 can be combined with present methylation embodiments to arrive at a more accurate procedure for diagnosis or to reduce an amount of sequencing required. For example, fetal haplotypes can be determined using present embodiments and using results of the RHDO analysis of U.S. Pat. No. 8,467,976, and the determined fetal haplotypes from both of the techniques can be compared. For example, the results from the two analyses would be accepted only if they are concordant. Further analysis can be performed if the two analyses show different conclusions, e.g., measurements can be repeated at higher depth of coverage on the genome.

For such a combined approach to be most cost-effective, it is preferred to have one type of sequencing that can yield data for both methods. In one embodiment, this can be done by a single molecule method that would generate sequencing as well as methylation information, e.g. using the Single Molecule Real Time sequencing technology from Pacific Biosciences, or nanopore sequencing (e.g. from Oxford Nanopore Technologies). These are two examples of methylation-aware sequencing. In another embodiment, the RHDO analysis can be performed on bisulfite sequencing results. For such an embodiment, any maternal and paternal genetic information can be determined also using bisulfite sequencing. Bisulfite sequencing is thus another example of methylation-aware sequencing. Furthermore, other methylation aware sequencing technologies can be used, such as oxidative bisulfite sequencing (Booth et al. Science 2012; 336: 934-937) or Tet-assisted bisulfite sequencing (Yu et al. Cell 2012; 149: 1368-1380). The latter examples would allow one to analyze the 5-methylcytosine distribution of the analyzed DNA molecules.

F. Uses of Knowledge of Fetal Genome

The noninvasive prenatal analysis of the fetal genome can be used to determine if a fetus has inherited a disease from the parents. This is particularly useful for the detection of monogenic diseases, for example congenital adrenal hyperplasia (New et al. J Clin Endocrinol Metab 2014; 99:E1022-30), beta-thalassemia (Lam et al. Clin Chem. 2012; 58:1467-75) and hereditary muscular dystrophies (Genet Med 2015; 17:889-96). If a monogenic disease is detected, various treatments can be performed, e.g., the pregnancy can be terminated, treatment provided before pregnancy, or after birth. For example, steroid treatment can be given prenatally to a pregnant woman confirmed of having a fetus affected by congenital adrenal hyperplasia to avoid abnormal sexual development.

VI. Haplotype Deconvolution Analysis for Aneuploidy Detection

The haplotype deconvolution can also be used to detect a sequence imbalance of a chromosomal region of a fetus, such as aneuploidies, microdeletions, or microamplifications (e.g., microduplications). For example, a fractional contribution of a haplotype in one region can be compared to a fractional contribution of another haplotype in another region.

A. Mother

Figure 15:
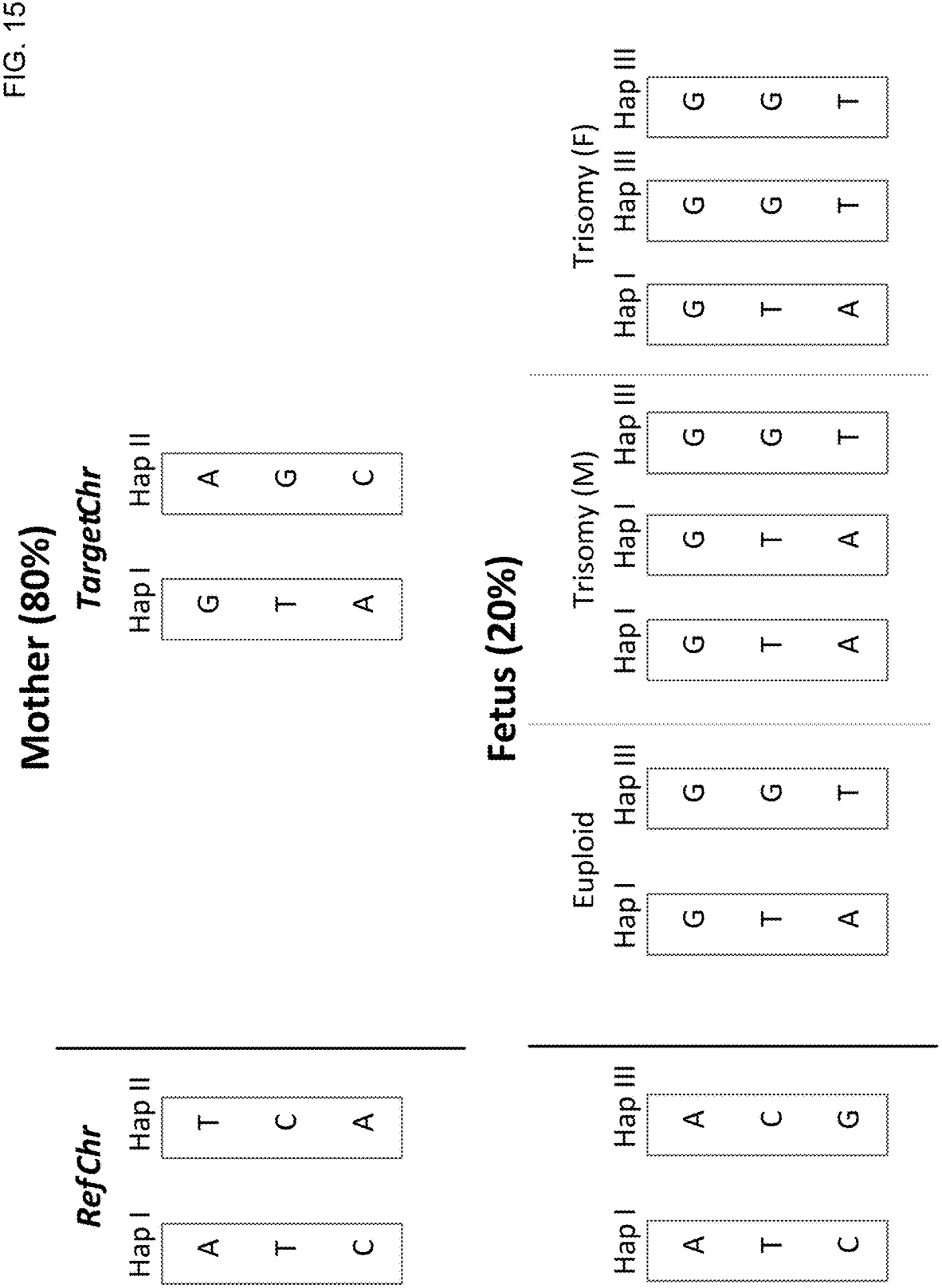
FIG. 15 shows chromosomal aneuploidy detection based on haplotype deconvolution for maternal haplotypes according to embodiments of the present invention.

FIG. 15 shows a chromosomal aneuploidy detection based on haplotype deconvolution for maternal haplotypes according to embodiments of the present invention. In this illustration, the mother has two maternal haplotypes, namely Hap I and Hap II. For illustration purposes, we assume that 80% of her plasma DNA was derived from her own cells and 20% was derived from the placenta, which are example percentages in commonly measured ranges. This method can be generally applied for pregnancies with different fetal DNA percentages. Knowledge of the fetal DNA percentage is not required, but is simply provided for illustration, although a measurement of the fetal DNA percentage may be performed in various ways, e.g., using fetal-specific alleles or fetal-specific methylation markers.

The fetus has inherited Hap I and another haplotype from the father, namely Hap III. The placentally-derived DNA would exhibit the fetal genotypes, and a sequence imbalance can be detected by analyzing the fractional contribution resulting from the placentally-derived DNA.

As illustrated above, the fetal inheritance of the maternal haplotype can be determined through the deconvolution of the two maternal haplotypes. Analysis for the placental contribution to the maternal DNA can be performed for each of the two maternal haplotypes. The maternal haplotype inherited by the fetus (Hap I in this example) would have a much higher placental contribution compared with the maternal haplotype that is not inherited by the fetus (Hap II). The placental contribution for Hap I would be positively correlated with the fetal DNA fraction in the maternal plasma.

After determining which maternal haplotype has been inherited by the fetus, the dosage of the chromosome the fetus has inherited from the mother can be further determined through maternal haplotype deconvolution. In this illustration, two chromosomal regions are analyzed using maternal haplotype deconvolution. In one embodiment, the reference chromosome (RefChr) is a chromosome or a chromosomal region which is unlikely to be affected by a chromosomal aneuploidy. The reference chromosomal region is shown on the left side of FIG. 15. The target chromosome (TargetChr) is a chromosome or a chromosomal region which is potentially affected by a chromosomal aneuploidy. The target chromosomal region is shown on the right side of FIG. 15. The two regions can be for different regions of a same chromosome or for regions of two different chromosomes.

In the example shown, the fetus has been deduced to have inherited Hap I from the mother for both the reference chromosome and target chromosome through the methylation deconvolution of the Hap I and the Hap II at each region. Then, the placental contribution to maternal plasma DNA for Hap I can be compared between the reference chromosome and the target chromosome. If the placental contribution of Hap I for the target chromosomal region is significantly different than the placental contribution of Hap I for the reference chromosomal region (e.g., higher for amplification or lower for deletion), then a sequence imbalance can be identified.

For illustration purpose, we use the detection of trisomy as an example. However, other types of chromosome aneuploidies, including monosomy, amplification of a subchromosomal region or deletion of a subchromosomal region can also be detected using this method. For trisomy, the extra copy of the affected chromosome can be inherited from the father (denoted as Trisomy (F)) or the mother (denoted as Trisomy (M)). In over 90% of trisomy 21 cases, the extra copy of chromosome 21 is derived from the mother (Driscoll et al. N Engl J Med 2009; 360: 2556-2562). In the scenario of Trisomy (M), the placental contribution of Hap I for the target chromosome would be higher than that for the reference chromosome. In FIG. 15, Trisomy (M) is shown with two instances of Hap I, which would provide a higher placental contribution for the target region than the one instance of Hap I for the reference region.

Whether the placental contribution of Hap I for the target chromosome is higher than that for the reference chromosome can be determined by comparing a separation value between the two placental contributions and a threshold, which may be based on a separate measurement of the fetal DNA percentage. A higher fetal DNA percentage would result in a higher expected separation value between the two placental contributions, and thus the threshold can be set higher. For example, with the fetal DNA percentage being 20%, the placental contribution of Hap I for the reference region would be about 20% and the placental contribution of Hap I for the target region would be about 36.4%.

For instance, assume that 10 DNA molecules exist at the reference chromosome, then two of them are fetal and eight of them are maternal. For the two fetal DNA molecules, one is derived from Hap I and one is derived from Hap III. For the eight maternal DNA molecules, four are Hap I and four are Hap II. For the target region, there would be an extra DNA molecule of Hap I from the fetus. Thus there would be two fetal Hap I DNA molecules and 4 maternal Hap I DNA molecules total, providing 2/6=33.3%. The threshold value for the difference (e.g., 13.3%) can be placed between 0 and 13.3% to provide optimal specificity and sensitivity. A distribution of separation values can be determined from a reference group of samples. In the scenario of Euploid, the placental contributions would be approximately equal, e.g., the separation value would be less than the threshold. One skilled in the art will know how to select a suitable threshold based on the description herein and in U.S. Pat. No. 8,467,976, and other references cited herein.

In one embodiment, the ratio (or other separation value) of placental contribution of Hap I between the target and reference chromosomes for a group of pregnant women, each known to be carrying a euploid fetus can be used as a reference interval. The ratio in the tested case can be compared with this reference group to determine if a significant elevation of placental contribution of Hap I is present for the target region relative to the reference region. In the example of 20% fetal DNA, the ratio would be 33.3/20=1.67. The ratio can be generalized to $2/(1+f)$, where f represents the fetal DNA fraction. In another embodiment, the difference in the placental contribution of Hap I between the target and the reference chromosomes can be determined. This difference is then compared with a reference group.

B. Father

In another embodiment, haplotype deconvolution of the paternal haplotypes (Hap III and Hap IV) can be performed in the maternal plasma. The analysis of the paternal haplotypes can be performed in a similar manner as for the maternal haplotypes.

Figure 16:
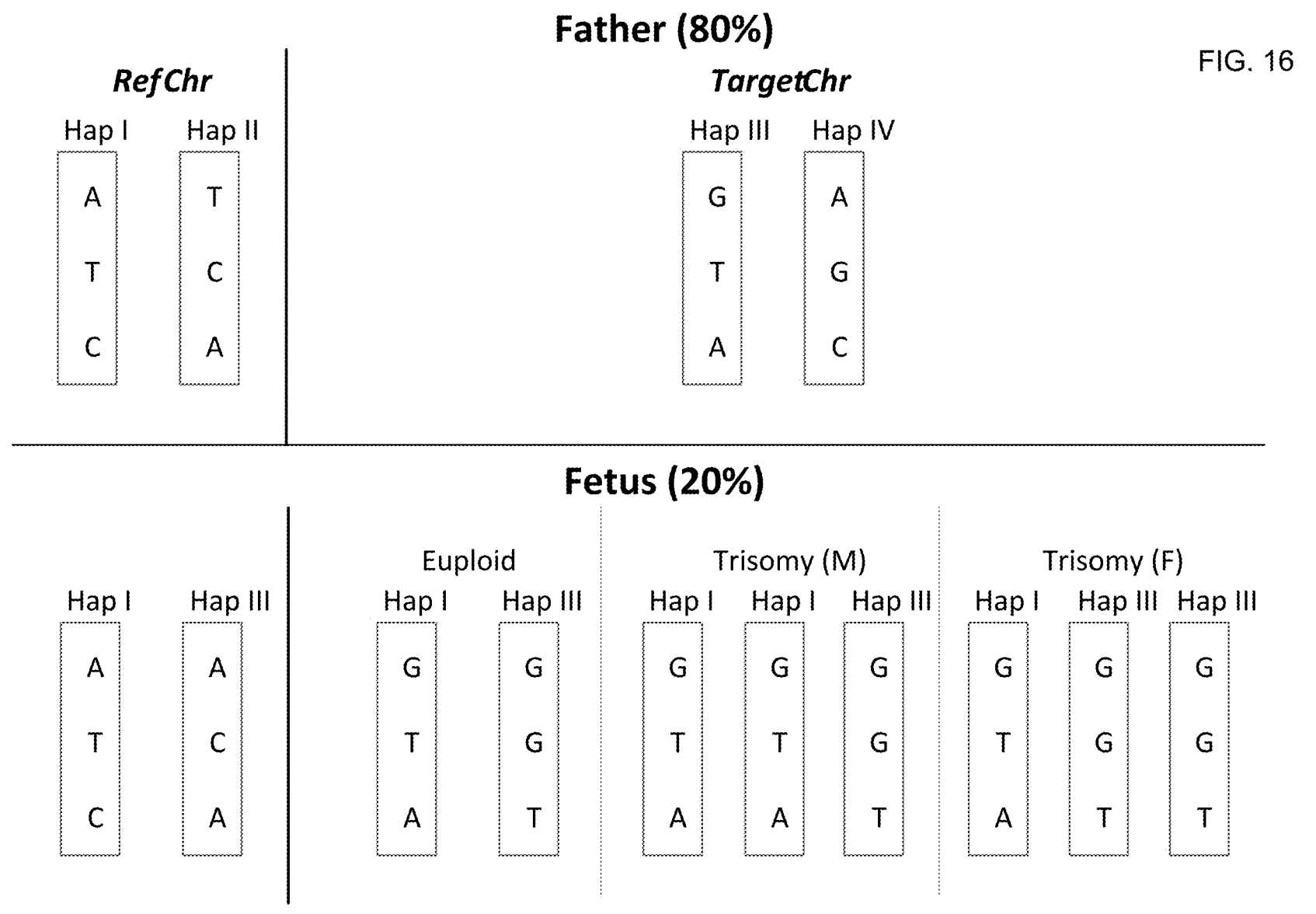

FIG. 16 shows a chromosomal aneuploidy detection based on haplotype deconvolution for paternal haplotypes according to embodiments of the present invention. In this illustration, the father has two paternal haplotypes, namely Hap III and Hap IV. As in FIG. 15, the fetus has inherited Hap I from the mother and Hap III from the father.

In the scenario where the extra copy of chromosome is derived from the father (Trisomy (F)), the placental contribution of Hap III would be higher for the target chromosome than for the reference chromosome. This is shown for the Trisomy (F) example, where two copies of Hap III are shown. As described above for the maternal haplotypes, a separation value between the placental contributions of Hap III for the target and reference regions can be compared to a threshold to determine whether an extra copy of Hap III exists for the target region. In various embodiments, a ratio or difference of the two placental contributions of the tested case can be compared with a reference group of pregnant women, each known to be carrying a euploid fetus so as to determine if the fetus has a chromosomal trisomy for the target chromosome, or amplification or deletion of a target chromosomal region. The threshold can be based on the separation values for the reference group of euploid fetuses, a reference group of aneuploidy fetuses, or both. A separate measure of fetal DNA percentage can also be used, as is described herein.

C. Method of Detecting a Sequence Imbalance

Figure 17:
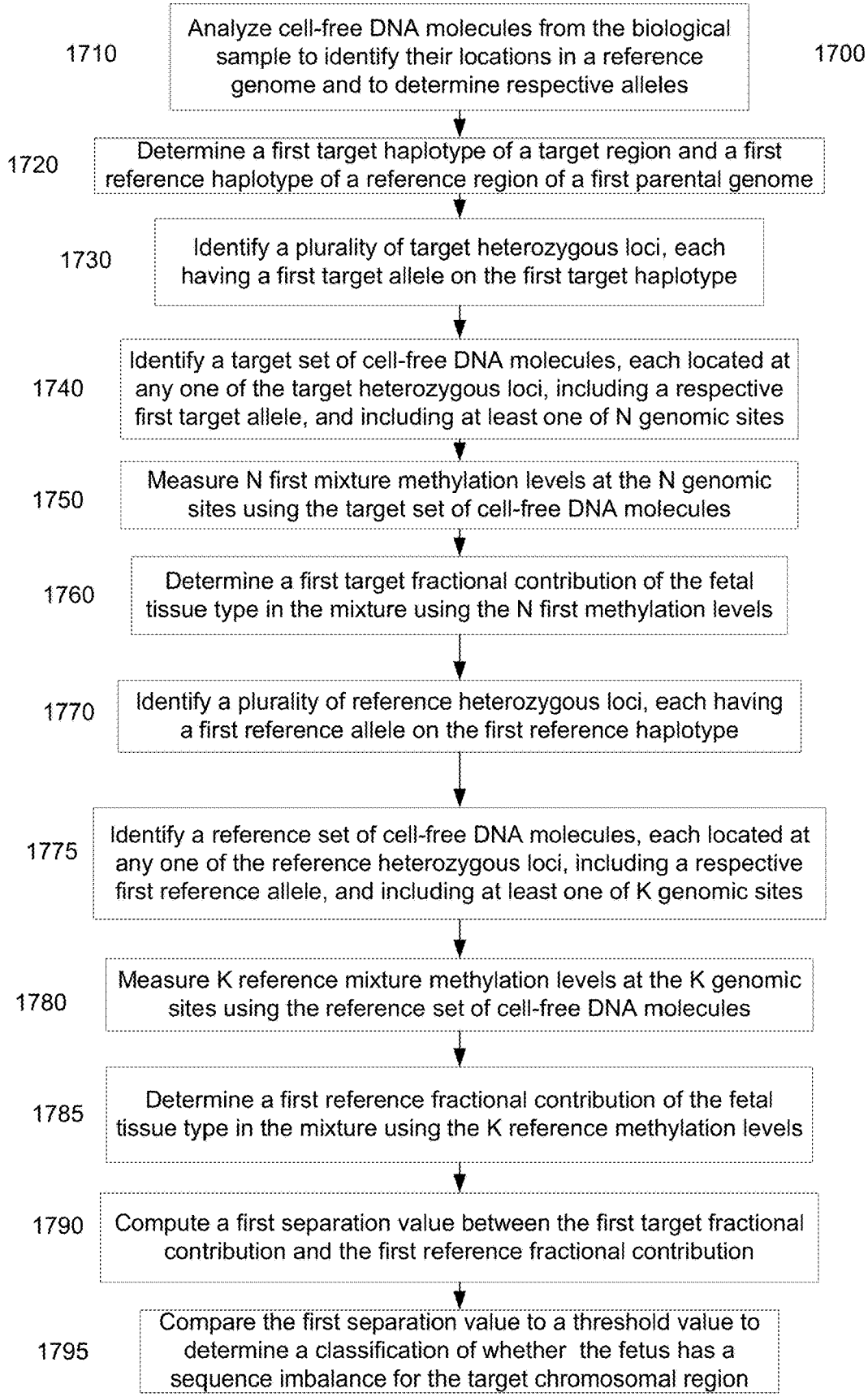
FIG. 17 is a flowchart of a method 1700 for detecting a sequence imbalance in a portion of a fetal genome of an unborn fetus of a pregnant female using a biological sample from the pregnant female according to embodiments of the present invention.

FIG. 17 is a flowchart of a method 1700 for detecting a sequence imbalance in a portion of a fetal genome of an unborn fetus of a pregnant female using a biological sample from the pregnant female according to embodiments of the present invention.

At block 1710, a plurality of cell-free DNA molecules from the biological sample are analyzed. Block 1710 can be performed in a similar manner as block 1310 of method 1300 of FIG. 13.

At block 1720, a first target haplotype of a target chromosomal region of a first parental genome of a first parent of the fetus is determined, and a first reference haplotype of a reference chromosomal region of the first parental genome is determined. Block 1720 can be performed in a similar manner as block 1320 of FIG. 13. The target chromosomal region and the reference chromosomal region can be an entire chromosome or just part of a chromosome. Thus, the target chromosomal region can be a first chromosome and the reference chromosomal region can be a second chromosome different from the first chromosome. The first parent can be the mother or the father of the fetus.

The target chromosomal region can be selected based on various criteria. For example, a plurality of target regions can be selected, as may occur to test many non-overlapping regions of a specified size, such as 1 Mb, 5 Mb, 10 Mb, 20 Mb, 50 Mb, etc. As another example, the target chromosomal region can be selected based on a copy number analysis that identifies the region as having more DNA molecules than expected, e.g., as described in U.S. Patent Publications 2009/0029377 and 2011/0276277.

In some embodiments, it can be determined that the fetus has inherited the first target haplotype from the first parent and that the fetus has inherited the first reference haplotype from the first parent. The determination can include embodiments of FIG. 13 or FIG. 14. For example, determining that the fetus has inherited the first target haplotype from the first parent can include determining a second target fractional contribution of the fetal tissue type in the mixture corresponding to the second target haplotype, computing a second separation value between the first target fractional contribution and the second target fractional contribution, and determining that the fetus has inherited the first target haplotype from the first parent based on the second separation value.

At block 1730, a plurality of target heterozygous loci are identified of the target chromosomal region of the first parental genome. Each target heterozygous locus includes a corresponding first target allele in the first target haplotype and a corresponding second target allele in a second target haplotype of the first chromosomal region of the first parental genome. Referring back to the example of FIG. 15, the target heterozygous loci have corresponding first target alleles of {G,T,A} on Hap I and have corresponding second target alleles of {A,G,C} on Hap II.

At block 1740, a target set of the plurality of cell-free DNA molecules is identified. Each cell-free DNA molecule of the target set is located at any one of the target heterozygous loci, includes a corresponding first target allele, and includes at least one of N genomic sites in the target chromosomal region. Block 1740 can be performed in a similar manner as described herein. For example, sequence reads can be mapped to a reference genome, where the target set of plurality of cell-free DNA molecules aligns to any one of the target heterozygous loci.

At block 1750, N first mixture methylation levels are measured at the N genomic sites using the target set of the plurality of cell-free DNA molecules. Block 1750 can be performed in a similar manner as block 1350 of FIG. 13.

At block 1760, a first fractional contribution of the fetal tissue type in the mixture is determined using the N first methylation levels. Block 1760 can be performed in a similar manner as block 1360 of FIG. 13.

At block 1770, a plurality of reference heterozygous loci are identified for the reference chromosomal region of the first parental genome. Each reference heterozygous locus includes a corresponding first reference allele in the first reference haplotype and a corresponding second reference allele in a second reference haplotype of the reference chromosomal region of the first parental genome. Referring back to the example of FIG. 15, the reference heterozygous loci have corresponding first target alleles of {A,T,C} on Hap I and have corresponding second target alleles of {T,C,A} on Hap II.

At block 1775, a reference set of the plurality of cell-free DNA molecules is identified. Each cell-free DNA molecule of the reference set is located at any one of the reference heterozygous loci, includes a corresponding first reference allele, and includes at least one of K genomic sites in the reference chromosomal region.

At block 1780, K reference mixture methylation levels are measured at the K genomic sites using the reference set of the plurality of cell-free DNA molecules.

At block 1785, a first reference fractional contribution of the fetal tissue type is determined in the mixture using the K reference methylation levels.

At block 1790, a first separation value is computed between the first target fractional contribution and the first reference fractional contribution.

At block 1795, the first separation value is compared to a threshold value to determine a classification of whether the fetus has a sequence imbalance for the target chromosomal region. If the first separation value exceeds the threshold value then a sequence imbalance can be identified. The threshold value can be determined as described above, e.g., based on separation values seen in a reference group of samples not having a sequence imbalance and/or a reference group of samples having the sequence imbalance. As examples, the classification can be positive, negative, or indeterminate for the sequence imbalance being tested.

Different threshold values can be used, depending on the type of sequence imbalance. For example, if the sequence imbalance is a deletion, then the first separation value would be expected to be a negative value. In such a case, the threshold value can be a negative number, and the comparison can determine that the first threshold value exceeds the threshold value by being a larger negative number. If the sequence imbalance being tested is an amplification, then it can be tested whether the separation value is greater than the threshold value. Thus, the threshold value used can be dependent on the type of sequence imbalance being tested.

VII. Deconvolution of Signatures to Identify Diseased Tissue

If a genomic signature (e.g., a particular SNP allele) is known, embodiments can determine which tissue is the origin of such signatures. As the cell-free DNA molecules exhibiting the signatures are from the tissue of origin, the tissue of origin can be identified from the fractional contributions determined using cell-free DNA molecules exhibiting the signatures. Thus, cell-free DNA molecules with a signature of a transplanted organ (e.g., a signature of a haplotype of the transplanted organ) can be used to monitor changes in amounts of cell-free DNA molecules from the transplanted organ with high sensitivity, e.g., given that a high fractional contribution of the DNA in the mixture would be from the transplanted organ. Examples are provided for transplants to show that the technique is accurate. In another example, a signature of a tumor can be used to identify tissues within which the tumor resides.

A. Organ Transplantation

As an example for organ transplantation, we analyzed the plasma of a patient who had received liver transplantation and a patient who had received bone marrow transplantation. For each case, the donor-specific SNP alleles were identified through the genotyping of the tissues from the patients and the donors. For the liver transplant recipient, a biopsy of the donor liver and the blood cells of the recipient were sequenced. For the bone marrow transplant case, the buccal swab (recipient genotype) and the blood cells (donor genotype) were sequenced. The plasma DNA samples were sequenced after bisulfite conversion. Sequenced DNA fragments carrying a donor-specific SNP allele and at least one CpG site were used for downstream methylation deconvolution analysis. A total of 72 million and 121 million reads were sequenced for the patients who had received liver and bone marrow transplantation, respectively. For the two cases, 38 and 5355 fragments were used for deconvolution analysis, respectively.

TABLE 6

Fractional contributions for different organs to plasma DNA fragments carrying donor-specific alleles in the two transplant recipients.

| Tissue type | Liver transplant recipient | Bone marrow transplant recipient |
|---|---|---|
| Liver | 45.4 | 4.4 |
| Lung | 0.0 | 1.5 |
| Colon | 29.3 | 6.3 |
| Small intestines | 0.0 | 1.8 |
| Pancreas | 0.0 | 0.0 |
| Adrenal glands | 0.0 | 0.0 |
| Esophagus | 0.0 | 0.0 |
| Adipose tissues | 0.0 | 14.8 |
| Heart | 0.0 | 0.0 |
| Brain | 14.5 | 9.6 |
| T-cells | 0.0 | 12.3 |
| B-cells | 5.9 | 16.6 |
| Neutrophils | 4.9 | 32.8 |

Table 6 shows methylation deconvolution analysis on plasma DNA fragments carrying donor-specific alleles in a liver transplant recipient and a bone marrow transplant recipient. The numbers represent the percentage contribution of different tissues to the donor-specific plasma DNA fragments. For the liver transplant case, the liver was shown to be the most important contributor to these DNA fragments. For the bone marrow transplant case, the hematopoietic system (including the T-cells, B-cells and neutrophils) was the major contribution of the donor-specific DNA fragments. These results indicate that methylation deconvolution can accurately indicate the tissue origin of DNA fragments having single nucleotide alterations. A small amount of sequenced fragments were attributed to other tissues probably because of measurement imprecision as relatively small number of donor-specific fragments were used for the deconvolution analysis.

The fractional contributions for tissue associated with the transplanted organ can be determined in the above manner and monitored. With the baseline fractional contribution (an example of a reference fractional contribution) relatively high as a result of using only cell-free DNA molecules exhibiting the donor signature, small changes in total amount of donor DNA in plasma can be detected. Accordingly, methylation deconvolution analysis can be applied for the monitoring of organ transplantation.

As can be seen above for the liver transplant, methylation deconvolution is not absolutely specific. In this analysis, plasma DNA fragments carrying the donor-specific alleles were used for methylation deconvolution analysis. These fragments are specific for the donor and should be derived only from the liver in this liver transplant recipient. Therefore, the theoretical contribution of the liver should be 100%. Another possibility is that certain cell types are present in different types of tissues making the liver methylation profile overlapping with other tissues. For example, the connective tissue cells in the liver may also be present in other organs. But, relative percentages from other patients or other samples (e.g., at other times) of the instant patient can identify whether more cell-free DNA molecules are being released.

In various embodiments, the donor signature can correspond to a particular haplotype of the donor genome or both haplotypes in a chromosomal region. Methylation deconvolution can be performed using cell-free DNA molecules located on the particular donor haplotypes, and increases in the fractional contribution of the particular haplotype can be monitored. If a significant increase occurs (e.g., as measured by a percentage or absolute threshold), then a rejection of the transplanted organ can be identified.

Figure 18:
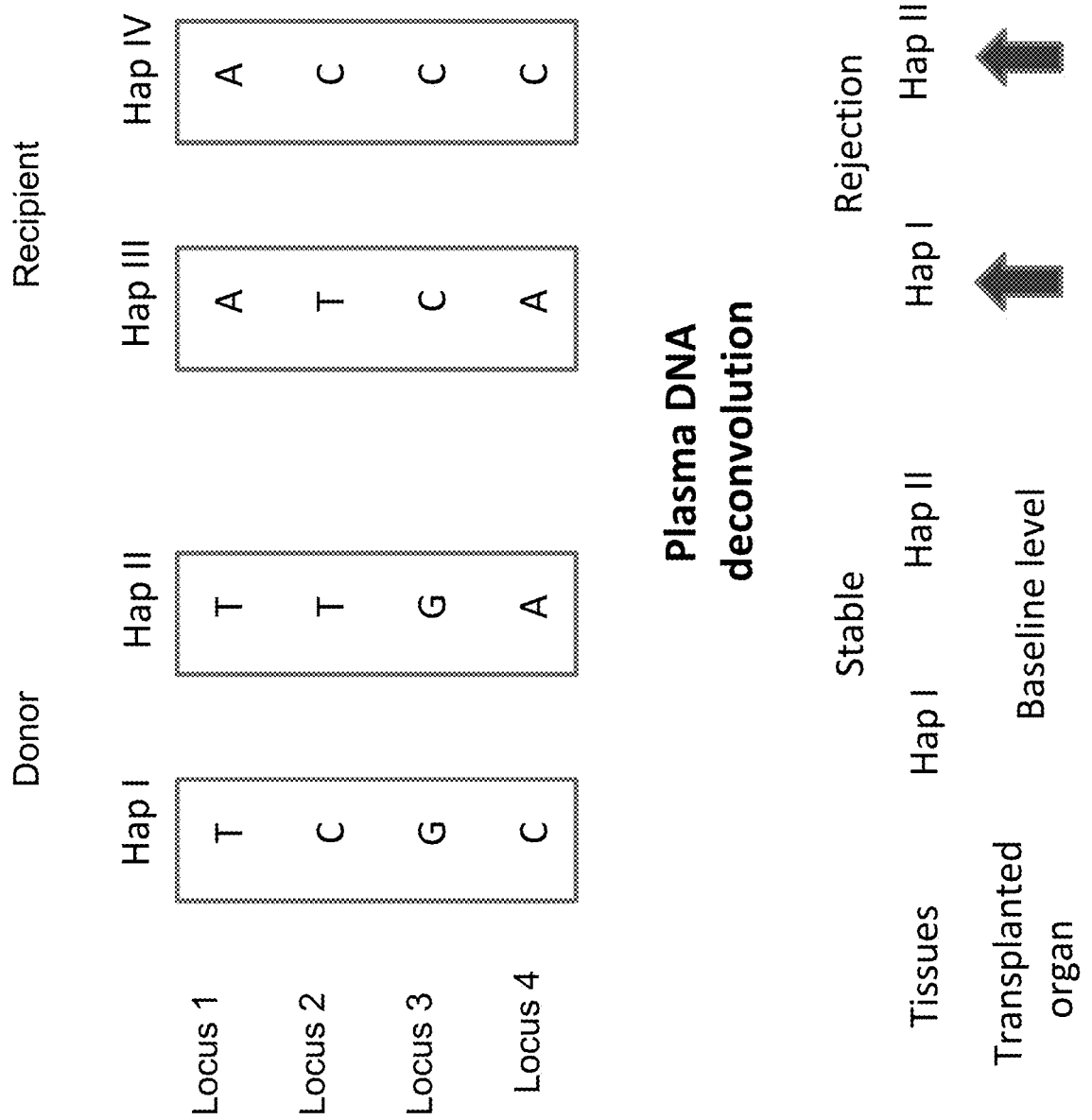
FIG. 18 shows an illustration of haplotype deconvolution for organ transplant monitoring according to embodiments of the present invention.

FIG. 18 shows an illustration of haplotype deconvolution for organ transplant monitoring according to embodiments of the present invention. The donor has haplotypes labeled Hap I and Hap II, and the recipient has haplotypes labeled Hap III and Hap IV. The donor has a signature at locus 1 and locus 3, as the alleles are not found on the recipient haplotypes. Locus 2 and locus 4 do not have a donor signature. Thus, embodiments may use DNA molecules that are located at locus 1 and locus 3 as part of a deconvolution process.

The plasma DNA deconvolution can be used to determine whether the determined fractional contribution from the transplanted organ is at a baseline or increased relative to the baseline. In some embodiments, the fractional contributions can be determined for each of Hap I and Hap II separately, if different signatures exist; such different signatures can exist at different loci. In other embodiments, a single fractional contribution can be determined for both haplotypes, e.g., when they share a signature. In the example shown in FIG. 18, Hap I and Hap II do share a signature at locus 1 and locus 3.

Accordingly, the contribution of the transplanted organ can be determined using haplotype deconvolution. The increase in the contribution of the haplotype to the transplanted organ would be useful to indicate the increased contribution of the organ to the plasma DNA. In various embodiments, the baseline level can be determined from a cohort of transplant recipients not having rejection or from a cohort of transplant recipients having rejection. When using recipients having rejection, the baseline level can be determined as below those from a cohort of transplant recipients having rejection.

As mentioned above, the donor may have two identical haplotypes or the recipient can also have two identical haplotypes. Furthermore, the donor and recipient may share a haplotype. As long as the donor or the recipient has a unique haplotype, a change in a percentage of cell-free DNA molecules from the donor tissue can be determined. In the former, a rejection will be detected when one sees an increase in the contribution of the donor-unique haplotype in plasma (or other sample). In the latter, a rejection will be detected when one sees a decrease in the contribution of the recipient-unique haplotype in plasma.

Accordingly, some embodiments can use a first haplotype that is present in normal cells of the organism and not being present in abnormal cells that may be in the mixture. This would correspond to the latter example above, when the recipient has a unique haplotype. Another example is when a patient has a unique haplotype in healthy cells compared to a tumor (e.g., previously found in the organism). In this embodiment, the first tissue type can be determined to have the disease state when the first separation value is less than the threshold value.

In some embodiments, if the transplanted organ is detected as being rejected, treatment can be provided. For example, a change is dosage of anti-rejection medication can be provided. As another example, a new organ can be obtained, and surgery can be performed to remove the old transplanted organ and put in the new transplanted organ.

B. Hepatocellular Carcinoma (HCC)

As an example for determining a tissue of origin for a cancer signature or aberration (or monitoring for a tumor that was known to exist or have existed), we analyzed the plasma of an HCC patient. The tumor and the blood cells of the patients were sequenced to identify the cancer-specific single nucleotide mutations. Sequenced DNA fragments carrying a cancer-specific mutation and at least one CpG site were used for downstream methylation deconvolution analysis. A total of 11,968 fragments were used for deconvolution analysis. In addition to the methylation profiles from the normal tissue organs, we have also included the methylation profile of HCC tissues as candidate tissue of origin.

In another embodiment, more types of tumor tissues can be considered as candidate tissues for the mutations. In one embodiment, the methylation profiles of the common cancers, for example but not limited to colorectal cancer, lung cancer, breast cancer, pancreatic cancer, prostate cancer, bladder cancer, cervical cancer and ovarian cancer can be included as candidate tissues. In yet another embodiment, only the most possible cancers specific to the patient can be included in the analysis. For example, in female patients, the breast cancer, ovarian cancer, colorectal cancer and cervical cancer are considered. In yet another embodiment, the ethnic origin and the age are considered in the selection of the candidate tissues.

Table 7 shows methylation deconvolution of the plasma DNA fragments carrying cancer-associated mutations. The deconvolution analysis accurately determined that the DNA fragments carrying cancer-associated mutations are predominantly derived from the liver cancer tissues.

TABLE 7

Fractional contributions for HCC patient using cancer mutation.

| Tissue | Contribution (%) |
|---|---|
| Liver | 0.0 |
| Lung | 0.0 |
| Colon | 0.0 |
| Small intestines | 0.0 |
| Pancreas | 0.0 |
| Adrenal glands | 0.0 |
| Esophagus | 0.0 |
| Adipose tissues | 0.0 |
| Heart | 0.0 |
| Brain | 0.0 |
| T-cells | 0.0 |
| B-cells | 0.0 |
| Neutrophil | 4.6 |
| Liver cancer | 95.4 |
| Placenta | 0.0 |

In some embodiments, the tumor can initially be identified by detecting a copy number aberration, e.g., as described in U.S. Pat. Nos. 8,741,811 and 9,121,069. The particular tissue of origin can be determined, e.g., as described in U.S. patent application Ser. No. 14/994,053 (U.S. Publication 2016/0201142) based on patterns of copy number aberrations previously identified in various tumors. Once the tumor has been identified, treatment can be performed, e.g., by surgery, radiotherapy, or chemotherapy. Either way, a biopsy can be obtained after the tissue of origin is determined. A cancer-specific point mutation can be determined from the biopsy or from DNA fragments in plasma (e.g., as described in U.S. patent Publication 2014/0100121, or other mixtures that are associated with the copy number aberration.

After treatment, a key change would be the disappearance of the genomic aberrations, including the copy number aberration and point mutation. When these aberrations are gone, the analysis of the genomic signature of the point mutation in the affected regions would give a change in the tissue contribution via the methylation deconvolution analysis. If the tumor comes back in the future, the cancer-associated changes in tissue composition (as determined using methylation deconvolution analysis) would be seen again. For example, the fractional contribution can be compared to a reference fractional contribution, and if a change is detected, then new courses of treatment can be provided.

In various embodiments, the cancer-specific mutation can be on only one haplotype or on both haplotypes, e.g., in a manner similar to the donor example above. Thus, as with the donor, the fractional contributions can be determined for each of Hap I and Hap II separately, if different signatures exist; such different signatures can exist at different loci. In other embodiments, a single fractional contribution can be determined for both haplotypes, e.g., when they share a signature.

C. Imprinting

In another embodiment, the haplotype deconvolution analysis can be applied for the analysis of the genomic regions showing tissue-specific imprinting. It has been shown that the differential methylation of the paternally and maternally inherited alleles in different tissue organs is a common phenomenon (Baran et al. Genome Res 2015; 25:927-36). Haplotype deconvolution would be useful for the monitoring of the contribution of the organ exhibiting tissue-specific imprinting. For example, when the paternally and maternally inherited haplotypes have different methylation status in the liver but not in other tissues, methylation deconvolution can be performed on both the paternally and maternally inherited haplotypes. In one embodiment, both the paternal and maternal methylation patterns can be included as candidate tissues in the analysis.

D. Method Using Genomic Signature

Figure 19:
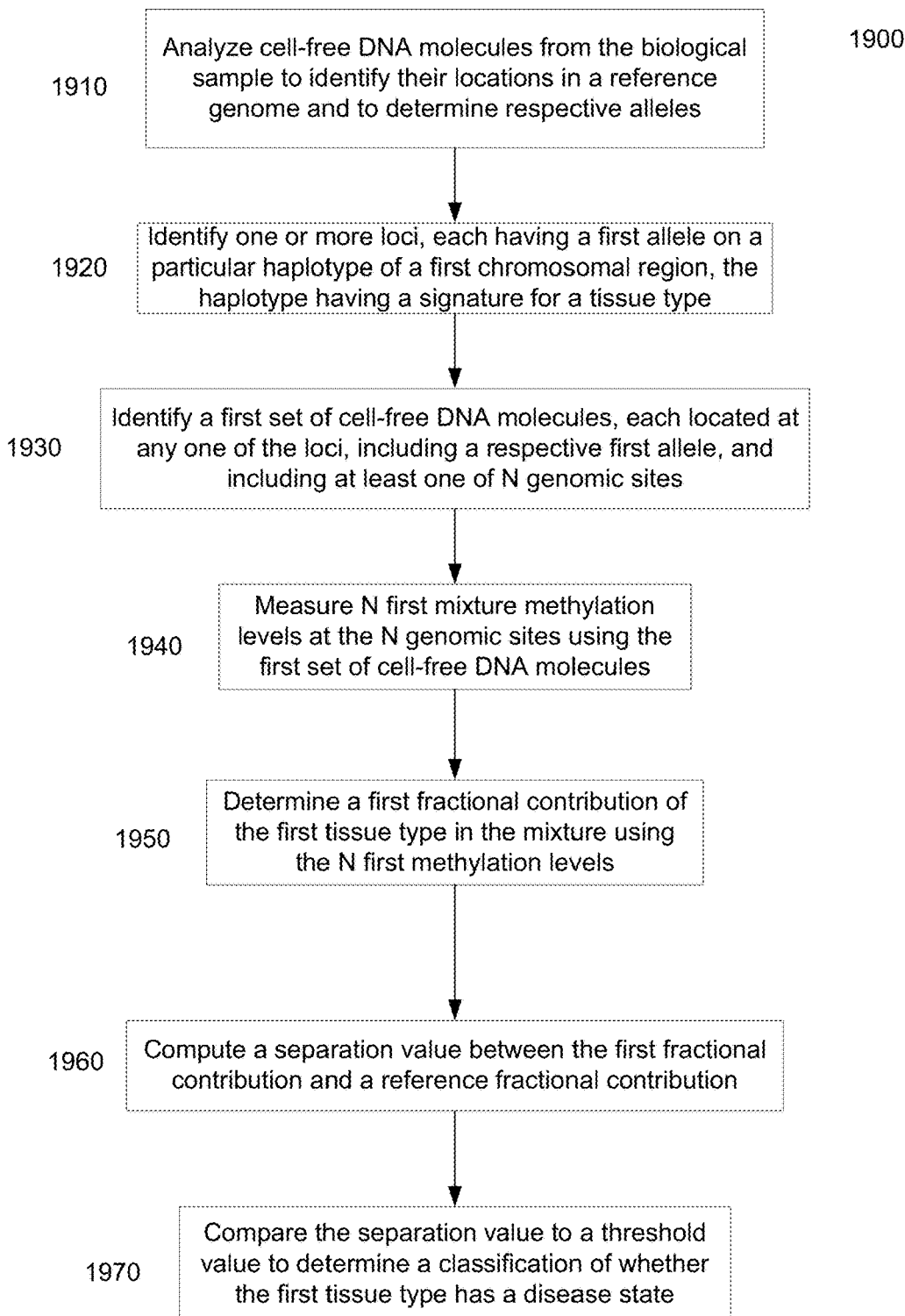
FIG. 19 is a flowchart illustrating a method of analyzing a biological sample of an organism to detect whether a first tissue type has a disease state associated with a first haplotype according to embodiments of the present invention.

FIG. 19 is a flowchart illustrating a method 1900 of analyzing a biological sample of an organism to detect whether a first tissue type has a disease state associated with a first haplotype according to embodiments of the present invention. The biological sample includes a mixture of cell-free DNA molecules from a plurality of tissues types, including a first tissue type. Method 1900 is performed at least partially using a computer system.

At block 1910, a plurality of cell-free DNA molecules from the biological sample are analyzed. Block 1910 can be performed using techniques described in block 140 of method 100 of FIG. 1. For example, at least 1,000 cell-free DNA molecules can be analyzed to determine where the cell-free DNA molecules are located, and methylation levels can be measured as described below. Further, the cell-free DNA molecules are analyzed to determine a respective allele of the cell-free DNA molecule. For example, an allele of a DNA molecule can be determined from a sequence read or from a particular probe that hybridizes to the DNA molecule.

At block 1920, one or more loci are identified. Each locus has a first allele on a first haplotype of a first chromosomal region. The first haplotype has a property of either: (1) not being present in healthy cells of the organism, but instead may be from a tumor or transplanted tissue, as examples; or (2) being present in normal cells of the organism and not being present in abnormal cells that may be in the mixture. Thus, the first haplotype has a genomic signature. In this manner, there is a difference between the healthy (normal) cells and the abnormal cells, thereby allowing embodiments to track a fractional contribution of one or the other, or both, so as to track an extent (e.g., fractional contribution) of the abnormal cells. With property (1), the first haplotype is associated with a disease state, e.g., cancer or a rejection of transplanted tissue. Thus, a particular cancer can have the first haplotype in a cancer genome of the particular cancer.

The one or more first alleles may be identified at the one or more loci on the first haplotype by obtaining a tissue sample (e.g., of the tumor or transplanted tissue) and analyzing DNA molecules of the tissue sample to determine the first haplotype. Such a tissue sample may be obtained from a biopsy, and method 1900 can be used to test if the cancer has metastasized to other tissues, or has recurred after surgery. Each one of the loci may be a heterozygous locus or a homozygous locus in the abnormal cells. For example, in FIG. 18, locus 1 and locus 3 are homozygous in the donor organ. But, ultimately, more than one allele would be observed in the plasma for all the loci, as each locus would have a signature for healthy cells or for abnormal cells. Thus, two haplotypes would exist across the tissue types, but a single tissue type might have only one haplotype in a region being analyzed.

At block 1930, a first set of the plurality of cell-free DNA molecules is identified. Each of the plurality of cell-free DNA molecules is located at any one of the loci from block 1920 and includes a corresponding first allele at the one locus, so that the cell-free DNA molecule can be identified as corresponding to the first haplotype. Each of the first set of cell-free DNA molecules also includes at least one of N genomic sites, where the genomic sites are used to measure the methylation levels. N is an integer, e.g., greater than or equal to 2, 3, 4, 5, 10, 20, 50, 100, 200, 500, 1,000, 2,000, or 5,000.

At block 1940, N first mixture methylation levels are measured at the N genomic sites using the first set of the plurality of cell-free DNA molecules. One first mixture methylation level can be measured for each of the N genomic sites. Block 1940 can be performed in a similar manner as block 150 of method 100 of FIG. 1. In some embodiments, the measurement of the methylation level of a DNA molecule can use methylation-aware sequencing results, which may also be used to determine the location and respective allele of the DNA molecule.

At block 1950, a first fractional contribution of the first tissue type in the mixture is determined using the N first methylation levels. In some embodiments, block 1950 can be performed via blocks 160 and 170 of method 100 of FIG. 1. Thus, a fractional contribution can be determined simultaneously for a panel of M tissue types. Block 1950 may use N issue-specific methylation levels at N genomic sites, determined for each of M tissue types, e.g., as in block 120 of method 100 of FIG. 1.

At block 1960, a separation value between the first fractional contribution and a reference fractional contribution is computed. Examples of separation values are described herein. The reference fractional contribution can be determined using samples from organisms that are healthy for the first tissue type. For a transplant example, the reference fractional contribution can be determined from one or more measurements of biological samples of organisms whose transplanted first tissue is not being rejected.

At block 1970, the separation value can be compared to a threshold value to determine a classification of whether the first tissue type has a disease state. For example, if the first haplotype is associated with cancer, then an appreciable first fractional contribution indicates that the first tissue type has cancer, as can be measured by the separation value exceeding the threshold value (e.g., when the reference fractional contribution is zero). The amount that the first fractional contribution exceeds the threshold value can indicate a certain level of cancer. As another example, the first haplotype can be specific to transplanted tissue, and a high contribution relative to the reference can indicate the organism is rejecting the transplanted tissue.

In an embodiment where the first haplotype is present in normal cells of the organism and not present in abnormal cells that may be in the mixture, the first tissue type can be determined to have the disease state when the first separation value is less than the threshold value. An example of a disease state is preeclampsia which can be associated with a spectrum of pathologic changes in a fetal tissue such as the placenta. As an example, in such a situation, if the first haplotype is specific to the fetus, e.g. paternally inherited haplotype, it may be increased in the maternal plasma in a pregnancy complicated with preeclampsia.

In some embodiments, a second haplotype for the diseased tissue, e.g., the transplanted tissue or a tumor may also be used. Thus, a second fractional contribution can be computed and compared to the reference fractional contribution. Accordingly, a second set of the plurality of cell-free DNA molecules can each be located at any one of the one or more loci, include a corresponding second allele on a second haplotype of the first chromosomal region, and include at least one of the N genomic sites. The second haplotype would have the same property of being only from healthy cells or abnormal cells.

A plurality of tissue types can be tested (e.g., using method 100 of FIG. 1), so as to determine a tissue of origin of the first haplotype, e.g., when it is associated with cancer. Accordingly, fractional contributions of other tissue types in the mixture can be determined using the N first methylation levels, and corresponding separation values between the corresponding fractional contributions and respective reference fractional contribution can be compared to the threshold value to determine a classification of whether each of the other tissue types has the particular cancer. Different tissue could have different reference fractional contributions.

VIII. Identifying Tissue of Origin of CNA of Cancer

In some embodiments, an origin of a tumor may not be known. Thus, it can be difficult to identify point mutations in a tumor, as may be used for method 1900 of FIG. 19 or other methods described herein. Additionally, a tumor may not have a significant number of point mutations, but may have chromosomal regions exhibiting amplifications and deletions (examples of copy number aberrations).

To address this problem, embodiments can use a copy number analysis to identify regions that exhibit a copy number aberration (CNA). Typically, a CNA occurs on only one haplotype of a region. As only one haplotype has an amplification or a deletion, there will be a relatively large difference between the fractional contributions of the tissue type within which the tumor resides.

The CNA analysis may be performed in a variety of ways, e.g., as described in U.S. Pat. Nos. 8,741,811 and 9,121,069. For example, the human genome (or genome for other type of organism) can be partitioned into approximately 3,000 non-overlapping 1-Mb bins. The number of reads mapping to each 1-Mb bin can be determined. After correcting for GC bias (Chen E Z, et al. (2011) *PLoS One* 6(7):e21791), the sequence read density of each bin can be calculated. For each bin, the sequence read density of the test case can be compared to the values of the reference control subjects. Copy number gains and losses may be defined as 3 standard deviations above and below, respectively, the mean of the controls. Accordingly, identifying a first chromosomal region as exhibiting a copy number aberration can be based on a first amount of cell-free DNA molecules that are located in the first chromosomal region.

To determine the tissue origin of copy number aberrations in plasma, plasma DNA tissue mapping can be performed using the methylation markers located within the genomic regions exhibiting such aberrations in plasma. In the examples below for the cancer patients, mapping of plasma DNA copy number aberrations was performed only in cases with aberrations affecting a contiguous chromosome region of at least 30 Mb so that a sufficient number of methylation markers could be used for mapping.

A. Identifying Regions with Copy Number Aberration (CNA)

A 62-year-old male patient with HCC was recruited from the Department of Surgery, Prince of Wales Hospital, Hong Kong with informed consent. Ten milliliters of venous blood were collected in EDTA tubes at diagnosis and 3 months after the resection of the tumor. The blood samples were centrifuged at 3000 g for 10 minutes to separate the blood cells from the plasma. The plasma was recentrifuged at 30000 g for 10 minutes to remove the remaining cells.

DNA extracted from the blood cells was used for phasing the SNPs to construct the haplotypes of the patient using the 10x genomics platform following the manufacturer's instruction. High molecular weight DNA was extracted from blood or tissue samples using MagAttract HMW DNA kit (QIagen, Germany). The quality of DNA was verified by Genomic DNA Analysis ScreenTape on a 4200 TapeStation system (Agilent, Germany). DNA was quantified by dsDNA HS Assay kit on a Qubit 3.0 fluorometer (Thermo Fisher Scientific, Waltham, MA). Sample indexing and library preparation were performed using the GemCode system and its associated reagents (10X Genomics, Pleasanton, CA) (Zheng et al. Nat Biotechnol. 2016 March; 34:303-11). In brief, 1ng of DNA was inputted for GEM reactions in which individual DNA molecules were partitioned to introduce specific barcodes and extend the DNA. After GEM reactions, sequencing libraries were prepared according to the manufacturer's recommendations. The libraries were quantified by qPCR using KAPA Library Quantification Kit (KAPA Biosystems, Wilmington, MA). The normalized libraries were sequenced on a HiSeq 2500 sequencer (Illumina, San Diego, CA), with paired-end sequencing of 98-bp, 14-bp 15 and 8-bp 17 index reads. Sequencing results were analyzed using Long Ranger software suite (10X Genomics) so that all heterozygous SNPs were phased and the two haplotypes of the patient was determined.

The plasma samples were sequenced using the Illumina to a depth of 17x. Copy number aberrations were detected in the plasma of the HCC patient according to the method as previously described (Chan et al. Clin Chem. 2013; 59:211-24).

Figure 20:
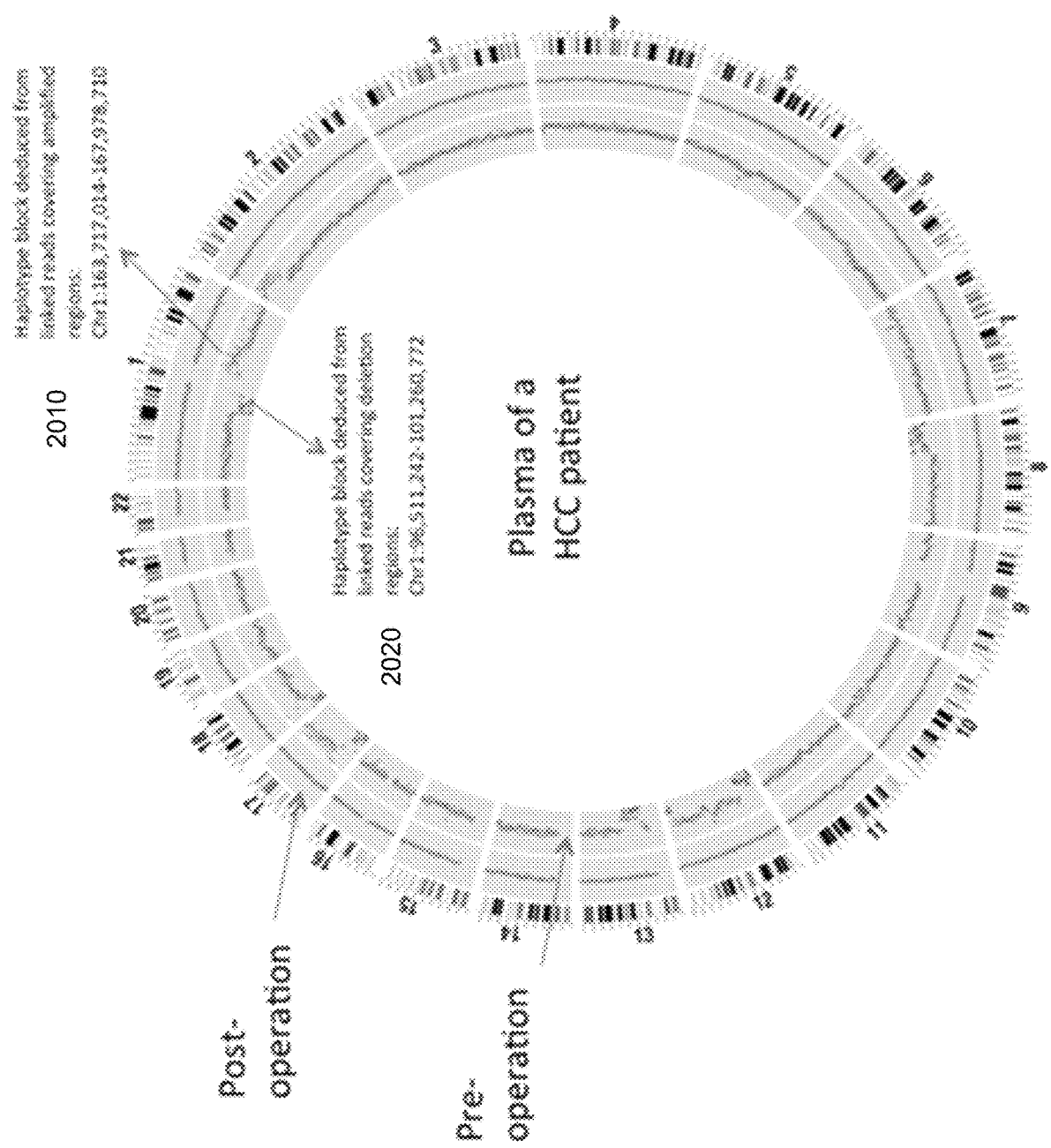
FIG. 20 shows a plot of copy number aberrations detected in the plasma of an HCC patient according to embodiments of the present invention.

FIG. 20 shows a plot of copy number aberrations detected in the plasma of an HCC patient according to embodiments of the present invention. The inner circle represents the result of the plasma sample collected at diagnosis (pre-operation) and the outer circle represents the result of the plasma sample collected at 3 months after the resection of the tumor (post-operation). Each dot represents a 1-Mb region. The green, red, and grey dots represent regions with copy number gain, copy number loss and no copy number change, respectively. Copy number aberrations were detected in the plasma sample at diagnosis and these changes disappeared after the tumor was removed.

In FIG. 20, two regions are highlighted for having a CNA. Region 2010 has a copy number gain, and region 2020 has a copy number loss. The haplotypes of these regions can be determined using any tissue sample of the subject, and not just a tumor sample. The difference in copy number is what is driving the difference in the fractional contributions, and that difference should be greatest in the tissue type with the tumor.

B. Determining the Tissue Origin of the Copy Number Aberrations

We performed methylation deconvolution analysis for the two haplotypes independently. For illustration purposes, the two haplotypes are named Hap I and Hap II. The plasma DNA molecules covering heterozygous SNPs and at least one CpG site were used for this analysis. Plasma DNA molecules carrying the SNP alleles on Hap I were analyzed independently from those carrying alleles on Hap II. The methylation status of the CpG sites were used for methylation deconvolution for molecules mapped to Hap I and Hap II independently. As a result, the tissue contribution to Hap I and Hap II in plasma DNA could be determined.

First we focused on the regions with amplification. For illustration purposes, we analyzed the amplified region on chromosome 1q as an example.

|        | At diagnosis | After tumor resection |
|--------|--------------|-----------------------|
| Hap I  | 34,119       | 11,131                |
| Hap II | 26,582       | 11,176                |

Table 11 shows the number of sequence reads from the two haplotypes. At diagnosis, the number of reads mapped to Hap I was increased compared with the number of reads mapped to Hap II. This indicated that Hap I is amplified relative to Hap II. This observation is compatible with the fact that a particular chromosome is duplicated in cancer rather than both homologous chromosomes being amplified to the same extent, which was in line with the fact that the copy number aberrations occurs preferentially on one haplotype (Adey A. et al, Nature. 2013; 500:207-11; LaFramboise T. et al, PLoS Comput Biol. 2005; 1(6):e65). The difference in the dosage of the two haplotypes disappeared after the tumor was resected. The difference in the absolute sequence reads number between the plasma samples taken at diagnosis and after tumor resection was due to the difference in the total number of sequence reads generated for the two plasma samples.

|  | At diagnosis | | | After tumor resection | | |
| --- | --- | --- | --- | --- | --- | --- |
|  | Hap I | Hap II | Difference | Hap I | Hap II | Difference |
| liver | 19.7 | 8.0 | 11.7 | 21.3 | 21.9 | −0.6 |
| Lung | 5.4 | 0 | 5.4 | 0 | 0 | 0 |
| Colon | 0 | 0 | 0 | 0 | 0 | 0 |
| Brain | 0 | 0 | 0 | 9.0 | 9.0 | 0 |
| Heart | 0 | 17.0 | −17 | 3.0 | 2.5 | −0.5 |
| Blood cell | 74.9 | 75.0 | 0 | 66.7 | 66.6 | 0.1 |
| Total | 100 | 100 | 0 | 100 | 100 | 0 |

Table 12 shows a percentage contribution of different tissues to plasma DNA for the two haplotypes at diagnosis and after tumor resection. At diagnosis, the contributions of liver to plasma DNA were 19.7% and 8.0% for Hap I and Hap II, respectively. A difference of 11.7% was the highest among different types of tissue. This indicated that the dosage difference between Hap I and Hap II in the plasma was most likely contributed from the contribution of the liver. This further indicated that the likely origin of the chromosomal aberration was from the liver because the copy number changes was most likely due to the duplication of Hap I in the sequence read counts analysis. In another embodiment, the difference in the contribution for Hap I and Hap II can be ranked to indicate the relative likelihood of different tissues being the source of the copy number aberrations.

The value for the heart is −17, which is in the opposite direction of the copy number aberration identified by Table 11. Thus, although the absolute value for the heart is larger than the absolute value for the liver, the opposite sign would discount the heart as being a viable candidate for the tissue type of the origin of the tumor. As the total contribution of all organs is 100%, the positive difference in the contributions of liver results in other tissues having negative values.

Similarly, this haplotype-specific methylation deconvolution can also be performed on regions with copy number loss. For illustration purpose, we performed this analysis on a region on chromosome 1p that exhibited copy number loss.

|  | At diagnosis | After tumor resection |
| --- | --- | --- |
| Hap I | 19,973 | 8,323 |
| Hap II | 12,383 | 7,724 |

Table 13 shows a number of sequence reads from the two haplotypes. At diagnosis, the number of reads mapped to Hap II was decreased compared with the number of reads mapped to Hap I. In tumor tissues, most of the regions with chromosome copy number loss would only involve the deletion of one of the two chromosomes. Thus the relative reduction in the dosage of Hap II was compatible with the deletion of Hap II. The difference in the dosage of the two haplotypes disappeared after the tumor was resected indicated that the amount of tumor-derived DNA had decreased or disappeared from the plasma.

|  | At diagnosis | | | After tumor resection | | |
| --- | --- | --- | --- | --- | --- | --- |
|  | Hap I | Hap II | Difference (Hap I − Hap II) | Hap I | Hap II | Difference (Hap I − Hap II) |
| liver | 13.3 | 5.5 | 7.8 | 10.2 | 13.2 | −3 |
| Lung | 0 | 0 | 0 | 4.1 | 0.5 | 3.6 |
| Colon | 3.8 | 0 | 3.8 | 8.6 | 17.5 | −8.9 |
| Brain | 0 | 0 | 0 | 0 | 0 | 0 |
| Heart | 3.7 | 0 | 3.7 | 25.5 | 19.4 | 6.1 |
| Blood cell | 79.2 | 94.5 | −15.3 | 51.6 | 49.4 | 2.2 |
| Total | 100 | 100 | 0 | 100 | 100 | 0 |

Table 14 shows a percentage contribution of different tissues to plasma DNA for the two haplotypes at diagnosis and after tumor resection. At diagnosis, the contributions of liver to plasma DNA were 13.3% and 5.5% for Hap I and Hap II, respectively. A difference of 7.8% was the highest among different types of tissue. This indicated that the dosage difference between Hap I and Hap II in the plasma was most likely contributed from the contribution of the liver. This further indicated that the likely origin of the chromosomal aberration was from the liver because the copy number changes was most likely due to the deletion of Hap II in the sequence read counts analysis. In another embodiment, the difference in the contribution for Hap I and Hap II can be ranked to indicate the relative likelihood of different tissues being the source of the copy number aberrations.

C. Method of Determining Tissue Origin of Tumor

Figure 21:
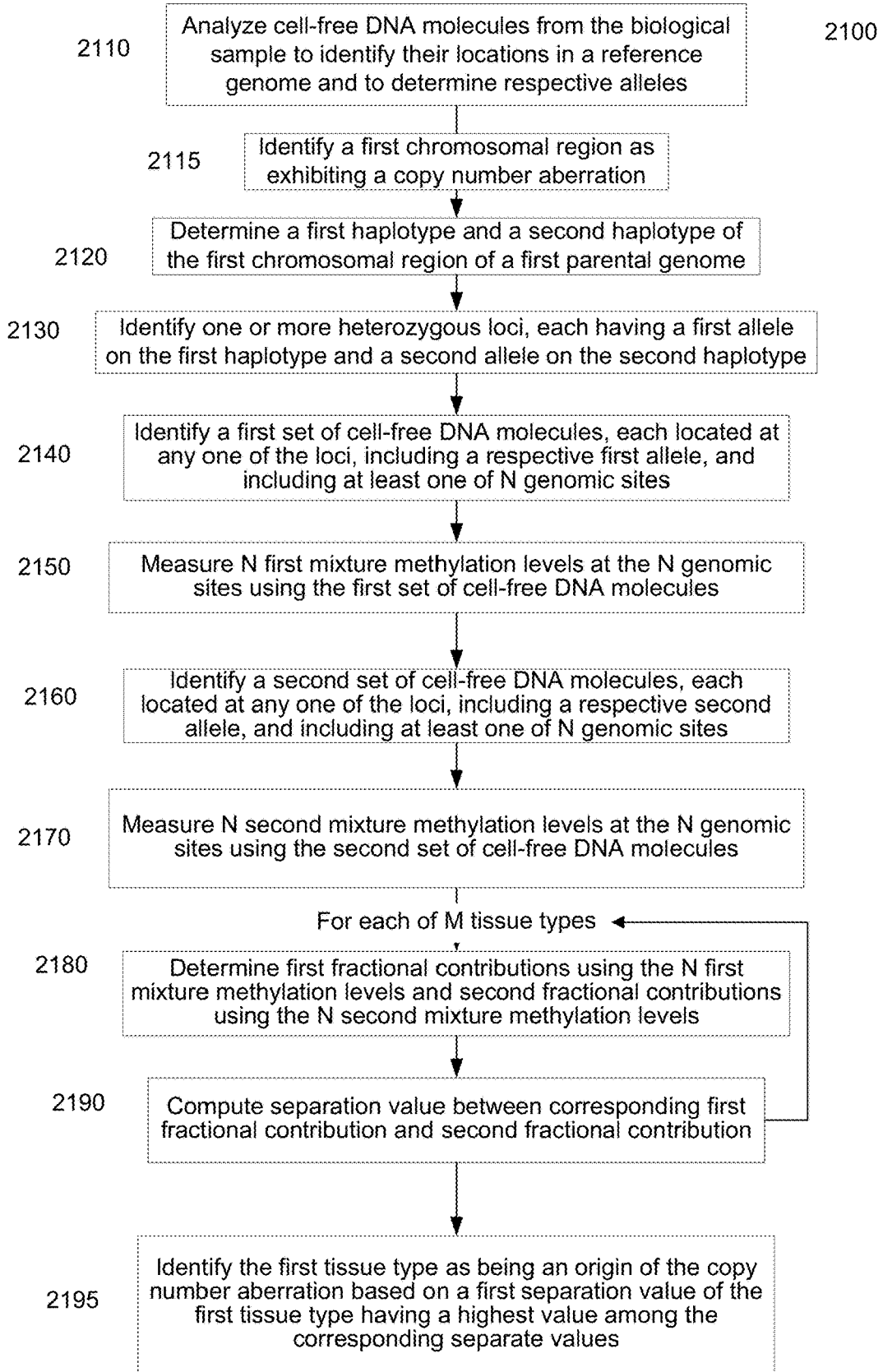
FIG. 21 is a flowchart illustrating a method of analyzing a biological sample of an organism to identify an origin of a chromosomal aberration according to embodiments of the present invention.

FIG. 21 is a flowchart illustrating a method of analyzing a biological sample of an organism to identify an origin of a chromosomal aberration according to embodiments of the present invention. The biological sample includes a mixture of cell-free DNA molecules from a plurality of tissues types that include a first tissue type.

At block 2110, a plurality of cell-free DNA molecules from the biological sample are analyzed. Block 2110 can be performed using techniques described in block 1910 of FIG. 1 and block 140 of method 100 of FIG. 1, as well as other blocks describing similar features.

At block 2115, a first chromosomal region is identified as exhibiting a copy number aberration in the organism based on a first amount of cell-free DNA molecules that are located in the first chromosomal region. As an example, plasma DNA analysis is performed to identify regions that exhibit copy number aberrations. The aberration can correspond to over or under-representation. In some embodiments, the genome can be separated into bins (e.g., 1-Mb bins), and the amount of cell-free DNA molecules from a particular bin can be determined (e.g., by mapping sequence reads to that part of a reference genome). The amount for a particular bin can be normalized (e.g., with respect to an average amount for a bin) can an over or under-representation can be identified.

Other techniques than counting DNA molecules mapping to a particular region can be used. For example, a distribution of sizes of the DNA molecules aligning to the first chromosomal region can be used to detect the CNA. For example, cell-free tumor DNA is smaller than cell-free DNA from normal cells. This difference in size can be used to detect differences in a size distribution (e.g., average size or ratio of number of DNA molecules at different sizes) between two haplotypes for the region, or between the region and another region.

At block 2120, a first haplotype and a second haplotype of the organism in the first chromosomal region are determined. The two haplotypes may have been determined as part of block 2115. The two haplotypes can be determined using the same cell-free mixture or from a different sample, e.g., a cellular sample.

At block 2130, one or more heterozygous loci of the first chromosomal region are identified. Each heterozygous locus includes a corresponding first allele in the first haplotype and a corresponding second allele in the second haplotype. Block 2130 may be performed in a similar manner as other similar blocks of methods described herein.

At block 2140, a first set of the plurality of cell-free DNA molecules are identified. Each DNA molecule of the first set is located at any one of the one or more heterozygous loci, includes the corresponding first allele of the heterozygous locus, and includes at least one of N genomic sites. N is an integer greater than or equal to 2. Block 2140 may be performed in a similar manner as other similar blocks of methods described herein.

At block 2150, N first mixture methylation levels at the N genomic sites are measured using the first set of the plurality of cell-free DNA molecules. Block 2150 may be performed in a similar manner as other similar blocks of methods described herein.

At block 2160, a second set of the plurality of cell-free DNA molecules is identified. Each DNA molecule of the second set is located at any one of the one or more heterozygous loci, includes the corresponding second allele of the heterozygous locus, and includes at least one of the N genomic sites. Block 2160 may be performed in a similar manner as other similar blocks of methods described herein.

In some embodiments, a first number of cell-free DNA molecules in the first set of the plurality of cell-free DNA molecules can be determined, and a second number of cell-free DNA molecules in the second set of the plurality of cell-free DNA molecules can be determined, e.g., as shown in table 11. It can be determined which number is higher, thereby providing information about the expected separation value for the tissue of origin, e.g., which haplotype should have a higher fractional contribution.

The first set of the plurality of cell-free DNA molecules can have a first size distribution, and the second set of the plurality of cell-free DNA molecules can have a second size distribution. A statistical value of a size distribution of the DNA molecules can be determined for each haplotype, thereby providing a first statistical value and a second statistical value. The haplotype with the smaller size distribution would be expected to have a higher copy number than the other haplotype, as tumor cell-free DNA is known to be smaller, as described in U.S. Pat. No. 8,741,811. Examples of a statistical value of a size distribution are a ratio of a number of DNA molecules at different sizes, an average size, or a percentage of the DNA molecules at a specific size (e.g., below a size cutoff).

At block 2170, N second mixture methylation levels at the N genomic sites are measured using the second set of the plurality of cell-free DNA molecules. Block 2170 may be performed in a similar manner as other similar blocks of methods described herein.

Blocks 2180 and 2190 may be performed for each of a plurality of M tissue types. The M tissue types can include a default list of tissue types that are screened and for which reference methylation levels may be known. The default list can include tissues that cancer is most predominantly seen. M is an integer greater than one.

At block 2180, a computer system determines a corresponding first fractional contribution of the tissue type in the mixture using the N first methylation levels. The computer system determines a corresponding second fractional contribution of the tissue type in the mixture using the N second methylation levels. Block 2180 may be performed in a similar manner as other similar blocks of methods described herein.

At block 2190, a corresponding separation value between the corresponding first fractional contribution and the corresponding second fractional contribution is computed. Various separation values can be used, e.g., as are described herein.

At block 2195, the first tissue type is identified as being an origin of the copy number aberration based on a first separation value of the first tissue type having a maximal value among the corresponding separate values. The determination can require that the highest separation value be sufficiently higher than the second highest separation value. For example, the difference can be required to be at least a threshold value, e.g., 1%, 2%, 35, 4%, 5%, 6%, or 7%. In one implementation, a difference between the first separation value and a next highest separation value can be compared to a threshold to determine a classification of how likely the first tissue type is the origin of the copy number aberration. Thus, even if the difference is not above the threshold, a probability or other classification can be provided. For instance, a linear relationship can be used from 0 to the threshold, where the probability is 100% once the difference is equal to the threshold.

Depending on how the separation value is determined, the maximal value can be a maximum negative number or a maximum positive number. For example, the difference values in table 14 could be determined using Hap II-Hap I. Whether the maximum should be a positive or a negative value can be determined using the analysis of DNA molecules on each haplotype, e.g., a count as in Table 13 or a size analysis as described above. In some implementations, the separation value can always be determined such that a maximum positive value is expected, e.g., by subtracting the fractional contribution of the haplotype with a lower copy number from the fractional contribution of the haplotype with the higher copy number.

After the origin is identified, an investigation using imaging modalities, e.g. computed tomography (CT) scan or magnetic resonance imaging (MRI), of the subject (entire subject or specifically of the candidate organ) can be performed to confirm or rule out the presence of a tumor in the organ. If presence of a tumor is confirmed, treatment can be performed, e.g., surgery (by a knife or by radiation) or chemotherapy.

IX. Computer System

Figure 22:
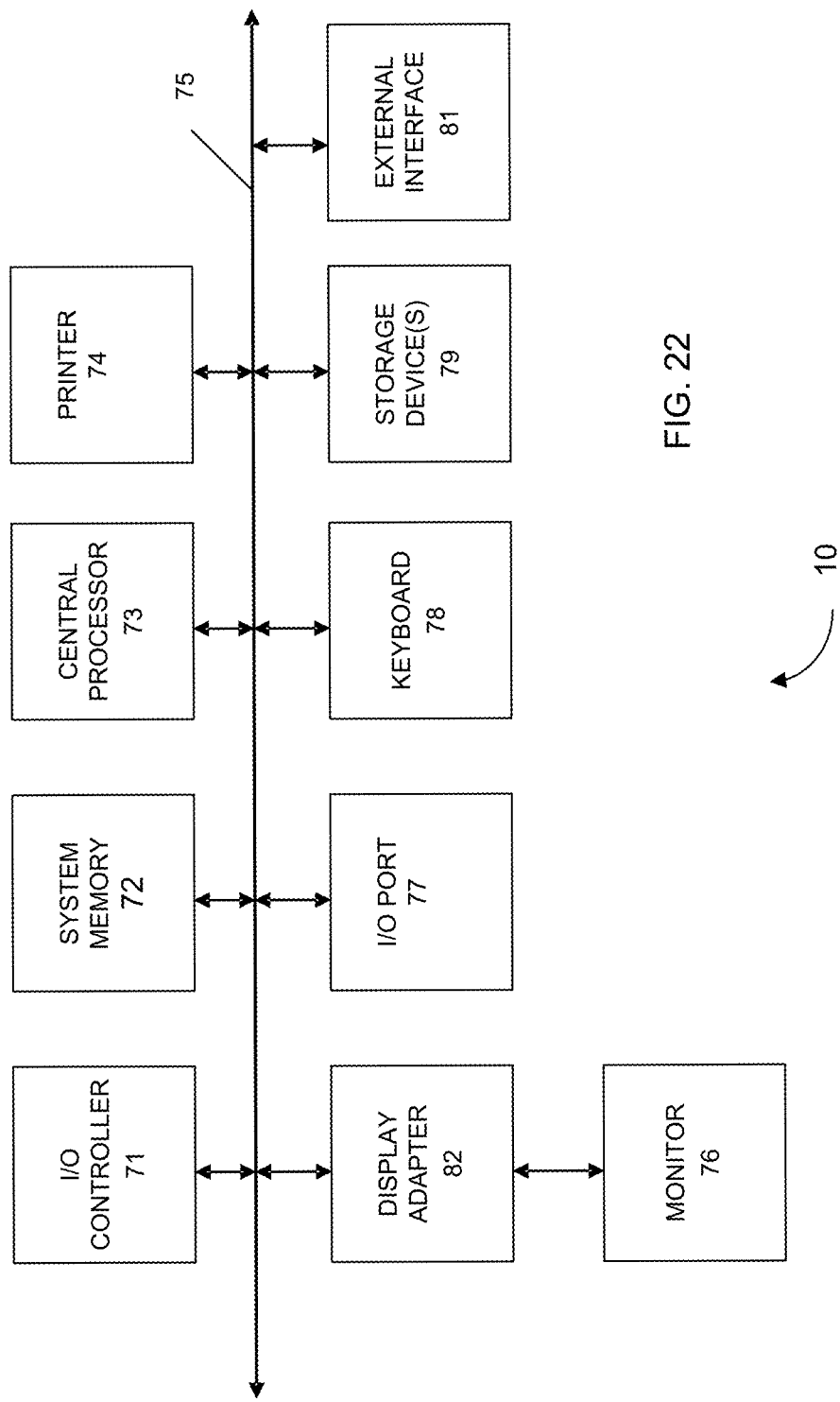
FIG. 22 shows a block diagram of an example computer system 10 usable with system and methods according to embodiments of the present invention.

Any of the computer systems mentioned herein may utilize any suitable number of subsystems. Examples of such subsystems are shown in FIG. 22 in computer apparatus 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 22 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C #, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover reference to a "first" or a "second" component does not limit the referenced component to a particular location unless expressly stated.

All patents, patent applications, publications, and descriptions mentioned herein are incorporated by reference in their entirety for all purposes. None is admitted to be prior art.

What is claimed is:

1. A method of analyzing a biological sample of an organism, the biological sample including a mixture of cell-free DNA molecules from a plurality of tissues types, including a first tissue type, the method comprising:
   analyzing, by a computer system, a plurality of cell-free DNA molecules from the biological sample, the plurality of cell-free DNA molecules being at least 1,000 cell-free DNA molecules, wherein analyzing a cell-free DNA molecule includes:
      identifying a location of the cell-free DNA molecule in a reference genome corresponding to the organism; and
      determining a respective allele of the cell-free DNA molecule;
   identifying one or more loci, each having a corresponding first allele on a first haplotype of a first chromosomal region, wherein the first haplotype is:

not present in healthy cells of the organism, or
present in the healthy cells of the organism and not present in abnormal cells that may be in the mixture;
identifying a first set of the plurality of cell-free DNA molecules that each:
is located at any one locus of the one or more loci,
includes the corresponding first allele of the one locus, and
includes at least one of N genomic sites, N being an integer greater than or equal to 2;
measuring N first mixture methylation levels at the N genomic sites using the first set of the plurality of cell-free DNA molecules;
determining, by the computer system, a first fractional contribution of the first tissue type in the first set of the plurality of cell-free DNA molecules from the mixture using the N first mixture methylation levels;
determining a first separation value between the first fractional contribution and a reference fractional contribution; and
comparing the first separation value to a threshold value to determine a classification of whether the first tissue type has a disease state.

2. The method of claim 1, wherein the first haplotype is on a first chromosome, and wherein the first tissue type has the first haplotype on both copies of the first chromosome.

3. The method of claim 1, wherein the first haplotype is not present in the healthy cells of the organism, and wherein the first haplotype is associated with the disease state.

4. The method of claim 3, wherein the first tissue type is determined to have the disease state when the first separation value is greater than the threshold value.

5. The method of claim 3, further comprising:
identifying a second set of the plurality of cell-free DNA molecules that each:
is located at any one of the one or more loci;
includes a corresponding second allele on a second haplotype of the first chromosomal region, the second haplotype not being present in the healthy cells of the organism, and the second haplotype associated with the disease state; and
includes at least one of the N genomic sites;
measuring N second mixture methylation levels at the N genomic sites using the second set of the plurality of cell-free DNA molecules;
determining, by the computer system, a second fractional contribution of the first tissue type in the second set of the plurality of cell-free DNA molecules from the mixture using the N second mixture methylation levels;
determining a second separation value between the second fractional contribution and the reference fractional contribution; and
comparing the second separation value to the threshold value as part of determining the classification of whether the first tissue type has the disease state.

6. The method of claim 3, wherein the disease state is cancer.

7. The method of claim 6, wherein a particular cancer has the first haplotype in a cancer genome of the particular cancer.

8. The method of claim 7, wherein the particular cancer is selected from the group consisting of liver cancer, lung cancer, pancreas cancer, atrium cancer, colon cancer, sigmoid colon cancer, transverse colon cancer, ascending colon cancer, descending colon cancer, adrenal gland cancer, esophagus cancer, small intestines cancer, and CD4 T cell cancer.

9. The method of claim 6, wherein the classification of whether the first tissue type has cancer comprises classification of a presence or an absence of the cancer, classification of a stage of cancer, classification of a size of a tumor, and/or classification of metastasis.

10. The method of claim 3, further comprising performing, by the computer system:
determining a plurality of corresponding fractional contributions of other tissue types in the first set of the plurality of cell-free DNA molecules from the mixture using the N first mixture methylation levels;
determining corresponding separation values between the plurality of corresponding fractional contributions and corresponding reference fractional contributions; and
comparing the corresponding separation values to the threshold value to determine classifications of whether each of the other tissue types has the disease state.

11. The method of claim 3, wherein the corresponding first allele at each of the one or more loci is a cancer-specific mutation.

12. The method of claim 1, further comprising:
determining the corresponding first allele at each of the one or more loci on the first haplotype by:
analyzing DNA molecules of a tissue sample having the first haplotype to determine the first haplotype.

13. The method of claim 1, wherein the disease state is a rejection of a transplant of the first tissue type in the organism.

14. The method of claim 13, wherein the reference fractional contribution is determined from one or more measurements of biological samples of organisms with the first tissue type being healthy.

15. The method of claim 13, wherein the reference fractional contribution is determined from one or more measurements of biological samples of organisms whose transplanted first tissue is not being rejected.

16. The method of claim 1, wherein the reference fractional contribution is zero.

17. The method of claim 1, wherein the N first mixture methylation levels form a methylation vector b, and wherein determining the first fractional contribution of the first tissue type includes:
for each of M tissue types:
obtaining N tissue-specific methylation levels at the N genomic sites, N being greater than or equal to M, wherein the N tissue-specific methylation levels form a matrix A of dimensions N by M, the M tissue types including the first tissue type, M being an integer greater than one;
solving for a composition vector x that provides the methylation vector b for the matrix A; and
for each component of one or more components of the composition vector x:
using the component to determine a corresponding fractional contribution of a corresponding tissue type of the M tissue types in the first set of the plurality of cell-free DNA molecules from the mixture.

18. The method of claim 1, wherein the first haplotype is present in the healthy cells of the organism and not present in the abnormal cells that may be in the mixture.

19. The method of claim 18, wherein the abnormal cells are from a tumor.

20. The method of claim 18, wherein the abnormal cells are from donor tissue.

21. The method of claim 1, wherein the first tissue type is determined to have the disease state when the first separation value is less than the threshold value.

22. A computer product comprising a non-transitory computer readable medium storing a plurality of instructions for analyzing a biological sample of an organism, the biological sample including a mixture of cell-free DNA molecules from a plurality of tissues types, including a first tissue type, wherein the plurality of instructions, when executed, cause one or more processors of a computer system to perform:

analyzing a plurality of cell-free DNA molecules from the biological sample, the plurality of cell-free DNA molecules being at least 1,000 cell-free DNA molecules, wherein analyzing a cell-free DNA molecule includes:
        identifying a location of the cell-free DNA molecule in a reference genome corresponding to the organism; and
        determining a respective allele of the cell-free DNA molecule;
    identifying one or more loci, each having a corresponding first allele on a first haplotype of a first chromosomal region, wherein the first haplotype is:
        not present in healthy cells of the organism, or
        present in the healthy cells of the organism and not present in abnormal cells that may be in the mixture;
    identifying a first set of the plurality of cell-free DNA molecules that each:
        is located at any one locus of the one or more loci,
        includes the corresponding first allele of the one locus, and
        includes at least one of N genomic sites, N being an integer greater than or equal to 2;
    measuring N first mixture methylation levels at the N genomic sites using the first set of the plurality of cell-free DNA molecules;
    determining a first fractional contribution of the first tissue type in the first set of the plurality of cell-free DNA molecules from the mixture using the N first mixture methylation levels;
    determining a first separation value between the first fractional contribution and a reference fractional contribution; and
    comparing the first separation value to a threshold value to determine a classification of whether the first tissue type has a disease state.

23. A system for analyzing a biological sample of an organism, the biological sample including a mixture of cell-free DNA molecules from a plurality of tissues types, including a first tissue type, the system comprising:

an apparatus configured to perform an assay on a plurality of cell-free DNA molecules from the biological sample to provide measurement data, the plurality of cell-free DNA molecules being at least 1,000 cell-free DNA molecules;
    a computer system configured to receive the measurement data and to perform:
        analyzing the plurality of cell-free DNA molecules from the biological sample, wherein analyzing a cell-free DNA molecule includes:
            identifying a location of the cell-free DNA molecule in a reference genome corresponding to the organism; and
            determining a respective allele of the cell-free DNA molecule;
        identifying one or more loci, each having a corresponding first allele on a first haplotype of a first chromosomal region, wherein the first haplotype is:
            not present in healthy cells of the organism, or
            present in the healthy cells of the organism and not present in abnormal cells that may be in the mixture;
        identifying a first set of the plurality of cell-free DNA molecules that each:
            is located at any one locus of the one or more loci,
            includes the corresponding first allele of the one locus, and
            includes at least one of N genomic sites, N being an integer greater than or equal to 2;
        measuring N first mixture methylation levels at the N genomic sites using the first set of the plurality of cell-free DNA molecules;
        determining a first fractional contribution of the first tissue type in the first set of the plurality of cell-free DNA molecules from the mixture using the N first mixture methylation levels;
        determining a first separation value between the first fractional contribution and a reference fractional contribution; and
        comparing the first separation value to a threshold value to determine a classification of whether the first tissue type has a disease state.

\* \* \* \* \*